United States Patent
Haystead et al.

(10) Patent No.: US 11,261,187 B2
(45) Date of Patent: Mar. 1, 2022

(54) COMPOUNDS AND METHODS FOR TARGETING HSP90

(71) Applicant: Duke University, Durham, NC (US)

(72) Inventors: Timothy A. J. Haystead, Chapel Hill, NC (US); Philip Floyd Hughes, Chapel Hill, NC (US)

(73) Assignee: Duke University, Durham, NC (US)

( * ) Notice: Subject to any disclaimer, the term of this patent is extended or adjusted under 35 U.S.C. 154(b) by 442 days.

(21) Appl. No.: 16/095,411

(22) PCT Filed: Apr. 21, 2017

(86) PCT No.: PCT/US2017/028797
§ 371 (c)(1),
(2) Date: Oct. 22, 2018

(87) PCT Pub. No.: WO2017/184956
PCT Pub. Date: Oct. 26, 2017

(65) Prior Publication Data
US 2020/0354365 A1    Nov. 12, 2020

Related U.S. Application Data

(60) Provisional application No. 62/380,763, filed on Aug. 29, 2016, provisional application No. 62/326,411, filed on Apr. 22, 2016.

(51) Int. Cl.
C07D 487/04   (2006.01)
C07D 403/14   (2006.01)
C07D 491/107  (2006.01)
C07D 498/06   (2006.01)

(52) U.S. Cl.
CPC ......... C07D 487/04 (2013.01); C07D 403/14 (2013.01); C07D 491/107 (2013.01); C07D 498/06 (2013.01)

(58) Field of Classification Search
CPC .. C07D 403/14; C07D 487/04; C07D 498/06; C07D 491/107; C07K 7/52; A61K 31/416; A61K 31/4425; A61K 31/519; A61K 38/12; A61K 31/537; A61P 35/00
See application file for complete search history.

(56) References Cited

U.S. PATENT DOCUMENTS

| | | | |
|---|---|---|---|
| 5,260,291 A | 11/1993 | Lunt et al. | |
| 5,747,498 A | 5/1998 | Schnur et al. | |
| 7,344,699 B2 | 3/2008 | Lappin et al. | |
| 7,358,370 B2 | 4/2008 | Huang et al. | |
| 7,612,201 B2 | 11/2009 | Beswick et al. | |
| 7,678,803 B2 | 3/2010 | Huang et al. | |
| 7,906,529 B2 | 3/2011 | Huang et al. | |
| 7,928,135 B2 | 4/2011 | Huang et al. | |
| 9,738,643 B2 | 8/2017 | Haystead et al. | |
| 2007/0207984 A1 | 9/2007 | Huang et al. | |
| 2008/0139587 A1 | 6/2008 | Huang et al. | |
| 2008/0269193 A1 | 10/2008 | Huang et al. | |
| 2009/0179638 A1 | 7/2009 | Barker et al. | |
| 2009/0226431 A1 | 9/2009 | Habib | |
| 2009/0298857 A1 | 10/2009 | Chiosis et al. | |
| 2011/0065198 A1 | 3/2011 | Firebe et al. | |
| 2011/0183977 A1 | 7/2011 | Huang et al. | |
| 2013/0190509 A1 | 7/2013 | Wang et al. | |
| 2014/0079636 A1 | 3/2014 | Chimmanamada et al. | |
| 2014/0080895 A1 | 3/2014 | Gleave et al. | |
| 2015/0139905 A1 | 5/2015 | Chimmanamada et al. | |

FOREIGN PATENT DOCUMENTS

| | | |
|---|---|---|
| CA | 2093203 | 11/2002 |
| EP | 0520722 | 12/1992 |
| EP | 0564409 | 10/1993 |
| EP | 0566226 | 10/1993 |
| EP | 0787722 | 8/1997 |
| EP | 0837063 | 4/1998 |
| WO | 96/33980 | 10/1996 |
| WO | 97/02266 | 1/1997 |
| WO | 97/30034 | 8/1997 |
| WO | 97/38983 | 10/1997 |
| WO | 97/49688 | 12/1997 |
| WO | 98/10767 | 3/1998 |
| WO | 99/03854 | 1/1999 |
| WO | 02/22577 | 3/2002 |
| WO | 03/013541 | 2/2003 |
| WO | 2006/084030 | 8/2006 |
| WO | 2008/130879 | 10/2008 |
| WO | 2011/116181 | 9/2011 |
| WO | 2012/045237 | 4/2012 |
| WO | 2014/025395 | 2/2014 |
| WO | 2015/114171 | 8/2015 |

OTHER PUBLICATIONS

TREPEL. Nature Reviews: Cancer, 2010, 10, 537-549 (Year: 2010).*
Barrott et al., "Optical and radioiodinated tethered Hsp90 inhibitors reveal selective internalization of ectopic Hsp90 in malignant breast tumor cells," Chem. Biol., 2013, 20(9):1187-97.
Bulinski, "Overexpression of MAP4 inhibits organelle motility and trafficking in vivo," J. Cell Sci., 1997, 110:3055-3064.
Caldas-Lopes et al., "Hsp90 inhibitor PU-H71, a multimodal inhibitor of malignancy, induces complete responses in triple-negative breast cancer models," Proc Natl Acad Sci U S A, 2009, 106(20):8368-73.
Chandarlapaty et al., "SNX2112, a synthetic heat shock protein 90 inhibitor, has potent antitumor activity against HER kinase-dependent cancers," Cancer Res., 2008, 14(1) 240.

(Continued)

*Primary Examiner* — Noble E Jarrell
(74) *Attorney, Agent, or Firm* — Michael Best & Friedrich LLP

(57) ABSTRACT

Described herein are compounds that may selectively bind to Hsp90, methods of using the compounds, and kits including the compounds. The compounds may allow for selective detection of Hsp90 in a sample.

21 Claims, 17 Drawing Sheets

(56) References Cited

OTHER PUBLICATIONS

Chun et al., "Regiospecific Syntheses of Functionalized Diaryliodonium Tosylates via [Hydroxy(tosyloxy)iodo]arenes Generated in Situ from (Diacetoxyiodo)arenes," J. Org. Chem., 2012, 77, 1931-1938.
Graves et al., "Discovery of novel targets of quinoline drugs in the human purine binding proteome," Mol. Pharmacol., 2002, 62(6):1364.
Huang et al., "Discovery of novel 2-aminobenzamide inhibitors of heat shock protein 90 as potent, selective and orally active antitumor agents," J. Med. Chem., 2009, 52(14):4288.
Hughes et al., "A highly selective Hsp90 affinity chromatography resin with cleavable linker," Bioorganic & Medicinal Chemistry 20, 2012, 3298-3305.
Koziorowski et al., "A new convenient route to radioiodinated N-succinimidyl 3- and 4-iodobenzoate, two reagents for radioiodination of proteins," Appl. Radiat. Isot., 1998, vol. 49, No. 8, pp. 955-959.
Muhlradt et al., "Epothilone B stabilizes microtubuli of macrophages like taxol without showing taxol-like endotoxin activity," Cancer Res., 1997, 57:3344-3346.
Nicolaou et al., "Synthesis of epothilones A and B in solid and solution phase," Nature, 1997, 387:268-272.
Panda et al., "Differential Effects of Vinblastine on Polymerization and Dynamics at Opposite Microtubule Ends," J. Biol. Chem., 1996, 271:29807-29812.
Panda, "Stabilization of microtubule dynamics by estramustine by binding to a novel site in tubulin: A possible mechanistic basis for its antitumor action," Proc. Natl. Acad. Sci. USA, 1997, 94:10560-10564.
Schulte et al., "The benzoquinone ansamycin 17-allylamino-17-demethoxygeldanamycin binds to Hsp90 and shares important biologic activities with geldanamycin," Cancer Chemoth. Pharm., 1998, 42(4) 273.
Taldone et al., "Design, synthesis, and evaluation of small molecule Hsp90 probes," Bioorganic & Medicinal Chemistry 19, 2011, 2603-2614.
Taldone et al., "Synthesis of purine-scaffold fluorescent probes for heay shock protein 90 with use in flow cytometry and fluorescence microscopy," Bioorganic & Medicinal Chemistry Letters 21, 2011, 5347-5352.
Vasquez, "Nanomolar concentrations of nocodazole alter microtubule dynamic instability in vivo and in vitro," Mol. Biol. Cell., 1997, 8:973-985.
Zagouri et al., "Hsp90 in the continuum of breast ductal carcinogenesis: Evaluation in precursors, preinvasive and ductal carcinoma lesions," BMC Cancer, 2010, 10:353.
Leamon et al., "Folate-targeted chemotherapy," Advanced Drug Delivery Reviews, 56, p. 1127-1141, 2004.
Koga et al., "Inhibition of cancer invasion and metastasis by targeting the molecular chaperone heat-shock protein 90," Anticancer Research 29, p. 797-808, 2009.
Wang et al., "STA-9090, a small-molecule Hsp90 inhibitor for the potential treatment of cancer," Current Opinion in Investigational Drugs 11 (12), p. 1466-1476, 2010.
International Search Report and Written Opinion for Application No. PCT/US2013/031614 dated May 23, 2013 (18 pages).
United States Patent Office Action for U.S. Appl. No. 14/419,965 dated Dec. 7, 2015 (14 pages).
United States Patent Office Final Action for U.S. Appl. No. 14/419,965 dated Apr. 12, 2016 (14 pages).
Extended European Search Report for Application No. 13828368.4 dated Apr. 26, 2016 (12 pages).
Extended European Examination Report for Application No. 13828368.4 dated Mar. 16, 2017 (4 pages).
International Search Report and Written Opinion for Application No. PCT/US2017/028797 dated Jul. 18, 2017 (14 pages).
United States Patent Office Action for U.S. Appl. No. 15/653,338 dated Feb. 9, 2018 (14 pages).
Boonjaraspinyo et al., "A Promising Serum Autoantibody Marker, Anti-Heat Shock Protein 90α, for Cholangiocarcinoma," Asian Pac J Cancer Prev, 2015, 16(14):5779-5785.
Chatterjee et al., "Targeting Heat Shock Proteins in Cancer: A Promising Therapeutic Approach," International Journal of Molecular Science, 2017, 18:1978, 39 pages.
Chen et al., "Secreted Heat Shock Protein 90α Induces Colorectal Cancer Cell Invasion through CD91/LRP-1 and NF-kB-mediated Integrin αv Expression," The Journal of Biological Chemistry, 2010, 285(33):25458-25466.
Lee et al., "Clinical Significance of Heat Shock Protein 90α Expression as a Biomarker of Prognosis in Patients With Gastric Cancer," Niger Clin Pract, 2019, 22:1698-1705.
Liu et al., "A novel pan-cancer biomarker plasma heat shock protein 90alpha and its diagnosis determinants in clinic," Cancer Science, 2019, 110:2941-2959.
Tang et al., "HSP90α combined with AFP and TK1 improved the diagnostic value for hepatocellular carcinoma," Biomark. Med., 2020, 14(10): 869-878.
Tian et al., "High expression of heat shock protein 90 alpha and its significance in human acute leukemia cells," Gene, 2014, 542:122-128.
Wei et al., "Diagnostic value of plasma HSP90α levels for detection of hepatocellular carcinoma," BMC Cancer, 2020, 20:6, 9 pages.
Yang et al., "The expression of HSP70 and HSP90α in children with Wilms tumor," Journal of Pediatric Surgery, 2006, 41:1062-1066.
Yin et al., "Heat Shock Protein 90 Triggers Multi-Drug Resistance of Ovarian Cancer via AKT/GSK3β/β-Catenin Signaling," Frontiers in Oncology, 2021, 11:620907, 16 pages.
Yun et al., "Heat Shock Proteins: Agents of Cancer Development and Therapeutic Targets in Anti-Cancer Therapy," Cells, 2020, 9:60, 30 pages.
Zhang et al., "Diagnostic and prognostic value of heat shock protein 90α in malignant melanoma," Melanoma Research, 2021, 31:152-161.

* cited by examiner

COMPOUNDS AND METHODS FOR TARGETING HSP90

CROSS-REFERENCE TO RELATED APPLICATIONS

This application is the U.S. national stage entry, under 35 U.S.C. § 371, of international application number PCT/US2017/028797, filed Apr. 21, 2017, which claims the benefit of U.S. Provisional Application No. 62/326,411, filed Apr. 22, 2016, and U.S. Provisional Application No. 62/380,763, filed Aug. 29, 2016; both of which are incorporated by reference herein.

STATEMENT REGARDING FEDERALLY SPONSORED RESEARCH

This invention was made with U.S. Government support awarded by the Department of Defense, Grant Nos. W81XWH-12-01-0447 and W81XWH-15-1-0072. The U.S. Government has certain rights in this invention.

BACKGROUND

Heat shock protein 90 (Hsp90), one of the most abundant proteins expressed in cells, regulates cellular homeostasis by chaperoning protein folding and trafficking. Hsp90 is also highly upregulated in response to stress. The N-terminal domain of Hsp90 includes an ATP binding site, and ATPase activity is necessary for all of its cellular functions. To date, over 200 Hsp90 "client" proteins have been identified and many of these are involved in signal transduction.

Hsp90 has been implicated in diseases such as cancer, and its expression is up-regulated during oncogenesis. High expression is associated with poor prognosis for cancers, such as breast cancer, prostate cancer, non-small cell lung cancer, colorectal cancer and melanoma.

Proteins such as glucose-regulated protein 94 (GRP94) and tumor necrosis factor receptor-associated protein (TRAP1) share homology with Hsp90 and both proteins also possess ATPase activity. While inhibitors of Hsp90 have been shown to have antiproliferative and antitumor activities, current Hsp90 inhibitors may bind nonspecifically to GRP94 and TRAP1. There is a need for compounds that selectively bind to Hsp90.

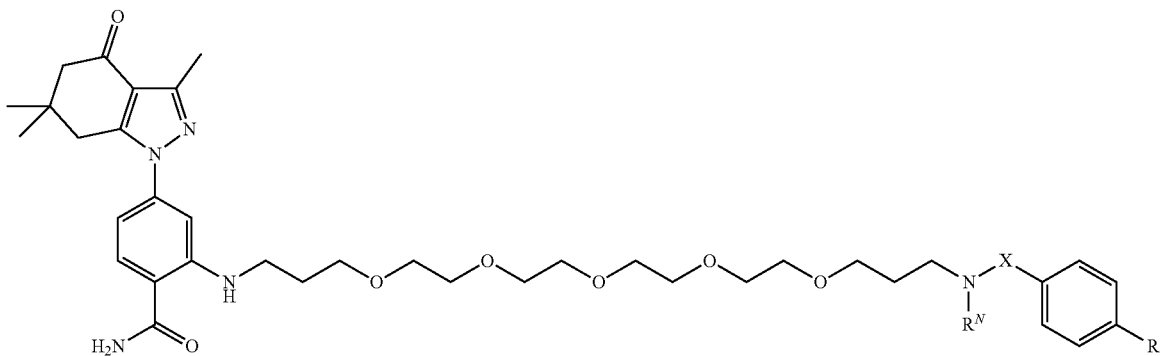

(I)

SUMMARY

In an aspect, the present disclosure provides a compound of formula (I):

and stereoisomers and salts thereof;
wherein
X is —CH$_2$— or —C(O)—;
R is H, —CH$_2$(C$_6$H$_4$)—I, or —CH$_2$(C$_6$H$_4$)—Sn(CH$_3$)$_3$;
R is

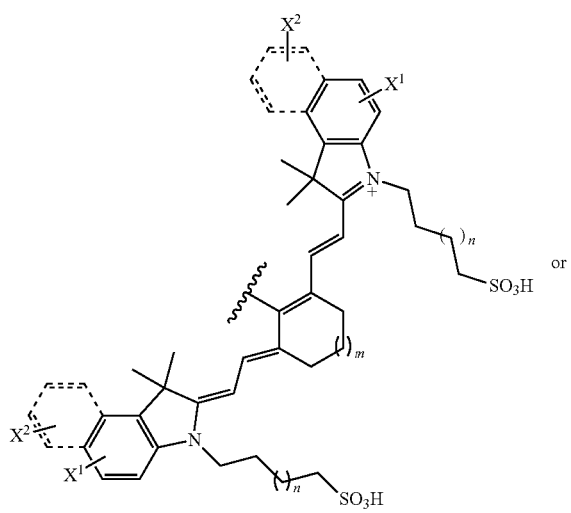

or

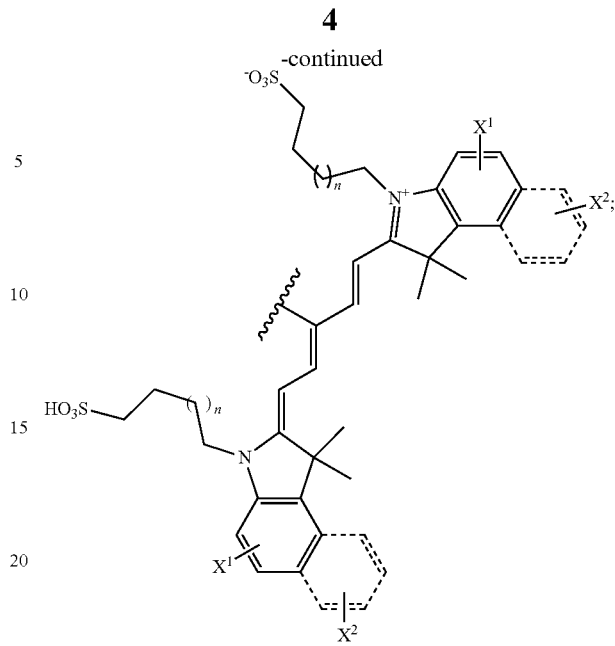

each X$^1$ and X$^2$, if present, are independently selected from H and SO$_3$H;
n is 0 or 1;
m is 0 or 1; and
the dotted lines show an optional fused ring.

In an aspect, the present disclosure provides a method of detecting cancer in a subject comprising contacting a biological sample from the subject with a compound as disclosed herein and detecting a signal.

In an aspect, the present disclosure provides a method of detecting Hsp90 in a sample comprising contacting the sample with a compound as disclosed herein and detecting a signal.

In an aspect, the present disclosure provides a method of treating cancer comprising administering to a subject in need thereof a therapeutically effective amount of a compound as disclosed herein.

In an aspect, the present disclosure provides a pharmaceutical composition comprising a compound as disclosed herein and a pharmaceutically acceptable carrier.

In an aspect, the present disclosure provides a kit comprising a compound as disclosed herein.

In an aspect, the present disclosure provides a compound selected from:

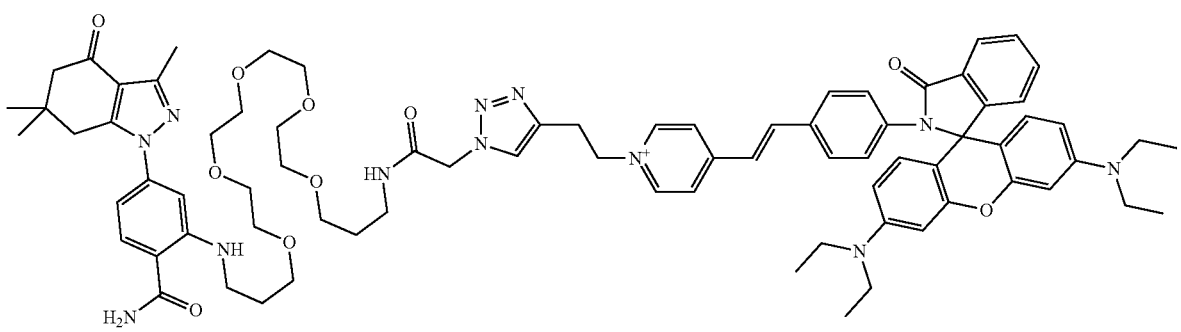

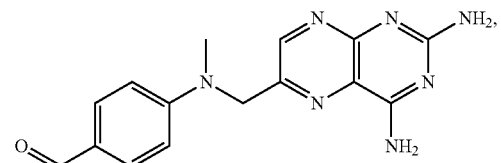
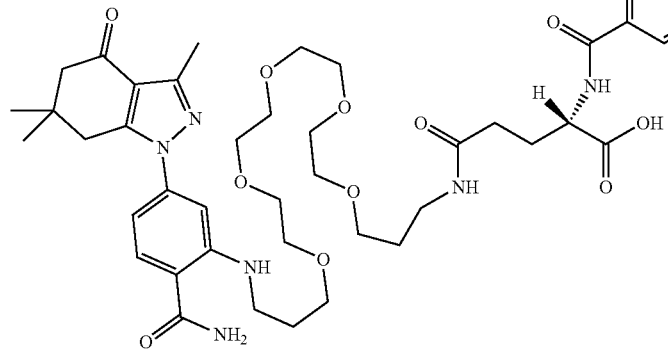
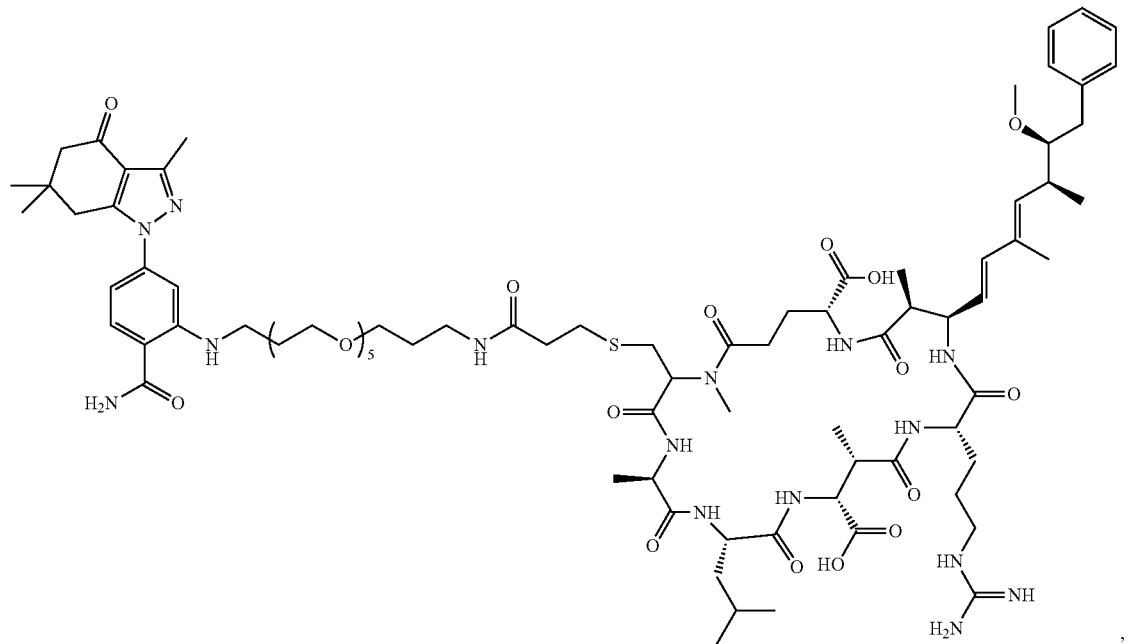
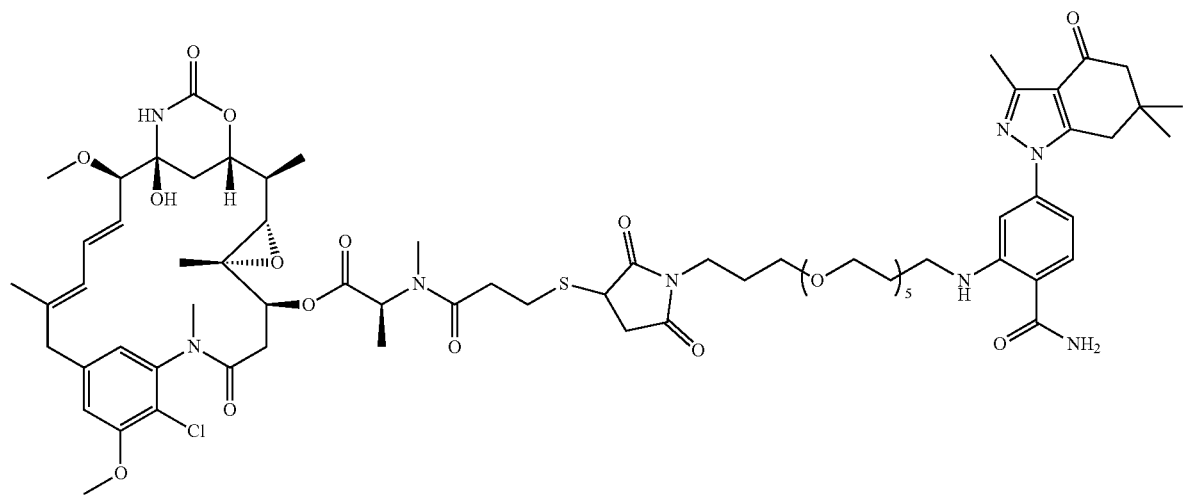

Other aspects and embodiments will become apparent in light of the following description and drawings.

DETAILED DESCRIPTION

Figure 1A:
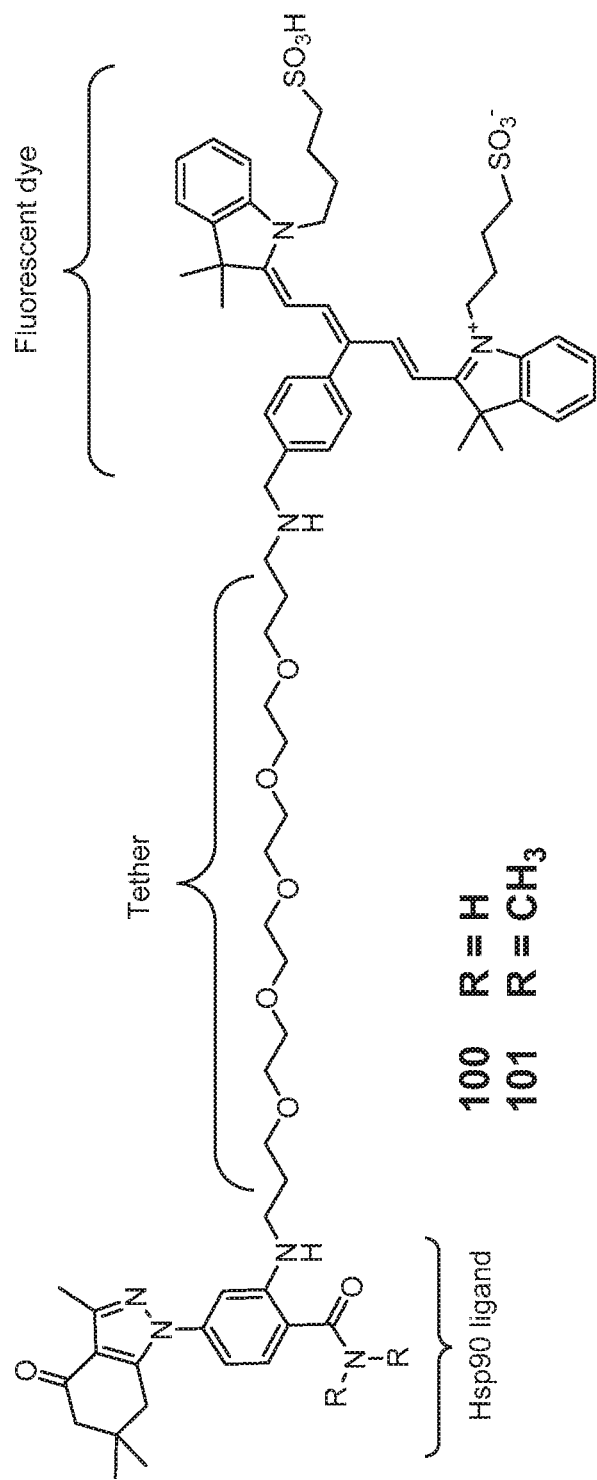
FIG. 1. 100 and 101 synthesis. (a) Structure of far-red fluorescent probes, 100 and 101. (b) Synthesis scheme of 100 and 101. (c) Simplified synthesis scheme of 101 precursor 14. See also FIG. S2.
Figure 1B:
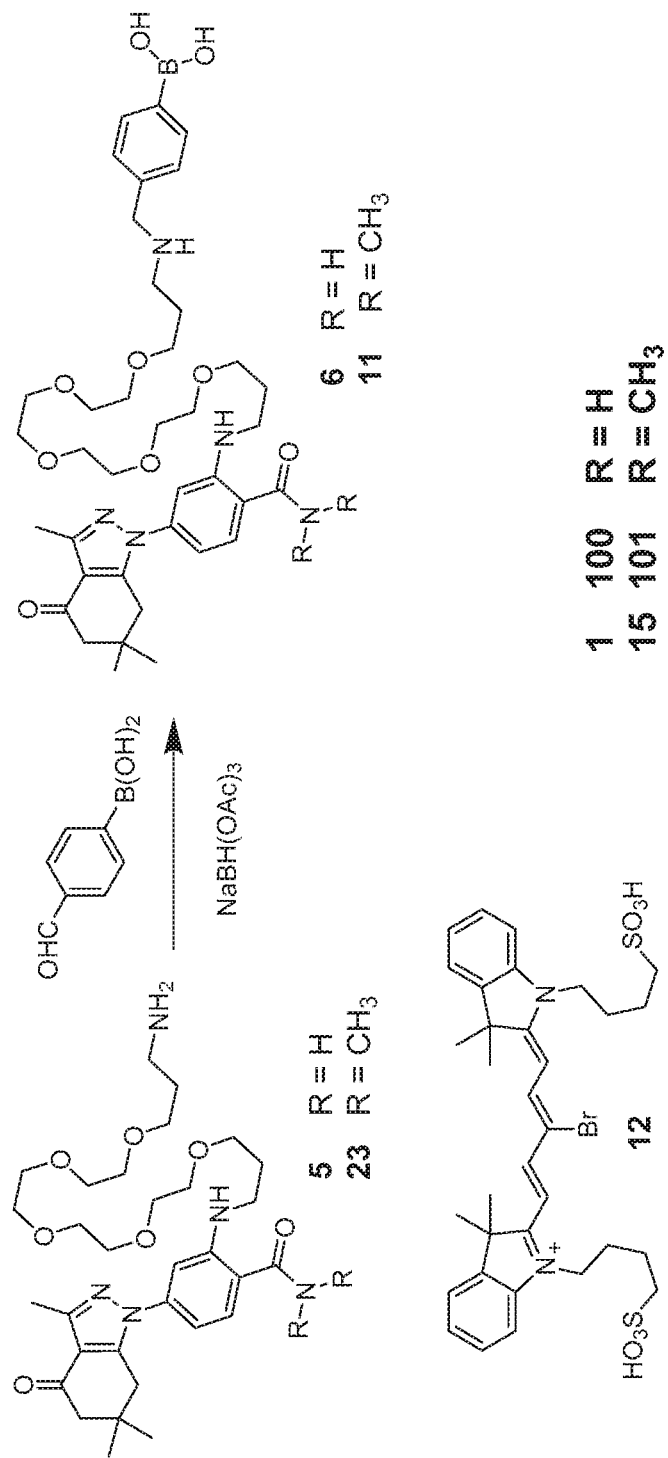
Figure 1C:
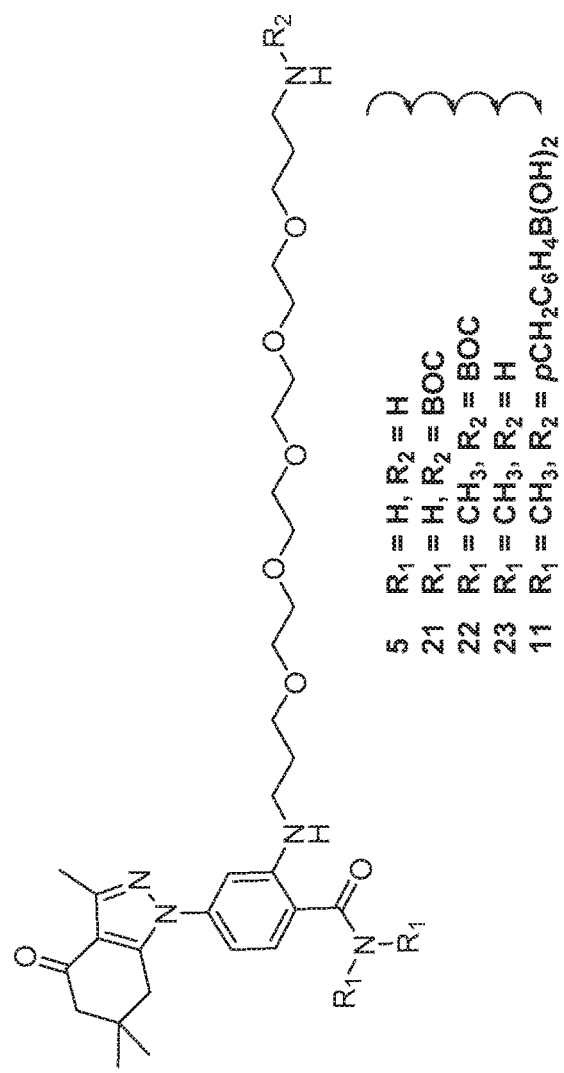

Described herein are compounds that may selectively bind to Hsp90. The compounds described herein may selectively bind to Hsp90 and may have significantly higher affinities for Hsp90 than for proteins with homology to Hsp90, such as GRP94 and TRAP1. The selective nature of the compounds may make them useful probes of Hsp90 in samples, and may allow for the selective targeting of Hsp90. For example, compounds described herein may be used to selectively detect Hsp90 in samples, and to selectively deliver anti-cancer agents to cells expressing high levels of Hsp90.

1. Definitions

The terminology used herein is for the purpose of describing particular embodiments only and is not intended to be limiting. As used in the specification and the appended claims, the singular forms "a," "and" and "the" include plural references unless the context clearly dictates otherwise.

Section headings as used in this section and the entire disclosure herein are not intended to be limiting.

For the recitation of numeric ranges herein, each intervening number there between with the same degree of precision is explicitly contemplated. For example, for the range 6-9, the numbers 7 and 8 are contemplated in addition to 6 and 9, and for the range 6.0-7.0, the numbers 6.0, 6.1, 6.2, 6.3, 6.4, 6.5, 6.6, 6.7, 6.8, 6.9 and 7.0 are explicitly contemplated.

As used herein, the term "about" is used synonymously with the term "approximately." Illustratively, the use of the term "about" indicates that values slightly outside the cited values, namely, plus or minus 10%. Such values are thus encompassed by the scope of the claims reciting the terms "about" and "approximately."

The terms "administer", "administering", "administered" or "administration" refer to any manner of providing a compound or a pharmaceutical composition (e.g., one described herein), to a subject or patient. Routes of administration can be accomplished through any means known by those skilled in the art. Such means include, but are not limited to, oral, buccal, intravenous, subcutaneous, intramuscular, transdermal, by inhalation and the like.

"Contacting" as used herein, e.g., as in "contacting a sample" refers to contacting a sample directly or indirectly in vitro, ex vivo, or in vivo (i.e. within a subject as defined herein). Contacting a sample may include addition of a compound to a sample (e.g., a sample comprising cells that contain Hsp90), or administration to a subject. Contacting encompasses administration to a solution, cell, tissue, mammal, subject, patient, or human. Further, contacting a cell includes adding an agent to a cell culture.

"Effective amount," as used herein, refers to a dosage or an amount of a compound or a composition effective for eliciting a desired effect. This term as used herein may also refer to an amount effective at bringing about a desired in vivo effect in an animal, e.g., a mammal, e.g., a human. For example, in methods of treating cancer, an effective amount may be an amount sufficient to treat the disorder.

"Member atom" as used herein refers to a polyvalent atom (e.g., a C, O, N, or S atom) in a chain or ring system that constitutes a part of the chain or ring. For example, in pyridine, five carbon atoms and one nitrogen atom are member atoms of the ring. In diethyl ether, four carbon atoms and one oxygen atom are member atoms of the chain. Member atoms will be substituted up to their normal valence. For example, in pyridine, the five carbon atoms will each be further substituted with a hydrogen or another substituent.

As used herein, the term "subject" is intended to include human and non-human animals. Exemplary human subjects include a human patient having a disorder, e.g., cancer, or a normal subject. The term "non-human animals" includes all vertebrates, e.g., non-mammals (such as chickens, amphibians, reptiles) and mammals, such as non-human primates, domesticated and/or agriculturally useful animals (such as sheep, dogs, cats, cows, pigs, etc.), and rodents (such as mice, rats, hamsters, guinea pigs, etc.).

As used herein, the term "treat" or "treating" a subject having a disorder refers to administering a compound or a composition described herein to the subject, such that at least one symptom of the disorder is cured, healed, alleviated, relieved, altered, remedied, ameliorated, or improved. Treating includes administering an amount effective to alleviate, relieve, alter, remedy, ameliorate, cure, improve or affect the disorder or the symptoms of the disorder. The treatment may inhibit deterioration or worsening of a symptom of a disorder.

Definitions of specific functional groups and chemical terms are described in more detail below. For purposes of this disclosure, the chemical elements are identified in accordance with the Periodic Table of the Elements, CAS version, Handbook of Chemistry and Physics, 75$^{th}$ Ed., inside cover, and specific functional groups are generally defined as described therein. Additionally, general principles of organic chemistry, as well as specific functional moieties and reactivity, are described in *Organic Chemistry*, Thomas Sorrell, University Science Books, Sausalito, 1999; Smith and March *March's Advanced Organic Chemistry*, 5$^{th}$ Edition, John Wiley & Sons, Inc., New York, 2001; Larock, *Comprehensive Organic Transformations*, VCH Publishers, Inc., New York, 1989; Carruthers, *Some Modern Methods of Organic Synthesis*, 3$^{rd}$ Edition, Cambridge University Press, Cambridge, 1987; the entire contents of each of which are incorporated herein by reference.

The term "acyl" refers to an alkylcarbonyl, cycloalkylcarbonyl, heterocyclylcarbonyl, arylcarbonyl or heteroarylcarbonyl substituent, any of which may be further substituted (e.g., with one or more substituents).

The term "alkyl" refers to a straight or branched saturated hydrocarbon chain. Alkyl groups may include a specified number of carbon atoms. For example, $C_1$-$C_{12}$ alkyl indicates that the alkyl group may have 1, 2, 3, 4, 5, 6, 7, 8, 9, 10, 11 or 12 carbon atoms. An alkyl group may be, e.g., a $C_1$-$C_{12}$ alkyl group, a $C_1$-$C_{10}$ alkyl group, a $C_1$-$C_8$ alkyl group, a $C_1$-$C_6$ alkyl group or a $C_1$-$C_4$ alkyl group. For example, exemplary $C_1$-$C_4$ alkyl groups include methyl, ethyl, n-propyl, isopropyl, n-butyl, sec-butyl, isobutyl and tert-butyl groups. An alkyl group may be optionally substituted with one or more substituents.

The term "alkylenyl" refers to a divalent alkyl group, examples of which include but are not limited to —$CH_2$—, —$CH_2CH_2$—, —$CH_2CH_2CH_2$— and —$CH_2CH(CH_3)CH_2$—. An alkylenyl group may be optionally substituted with one or more substituents.

The term "alkenyl" refers to a straight or branched hydrocarbon chain having one or more double bonds. Alkenyl groups may include a specified number of carbon atoms. For example, $C_2$-$C_{12}$ alkenyl indicates that the alkenyl group may have 2, 3, 4, 5, 6, 7, 8, 9, 10, 11 or 12 carbon atoms. An alkenyl group may be, e.g., a $C_2$-$C_{12}$ alkenyl group, a $C_2$-$C_1$ alkenyl group, a $C_2$-$C_8$ alkenyl group, a $C_2$-$C_6$ alkenyl group or a $C_2$-$C_4$ alkenyl group. Examples of alkenyl groups include but are not limited to allyl, propenyl, 2-butenyl, 3-hexenyl and 3-octenyl groups. One of the double bond carbons may optionally be the point of attachment of the alkenyl substituent. An alkenyl group may be optionally substituted with one or more substituents.

The term "alkenylenyl" refers to a divalent alkenyl group, examples of which include but are not limited to —CH=CH—, —CH=CH—$CH_2$—, —CH=CH—$CH_2$—$CH_2$— and —$CH_2$—CH=CH—$CH_2$—. An alkenylenyl group may be optionally substituted with one or more substituents.

The term "alkynyl" refers to a straight or branched hydrocarbon chain having one or more triple bonds. Alkynyl groups may include a specified number of carbon atoms. For example, $C_2$-$C_{12}$ alkynyl indicates that the alkynyl group may have 2, 3, 4, 5, 6, 7, 8, 9, 10, 11 or 12 carbon atoms. An alkynyl group may be, e.g., a $C_2$-$C_{12}$ alkynyl group, a $C_2$-$C_{10}$ alkynyl group, a $C_2$-$C_8$ alkynyl group, a $C_2$-$C_6$ alkynyl group or a $C_2$-$C_4$ alkynyl group. Examples of alkynyl groups include but are not limited to ethynyl, propargyl, and 3-hexynyl. One of the triple bond carbons may optionally be the point of attachment of the alkynyl substituent. An alkynyl group may be optionally substituted with one or more substituents.

The term "alkynylenyl" refers to a divalent alkynyl group, examples of which include but are not limited to —C≡C—, —C≡C—$CH_2$—, —C≡C—$CH_2$—$CH_2$— and —$CH_2$—C≡C—$CH_2$—. An alkynylenyl group may be optionally substituted with one or more substituents.

The term "aryl" refers to an aromatic monocyclic, bicyclic, or tricyclic hydrocarbon ring system, wherein any ring atom capable of substitution can be substituted (e.g., with one or more substituents). Examples of aryl moieties include but are not limited to phenyl, naphthyl, and anthracenyl. Aryl groups may be optionally substituted with one or more substituents.

The term "arylalkyl" refers to an alkyl moiety in which at least one alkyl hydrogen atom is replaced with an aryl group. Arylalkyl includes groups in which more than one hydrogen atom has been replaced with an aryl group. Examples of arylalkyl groups include but are not limited to benzyl, 2-phenylethyl, 3-phenylpropyl, 9-fluorenyl, benzhydryl, and trityl groups. Arylalkyl groups may be optionally substituted with one or more substituents, on either the aryl moiety or the alkyl moiety.

The term "cycloalkyl" as used herein refers to non-aromatic, saturated or partially unsaturated cyclic, bicyclic, tricyclic or polycyclic hydrocarbon groups having 3 to 12 carbons. Any ring atom can be substituted (e.g., with one or more substituents). Cycloalkyl groups can contain fused rings. Fused rings are rings that share one or more common carbon atoms. Examples of cycloalkyl groups include but are not limited to cyclopropyl, cyclobutyl, cyclopentyl, cyclohexyl, cyclohexenyl, cyclohexadienyl, methylcyclohexyl, adamantyl, norbornyl, norbornenyl, tetrahydronaphthalenyl and dihydroindenyl. Cycloalkyl groups may be optionally substituted with one or more substituents.

The term "cycloalkylalkyl", as used herein, refers to an alkyl group in which at least one hydrogen atom is replaced with a cycloalkyl group. Cycloalkylalkyl groups include those in which more than one hydrogen atom of the alkyl group is replaced with a cycloalkyl group. Examples of cycloalkylalkyl groups include but are not limited to cyclohexylmethyl, cyclopentylmethyl, cyclobutylmethyl and cyclopropylmethyl. Cycloalkylalkyl groups can be optionally substituted with one or more substituents, on either the cycloalkyl moiety or the alkyl moiety.

The term "halo" or "halogen" as used herein refers to any radical of fluorine, chlorine, bromine or iodine.

The term "haloalkyl" as used herein refers to an alkyl group as defined herein, in which one or more hydrogen atoms are replaced with halogen atoms, and includes alkyl moieties in which all hydrogens have been replaced with halogens (e.g., perfluoroalkyl such as $CF_3$).

"Heteroalkyl" refers to an alkyl, alkenyl or alkynyl group as defined herein, wherein at least one carbon atom of the alkyl group is replaced with a heteroatom. Heteroalkyl groups may contain from 1 to 18 non-hydrogen atoms (carbon and heteroatoms) in the chain, or 1 to 12 atoms, or 1 to 6 atoms, or 1 to 4 atoms. Heteroalkyl groups may be straight or branched, and saturated or unsaturated. Unsaturated heteroalkyl groups have one or more double bonds and/or one or more triple bonds. Heteroalkyl groups may be unsubstituted or substituted. Exemplary heteroalkyl groups include but are not limited to alkoxyalkyl (e.g., methoxymethyl), and aminoalkyl (e.g., alkylaminoalkyl and dialkylaminoalkyl). Heteroalkyl groups may be optionally substituted with one or more substituents.

The term "heteralkylenyl" refers to a divalent heteroalkyl group, examples of which include but are not limited to —$CH_2OCH_2$—, —$CH_2NHCH_2$—, polyethyleneglycol groups (e.g., —$(CH_2CH_2O)_n$—), polyethyleneimine groups (e.g., —$(CH_2CH_2NH)_n$—), and the like. A heteroalkylenyl group may be optionally substituted with one or more substituents.

The term "heteroaryl" as used herein refers to an aromatic 5-8 membered monocyclic, 8-12 membered bicyclic, or 11-14 membered tricyclic ring system having 1-3 heteroatoms if monocyclic, 1-6 heteroatoms if bicyclic, or 1-9 heteroatoms if tricyclic, said heteroatoms independently selected from O, N, S, P and Si (e.g., carbon atoms and 1-3, 1-6, or 1-9 heteroatoms independently selected from O, N, S, P and Si if monocyclic, bicyclic, or tricyclic, respectively). Any ring atom can be substituted (e.g., with one or more substituents). Heteroaryl groups can contain fused rings, which are rings that share one or more common atoms. Examples of heteroaryl groups include but are not limited to radicals of pyridine, pyrimidine, pyrazine, pyridazine, pyrrole, imidazole, pyrazole, oxazole, isoxazole, furan, thiazole, isothiazole, thiophene, quinoline, isoquinoline, quinoxaline, quinazoline, cinnoline, indole, isoindole, indolizine, indazole, benzimidazole, phthalazine, pteridine, carbazole, carboline, phenanthridine, acridine, phenanthroline, phenazine, naphthyridines and purines. Heteroaryl groups may be optionally substituted with one or more substituents.

The term "heteroarylalkyl" refers to an alkyl moiety in which at least one alkyl hydrogen atom is replaced with a heteroaryl group. Heteroarylalkyl includes groups in which more than one hydrogen atom has been replaced with a heteroaryl group. Examples of heteroarylalkyl groups include but are not limited to imidazolylmethyl (e.g., 1H-imidazol-2-ylmethyl and 1H-imidazol-4-ylmethyl), pyridinylmethyl (e.g., pyridin-3-ylmethyl and pyridin-4-ylmethyl), pyrimidinylmethyl (e.g., pyrimidin-5-ylmethyl), furylmethyl (e.g., fur-2-ylmethyl and fur-3-ylmethyl), and thienylmethyl (e.g., thien-2-ylmethyl and thien-3-ylmethyl) groups. Heteroarylalkyl groups may be optionally substituted with one or more substituents, on either the heteroaryl moiety or the alkyl moiety.

The term "heteroatom", as used herein, refers to anon-carbon or hydrogen atom such as a nitrogen, sulfur, oxygen, silicon or phosphorus atom. Groups containing more than one heteroatom may contain different heteroatoms.

The term "heterocyclyl", as used herein, refers to a nonaromatic, saturated or partially unsaturated 3-10 membered monocyclic, 8-12 membered bicyclic, or 11-14 membered tricyclic ring system having 1-3 heteroatoms if monocyclic, 1-6 heteroatoms if bicyclic, or 1-9 heteroatoms if tricyclic, said heteroatoms selected from O, N, S, Si and P (e.g., carbon atoms and 1-3, 1-6, or 1-9 heteroatoms of O, N, S, Si and P if monocyclic, bicyclic, or tricyclic, respectively). Any ring atom can be substituted (e.g., with one or more substituents). Heterocyclyl groups can contain fused rings, which are rings that share one or more common atoms. Examples of heterocyclyl groups include but are not limited to radicals of tetrahydrofuran, tetrahydrothiophene, tetrahydropyran, oxetane, piperidine, piperazine, morpholine, pyrroline, pyrimidine, pyrrolidine, indoline, tetrahydropyridine, dihydropyran, thianthrene, pyran, benzopyran, xanthene, phenoxathiin, phenothiazine, furazan, lactones, lactams such as azetidinones and pyrrolidinones, sultams, sultones, and the like. Heterocyclyl groups may be optionally substituted with one or more substituents.

The term "heterocyclylalkyl" refers to an alkyl moiety in which at least one alkyl hydrogen atom is replaced with a heterocyclyl group. Heterocyclylalkyl includes groups in which more than one hydrogen atom has been replaced with a heterocyclyl group. Examples of heterocyclylalkyl groups include but are not limited to oxetanylmethyl, morpholinomethyl, and pyrrolidinylmethyl groups, and the like. Heterocyclylalkyl groups may be optionally substituted with one or more substituents, on either the heterocyclyl moiety or the alkyl moiety.

The term "hydroxy" refers to an —OH radical. The term "alkoxy" refers to an —O— alkyl radical. The term "aryloxy" refers to an —O-aryl radical.

The term "oxo" refers to an oxygen atom, which forms a carbonyl when attached to carbon, an N-oxide when attached to nitrogen, and a sulfoxide or sulfone when attached to sulfur (i.e. =O).

The term "mercapto" or "thiol" refers to an —SH radical. The term "thioalkoxy" or "thioether" refers to an —S-alkyl radical. The term "thioaryloxy" refers to an —S-aryl radical.

The term "substituents" refers to a group "substituted" on an alkyl, alkenyl, alkynyl, cycloalkyl, heterocyclyl, aryl, arylalkyl, heteroaryl or heteroarylalkyl group at any atom of that group. Any atom can be substituted. Suitable substituents include, without limitation: acyl, acylamido, acyloxy, alkoxy, alkyl, alkenyl, alkynyl, amido, amino, carboxy, cyano, ester, halo, hydroxy, imino, nitro, oxo (e.g., C=O), phosphonate, sulfinyl, sulfonyl, sulfonate, sulfonamino, sulfonamido, thioamido, thiol, thioxo (e.g., C=S), and ureido. In embodiments, substituents on a group are independently any one single, or any combination of the aforementioned substituents. In embodiments, a substituent may itself be substituted with any one of the above substituents.

The above substituents may be abbreviated herein. For example, the abbreviations Me, Et, Ph and Bn represent methyl, ethyl, phenyl and benzyl, respectively. A more comprehensive list of standard abbreviations used by organic chemists appears in a table entitled Standard List of Abbreviations of the Journal of Organic Chemistry. The abbreviations contained in said list are hereby incorporated by reference.

For compounds described herein, groups and substituents thereof may be selected in accordance with permitted valence of the atoms and the substituents, and such that the selections and substitutions result in a stable compound, e.g., a compound that does not spontaneously undergo transformation such as by rearrangement, cyclization, elimination, etc.

Where substituent groups are specified by their conventional chemical formulae, written from left to right, they optionally encompass substituents resulting from writing the structure from right to left, e.g., —CH$_2$O— optionally also recites —OCH$_2$—.

In accordance with a convention used in the art, the group:

is used in structural formulae herein to depict the bond that is the point of attachment of the moiety or substituent to the core or backbone structure.

2. Compounds

Near IR fluorescent probes offer advantages over fluorescein for numerous reasons including greater stability, sensitivity, depth of penetration and lesser interference. A variety of agents with differing physical and spectral properties were prepared.

Compounds that may selectively bind to Hsp90 include compounds of formula (I):

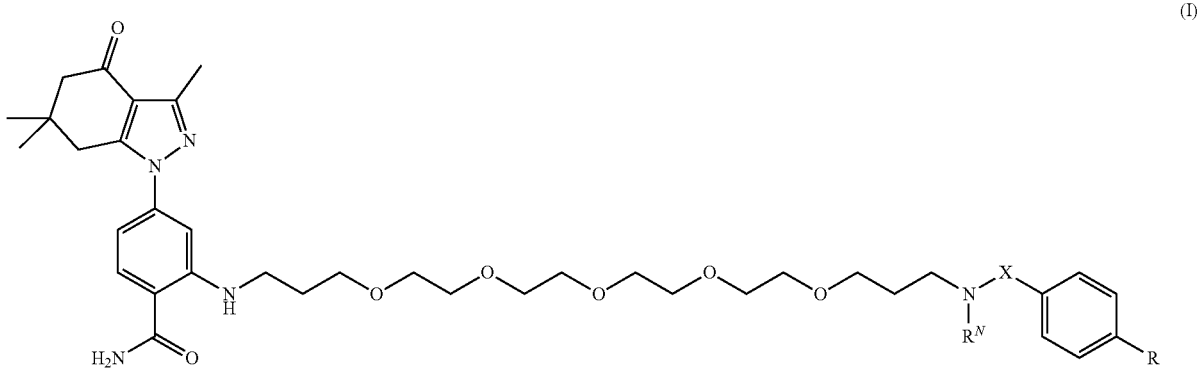

and stereoisomers and salts thereof;
wherein
X is —CH$_2$— or —C(O)—;
R$^N$ is H, —CH$_2$(C$_6$H$_4$)—I, or —CH$_2$(C$_6$H$_4$)—Sn(CH$_3$)$_3$;
R is

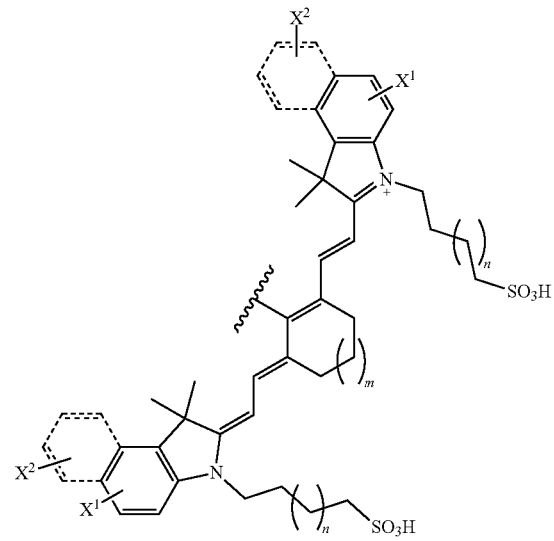

or

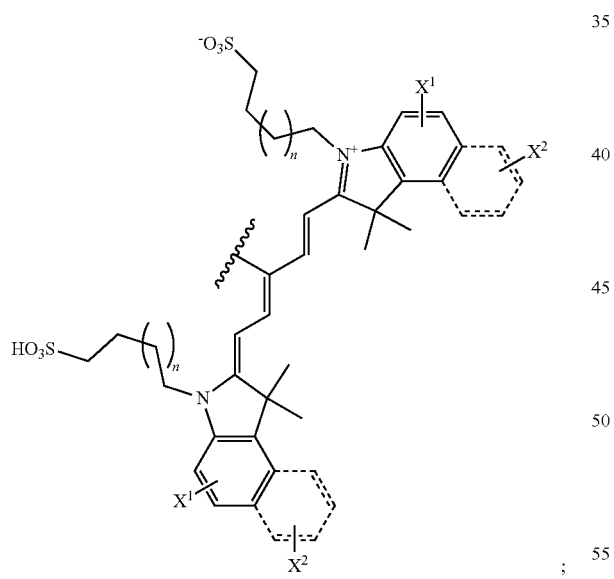

;

each X$^1$ and X$^2$, if present, are independently selected from H and SO$_3$H;
n is 0 or 1;
m=0 or 1; and
the dotted lines show an optional fused ring.
In embodiments, X is —CH$_2$—. In embodiments, X is —C(O)—. In embodiments, R$^N$ is H. In embodiments, R$^N$ is —CH$_2$(C$_6$H$_4$)—I. In embodiments, R$^N$ is —CH$_2$(C$_6$H$_4$)—Sn(CH$_3$)$_3$.

In embodiments, R is

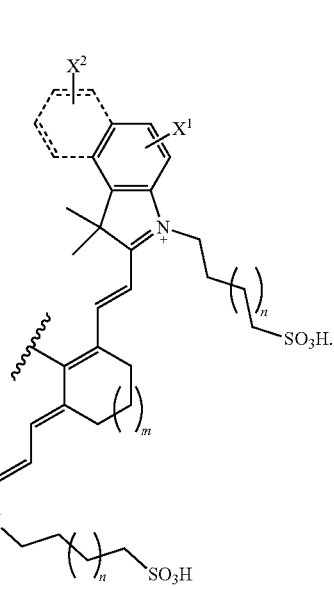

In embodiments, R is

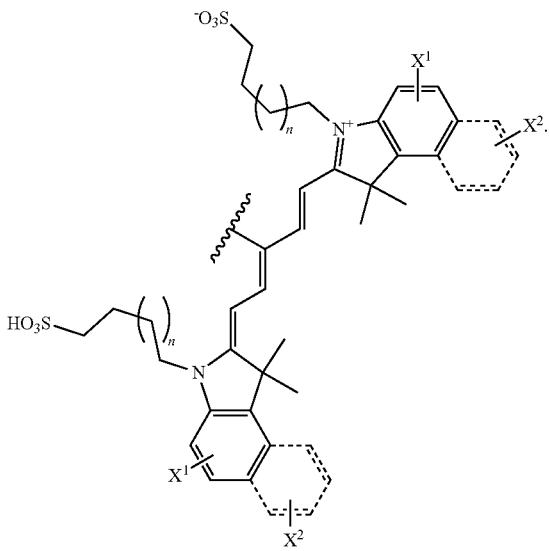

In embodiments, each $X^1$ and $X^2$, if present, are H. In embodiments, each $X^1$ is $SO_3H$. In embodiments, each $X^2$ is $SO_3H$.

In embodiments, n is 0. In embodiments, n is 1. In embodiments, m is 0. In embodiments, m is 1.

In embodiments, the iodo group may be $^{124}I$ or $^{132}I$.

Compounds according to the present disclosure include those listed in Table 1.

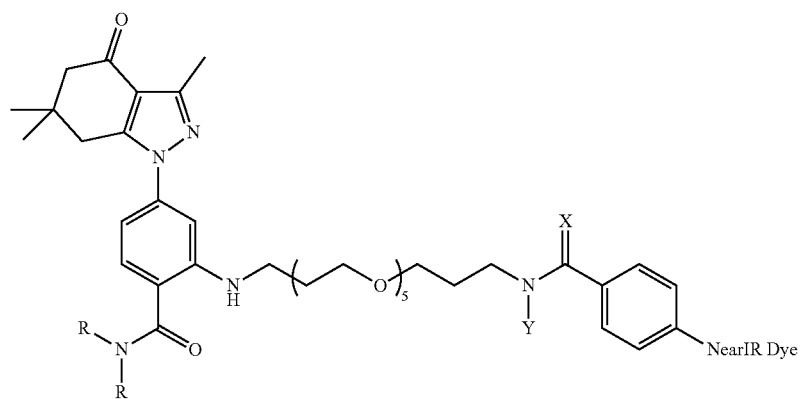

Near IR probes 100-118

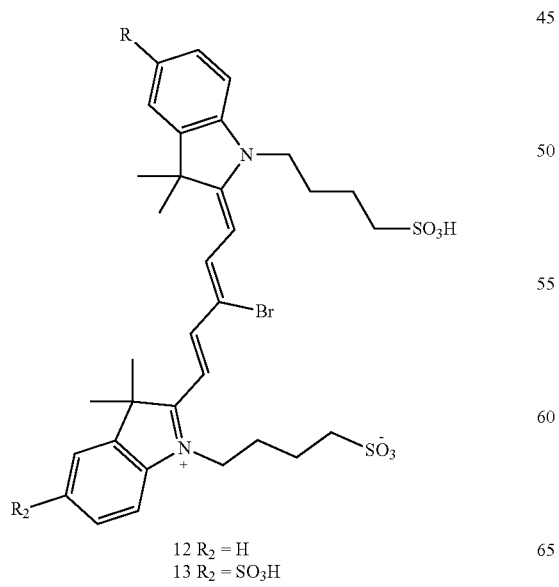

12 $R_2$ = H
13 $R_2$ = $SO_3H$

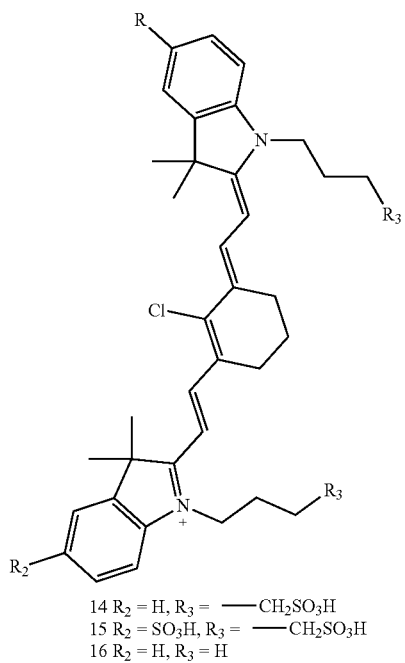

14 $R_2$ = H, $R_3$ = —$CH_2SO_3H$
15 $R_2$ = $SO_3H$, $R_3$ = —$CH_2SO_3H$
16 $R_2$ = H, $R_3$ = H

-continued

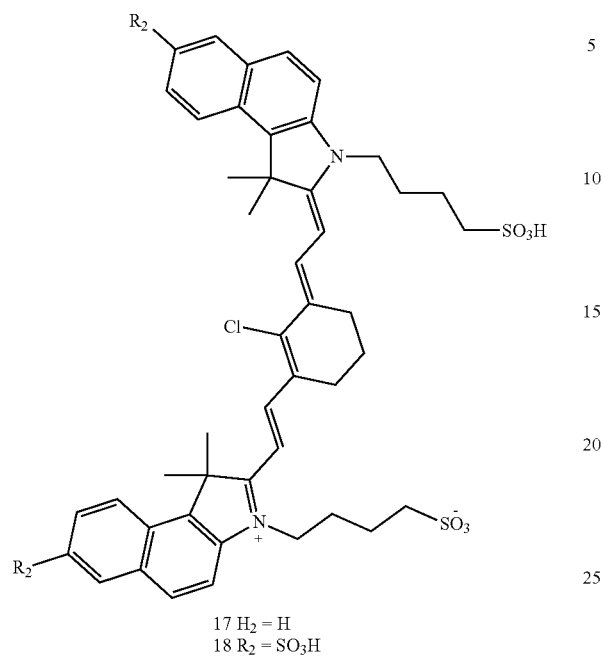

17 R$_2$ = H
18 R$_2$ = SO$_3$H

TABLE 1

Near IR fluorescent dyes synthesized using a Suzuki coupling (100-115) followed, if necessary, by alkylation (116-117) and stannylation (118).

| Probe | R$_1$ | X | Y | Abs. Max | Em. Max | Amine | Dye |
|---|---|---|---|---|---|---|---|
| 100 | H | H$_2$ | H | 644 | 672 | 6 | 12 |
| 102 | H | O | H | 643 | 670 | 7 | 12 |
| 101 | CH$_3$ | H$_2$ | H | n/d | n/d | 11 | 12 |
| 103 | H | H$_2$ | H | n/d | n/d | 6 | 13 |
| 104 | CH$_3$ | H$_2$ | H | n/d | n/d | 11 | 13 |
| 105 | H | H$_2$ | H | 766 | 796 | 6 | 14 |
| 106 | H | O | H | 766 | 795 | 7 | 14 |
| 107 | CH$_3$ | H$_2$ | H | n/d | n/d | 11 | 14 |
| 108 | H | H2 | H | 775 | 802 | 6 | 15 |
| 109 | CH$_3$ | H$_2$ | H | n/d | n/d | 11 | 15 |
| 110 | H | H$_2$ | H | n/d | n/d | 7 | 16 |
| 111 | H | H$_2$ | H | 803 | 828 | 6 | 17 |
| 112 | H | O | H | 803 | 829 | 7 | 17 |
| 113 | CH$_3$ | H$_2$ | H | n/d | n/d | 11 | 17 |
| 114 | H | H$_2$ | H | n/d | n/d | 6 | 18 |
| 115 | CH$_3$ | H$_2$ | H | n/d | n/d | 11 | 18 |
| 116 | H | H$_2$ | —CH$_2$C$_6$H$_4$—I | n/d | n/d | 6 | 12 |
| 117 | H | H$_2$ | —CH$_2$C$_6$H$_4$—I | n/d | n/d | 6 | 15 |
| 118 | H | H$_2$ | —CH$_2$C$_6$H$_4$—Sn(CH$_3$)$_3$ | | | 6 | 12 |

The present disclosure further provides a compound selected from:
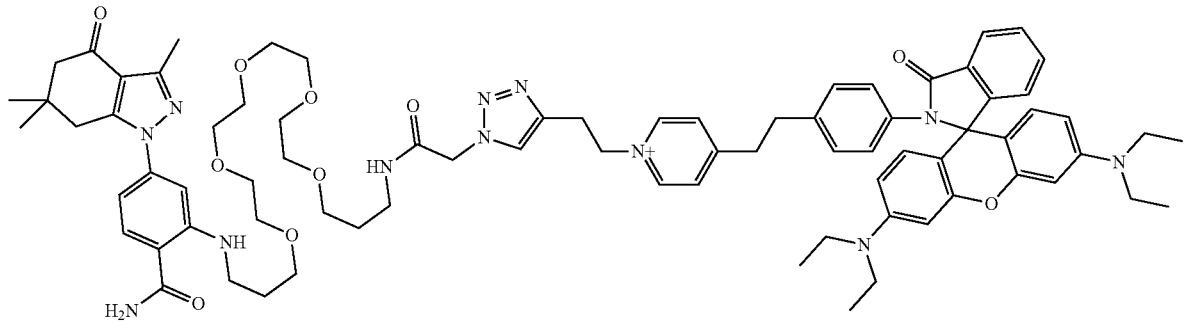
119
,
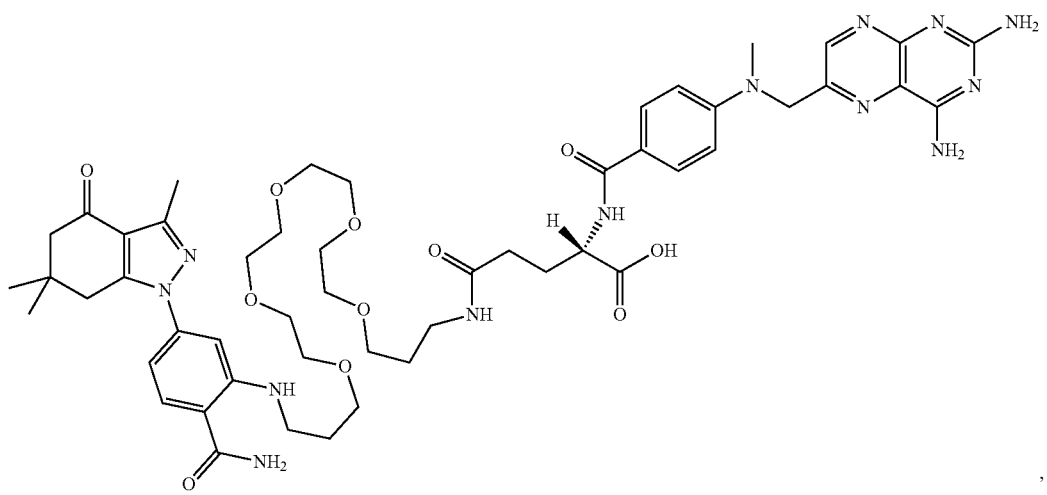
120
,
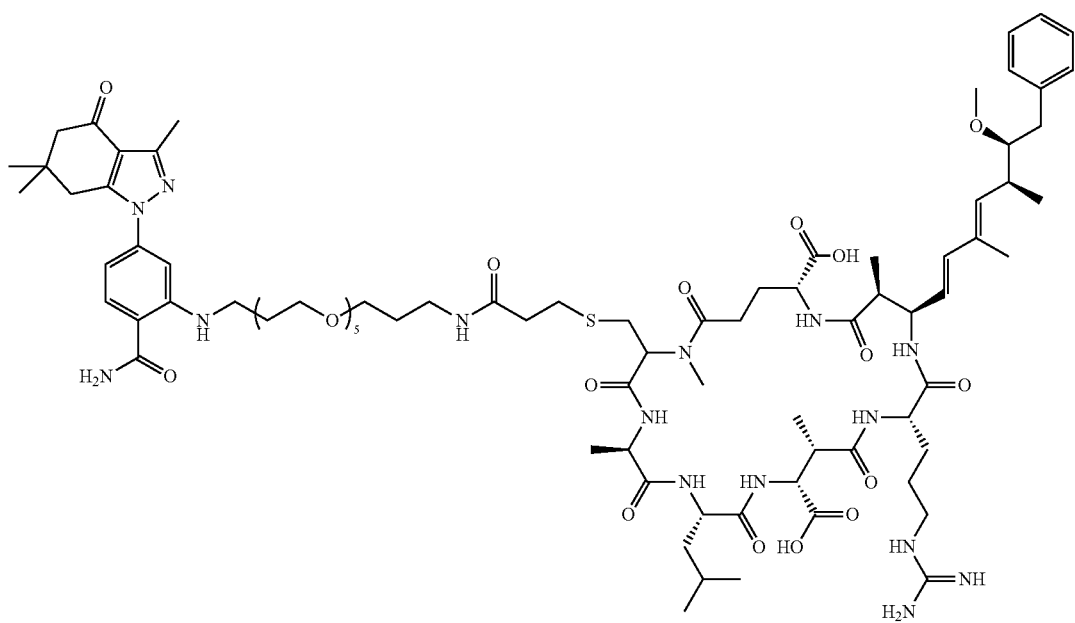
121
, and

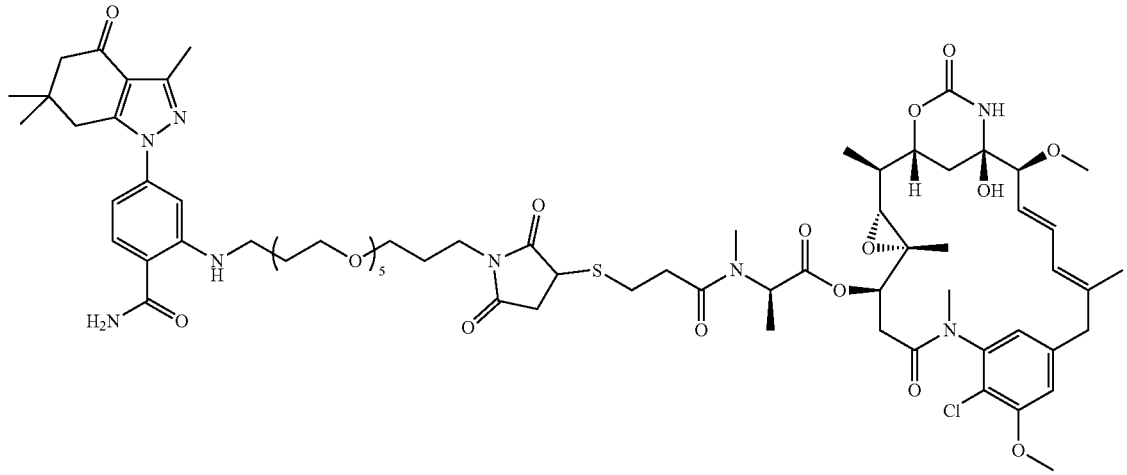

3. Preparation of Compounds

Compounds described herein may be prepared according to a variety of methods. A representative synthesis of exemplary compounds of formula (I) is illustrated in Scheme 1.

Scheme 1. Exemplary Synthesis

1)

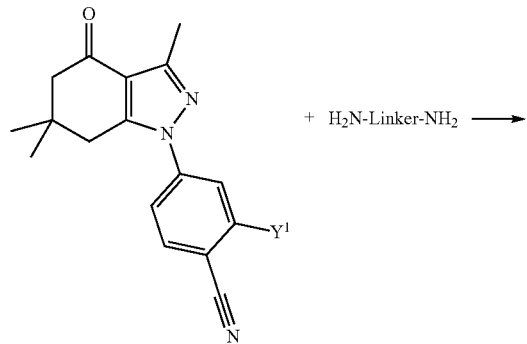

+ H$_2$N-Linker-NH$_2$ ⟶

-continued

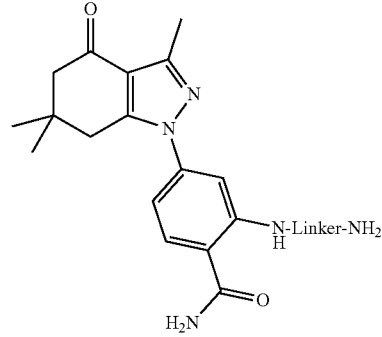

In reaction 1 of Scheme 1, the starting material includes an exemplary Hsp90-binding moiety precursor, and the group Y$^1$ is a leaving group or a reactive group. For example and as illustrated in Scheme 1, Y$^1$ may be leaving group such as a halogen, such that the compound H$_2$N-Linker-NH$_2$ may react with the compound via a reaction such as nucleophilic aromatic substitution. The nitrile can then be subsequently hydrolyzed to produce the Hsp90-binding moiety.

The general synthesis of compounds according to the present disclosure is shown in Scheme 2.

Scheme 2. General synthetic scheme for Near IR fluorescent probes.

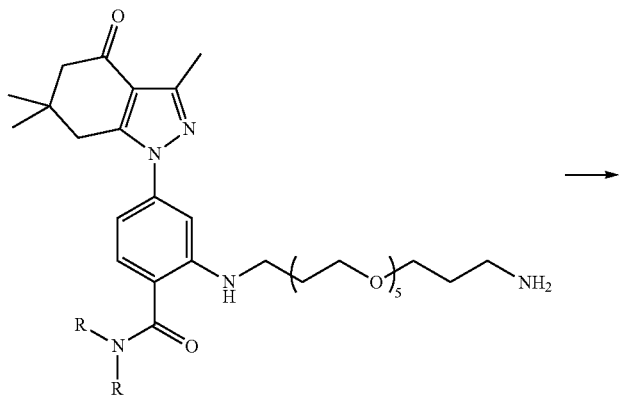

3
3 R = H
10 R = CH$_3$

-continued
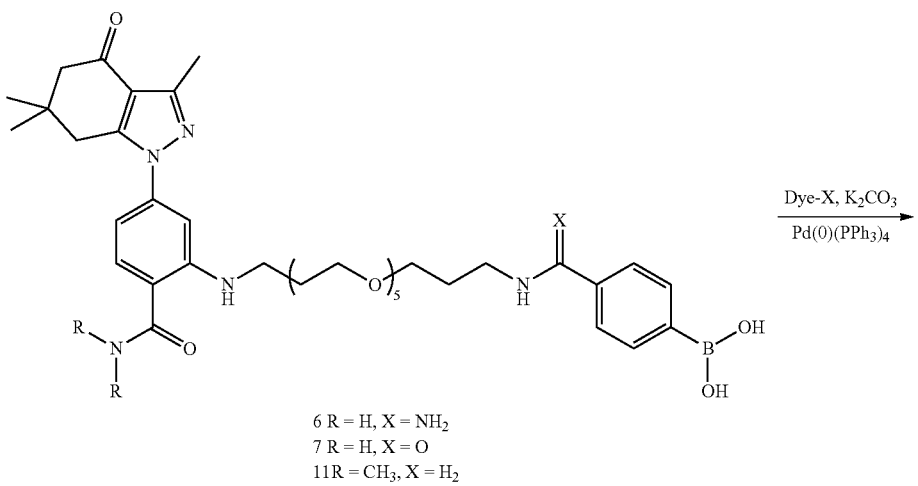
6 R = H, X = NH$_2$
7 R = H, X = O
11 R = CH$_3$, X = H$_2$
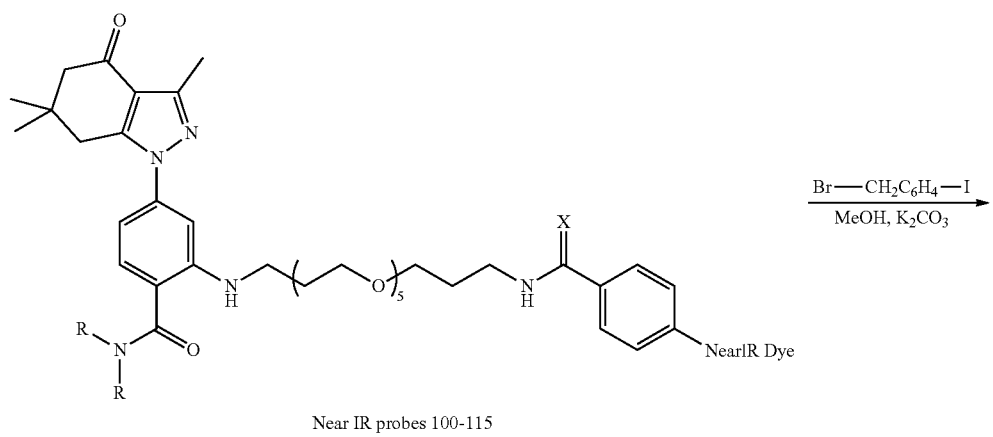
Near IR probes 100-115
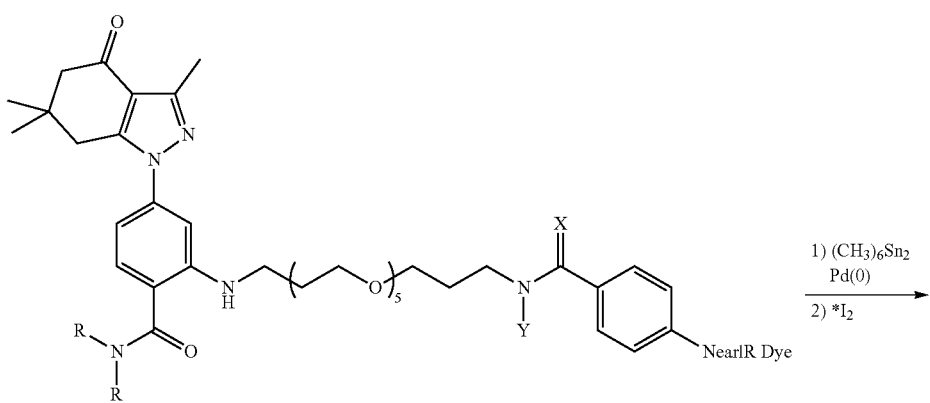
Cold iodine labelled Near IR probes 116-117

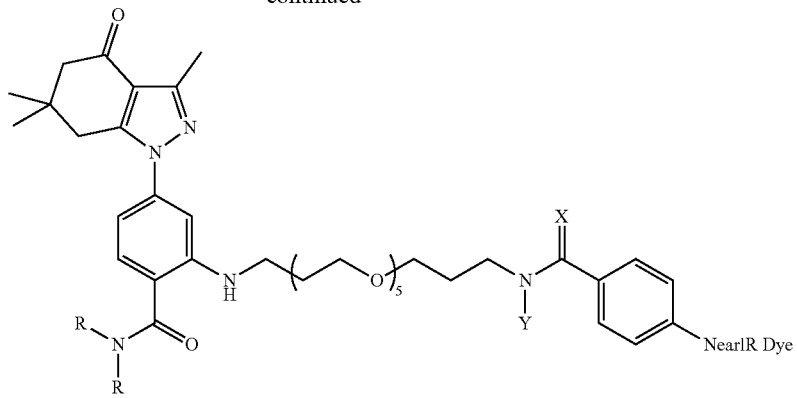

Hot iodine labelled Near IR probes 116-117

Generally, compound 3 was reacted to give a phenyl boronate by reductive amination (cpd. 6) or acylation (cpd. 7) and the product was coupled to a variety of dyes via Suzuki reaction to give the final product. To obtain non-Hsp90 binding control probes, analogs were prepared from 10, an N, N-dimethyl versions of 3. Products can be reacted with iodobenzylbromides to give iodinated probes. The cold iodides can be converted to tin analogs which can be converted back to hot iodides by standard radiochemical iodination methods.

As can be appreciated by the skilled artisan, further methods of synthesizing the compounds of the formulae herein will be evident to those of ordinary skill in the art. Additionally, the various synthetic steps may be performed in an alternate sequence or order to give the desired compounds. Synthetic chemistry transformations and protecting group methodologies (protection and deprotection) useful in synthesizing the compounds described herein are known in the art and include, for example, those such as described in R. Larock, Comprehensive Organic Transformations, VCH Publishers (1989); T. W. Greene and P. G. M. Wuts, Protective Groups in Organic Synthesis, 2d. Ed., John Wiley and Sons (1991); L. Fieser and M. Fieser, Fieser and Fieser's Reagents for Organic Synthesis, John Wiley and Sons (1994); and L. Paquette, ed., Encyclopedia of Reagents or Organic Synthesis, John Wiley and Sons (1995), and subsequent editions thereof.

3. Methods of Use

Compounds of formula (I) may be used in a variety of methods, such as methods of detecting Hsp90 in a sample, methods of detecting cancer in a subject, and methods of treating cancer in a subject.

a. Methods of Detecting Hsp90

In some embodiments, compounds described herein can be used in methods of detecting Hsp90 in a sample, the methods comprising:

a) contacting the sample with a compound as described herein; and b) detecting a signal.

In some embodiments, the sample is an in vitro sample, such as a cell or tissue extract. In some embodiments, the sample is a cell culture. For example, the sample may be a culture of cells such as cancer cells.

In some embodiments, the sample is a biological sample from a subject, such as a human. In some embodiments, the biological sample is selected from the group consisting of a tissue sample, bodily fluid, whole blood, plasma, serum, urine, bronchoalveolar lavage fluid, and a cell culture suspension or fraction thereof. In embodiments in which Hsp90 is detected in a biological sample from a subject, the methods may further involve providing or obtaining a biological sample from the subject, which can be obtained by any known means including needle stick, needle biopsy, swab, and the like. In an embodiment of such methods, the biological sample is a blood sample, such as a blood plasma or serum sample, which may be obtained by any standard technique such as, for example, by venipuncture. Biological samples used in the methods may be stored or banked under suitable tissue storage conditions, or can be accessed from samples that have been previously stored or banked under suitable conditions.

Following contacting the sample with a compound, the method further includes detecting a signal. A signal may be detected by any suitable means appropriate for the compound. For example, a signal may be detected using a fluorometer or a fluorescence plate reader, or by using fluorescence techniques such as fluorescence microscopy, fluorescence resonance energy transfer, flow cytometry and fluorescence-activated cell sorting. In embodiments, a signal may be detected using scintillation counting or radioimaging techniques. In embodiments, a signal may be detected using positron emission tomography.

A signal may be quantitated, for example, by comparing the quantity of the signal to that of a reference sample.

b. Methods of Detecting Cancer

In some embodiments, compounds described herein can be used in a method of detecting cancer in a subject, the method comprising:

a) contacting a biological sample from the subject with a compound as described herein; and b) detecting a signal;

wherein cancer is detected in the sample when the signal is higher relative to a signal from a reference sample.

In some embodiments, the method further comprises obtaining the biological sample from the subject, such as a biological sample described herein, according to methods described herein. In some embodiments, the subject is a human.

A reference sample may be a sample from a healthy subject, i.e. a subject having no clinical signs or symptoms of cancer. Suitably, the healthy subject may be clinically evaluated for otherwise undetected signs or symptoms of cancer, which evaluation may include routine physical examination and/or laboratory testing.

In embodiments, the cancer may be any type of cancer, such as a cancer recognized by the National Cancer Institute. In embodiments, the cancer may be a type of cancer associated with elevated levels of Hsp90. Exemplary types of cancers include the following:

Digestive/gastrointestinal cancers such as anal cancer; bile duct cancer; extrahepatic bile duct cancer; appendix cancer; carcinoid tumor, gastrointestinal cancer; colon cancer; colorectal cancer including childhood colorectal cancer; esophageal cancer including childhood esophageal cancer; gallbladder cancer; gastric (stomach) cancer including childhood gastric (stomach) cancer; hepatocellular (liver) cancer including adult (primary) hepatocellular (liver) cancer and childhood (primary) hepatocellular (liver) cancer; pancreatic cancer including childhood pancreatic cancer; sarcoma, rhabdomyosarcoma; islet cell pancreatic cancer; rectal cancer; and small intestine cancer;

Breast cancer, including childhood breast cancer, male breast cancer and breast cancer during pregnancy;

Genitourinary cancers such as bladder cancer including childhood bladder cancer; renal cell (kidney) cancer; ovarian cancer including childhood ovarian cancer; ovarian epithelial cancer; ovarian low malignant potential tumor; penile cancer; prostate cancer; renal cell cancer including childhood renal cell cancer; renal pelvis and ureter, transitional cell cancer; testicular cancer; urethral cancer; vaginal cancer; vulvar cancer; cervical cancer; Wilms tumor and other childhood kidney tumors; endometrial cancer; and gestational trophoblastic tumor;

Lung cancer such as non-small cell lung cancer; and small cell lung cancer;

Respiratory cancers such as malignant mesothelioma, adult; malignant mesothelioma, childhood; malignant thymoma; childhood thymoma; thymic carcinoma; bronchial adenomas/carcinoids including childhood bronchial adenomas/carcinoids; pleuropulmonary blastoma; non-small cell lung cancer; and small cell lung cancer; and Skin cancers such as Kaposi's sarcoma; Merkel cell carcinoma; melanoma; and childhood skin cancer.

In suitable embodiments, the cancer may be a cancer that is associated with increased levels of Hsp90, including but not limited to breast cancer, prostate cancer, non-small cell lung cancer, colorectal cancer, pancreatic cancer, ovarian cancer and melanoma. In particular embodiments, the cancer is breast cancer or prostate cancer.

c. Methods of Treating Cancer

In some embodiments, compounds described herein can be used in a method of treating cancer in a subject in need of treatment. Such methods comprise administering the subject a therapeutically effective amount of a compound as described herein.

In embodiments, the cancer is a cancer described herein. In embodiments, the cancer is selected from the group consisting of breast cancer, prostate cancer, non-small cell lung cancer, colorectal cancer, pancreatic cancer, ovarian cancer and melanoma. In particular embodiments, the cancer is breast cancer or prostate cancer.

In the methods of treating cancer, a compound, or a pharmaceutical composition comprising the compound, may be administered to the subject by any convenient route of administration, whether systemically/peripherally or at the site of desired action, including but not limited to, oral (e.g. by ingestion); topical (including e.g. transdermal, intranasal, ocular, buccal, and sublingual); pulmonary (e.g. by inhalation or insufflation therapy using, e.g. an aerosol, e.g. through mouth or nose); rectal; vaginal; parenteral, for example, by injection, including subcutaneous, intradermal, intramuscular, intravenous, intraarterial, intracardiac, intrathecal, intraspinal, intracapsular, subcapsular, intraorbital, intraperitoneal, intratracheal, subcuticular, intraarticular, subarachnoid, and intrasternal; by implant of a depot, for example, subcutaneously or intramuscularly. Additional modes of administration may include adding the compound and/or a composition comprising the compound to a food or beverage, including a water supply for an animal, to supply the compound as part of the animal's diet.

While it is possible for the compound to be administered alone, in some embodiments the compound may be presented as a pharmaceutical composition (e.g., formulation) comprising at least one compound, as defined above, together with one or more pharmaceutically-acceptable carriers, adjuvants, excipients, diluents, fillers, buffers, stabilizers, preservatives, lubricants, or other materials well known to those skilled in the art and optionally other therapeutic or prophylactic agents.

Thus, the disclosure further provides pharmaceutical compositions, as defined above, and methods of making a pharmaceutical composition comprising admixing at least one compound, as defined above, together with one or more pharmaceutically acceptable carriers, excipients, buffers, adjuvants, stabilizers, or other materials, as described herein.

Suitable carriers, excipients, etc. can be found in standard pharmaceutical texts, for example Remington's Pharmaceutical Sciences, 18th edition, Mack Publishing Company, Easton, Pa., 1990.

The formulations may conveniently be presented in unit dosage form and may be prepared by any method well known in the art of pharmacy. Such methods include the step of bringing into association the compound with the carrier which constitutes one or more accessory ingredients. In general, the formulations may be prepared by uniformly and intimately bringing into association the compound with liquid carriers or finely divided solid carriers or both, and then if necessary shaping the product.

Formulations may be in the form of liquids, solutions, suspensions, emulsions, elixirs, syrups, tablets, lozenges, granules, powders, capsules, cachets, pills, ampoules, suppositories, pessaries, ointments, gels, pastes, creams, sprays, mists, foams, lotions, oils, boluses, electuaries, or aerosols.

Formulations suitable for oral administration (e.g., by ingestion) may be presented as discrete units such as capsules, cachets or tablets, each containing a predetermined amount of the compound; as a powder or granules; as a solution or suspension in an aqueous or non-aqueous liquid; or as an oil-in-water liquid emulsion or a water-in-oil liquid emulsion; as a bolus; as an electuary; or as a paste.

A tablet may be made by conventional means, e.g., compression or molding, optionally with one or more accessory ingredients. Compressed tablets may be prepared by compressing in a suitable machine the compound in a free-flowing form such as a powder or granules, optionally mixed with one or more binders (e.g., povidone, gelatin, acacia, sorbitol, tragacanth, hydroxypropylmethyl cellulose); fillers or diluents (e.g., lactose, microcrystalline cellulose, calcium hydrogen phosphate); lubricants (e.g., magnesium stearate, talc, silica); disintegrants (e.g., sodium starch glycolate, cross-linked povidone, cross-linked sodium carboxymethyl cellulose); surface-active or dispersing or wetting agents (e.g., sodium lauryl sulfate); and preservatives (e.g., methyl p-hydroxybenzoate, propyl p-hydroxybenzoate, sorbic acid). Molded tablets may be made by molding in a suitable machine a mixture of the powdered compound moistened with an inert liquid diluent. The tablets may optionally be coated or scored and may be formulated so as to provide slow or controlled release of the compound therein using, for example, hydroxypropylmethyl cellulose in varying proportions to provide the desired release profile. Tablets may optionally be provided with an enteric coating, to provide release in parts of the gut other than the stomach.

Formulations suitable for topical administration (e.g., transdermal, intranasal, ocular, buccal, and sublingual) may be formulated as an ointment, cream, suspension, lotion, powder, solution, past, gel, spray, aerosol, or oil. Alternatively, a formulation may comprise a patch or a dressing such as a bandage or adhesive plaster impregnated with compounds and optionally one or more excipients or diluents. In addition, a formulation may be added to a conventional bandage, e.g. to a gauze portion that contacts a wound, as an antimicrobial agent.

Formulations suitable for topical administration in the mouth include lozenges comprising the compound in a flavored basis, usually sucrose and acacia or tragacanth; pastilles comprising the compound in an inert basis such as gelatin and glycerin, or sucrose and acacia; and mouthwashes comprising the compound in a suitable liquid carrier.

Formulations suitable for topical administration to the eye also include eye drops wherein the compound is dissolved or suspended in a suitable carrier, especially an aqueous solvent for the compound.

Formulations suitable for nasal administration, wherein the carrier is a solid, include a coarse powder having a particle size, for example, in the range of about 20 to about 500 microns which is administered in the manner in which snuff is taken, i.e., by rapid inhalation through the nasal passage from a container of the powder held close up to the nose. Suitable formulations wherein the carrier is a liquid for administration as, for example, nasal spray, nasal drops, or by aerosol administration by nebulizer, include aqueous or oily solutions of the compound.

Formulations suitable for administration by inhalation include those presented as an aerosol spray from a pressurized pack, with the use of a suitable propellant, such as dichlorodifluoromethane, trichlorofluoromethane, dichlorotetrafluoroethane, carbon dioxide, or other suitable gases.

Formulations suitable for topical administration via the skin include ointments, creams, and emulsions. When formulated in an ointment, the compound may optionally be employed with either a paraffinic or a water-miscible ointment base. Alternatively, the compounds may be formulated in a cream with an oil-in-water cream base. If desired, the aqueous phase of the cream base may include, for example, at least about 30% w/w of a polyhydric alcohol, i.e., an alcohol having two or more hydroxyl groups such as propylene glycol, butane-1,3-diol, mannitol, sorbitol, glycerol and polyethylene glycol and mixtures thereof. The topical formulations may desirably include a compound which enhances absorption or penetration of the compound through the skin or other affected areas. Examples of such dermal penetration enhancers include dimethylsulfoxide and related analogues.

When formulated as a topical emulsion, the oily phase may optionally comprise merely an emulsifier (otherwise known as an emulgent), or it may comprises a mixture of at least one emulsifier with a fat or an oil or with both a fat and an oil. Preferably, a hydrophilic emulsifier is included together with a lipophilic emulsifier which acts as a stabilizer. It is also preferred to include both an oil and a fat. Together, the emulsifier(s) with or without stabilizer(s) make up the so-called emulsifying wax, and the wax together with the oil and/or fat make up the so-called emulsifying ointment base which forms the oily dispersed phase of the cream formulations.

Suitable emulgents and emulsion stabilizers include Tween 60, Span 80, cetostearyl alcohol, myristyl alcohol, glyceryl monostearate and sodium lauryl sulfate. The choice of suitable oils or fats for the formulation is based on achieving the desired cosmetic properties, since the solubility of the compound in most oils likely to be used in pharmaceutical emulsion formulations may be very low. Thus the cream should preferably be a non-greasy, non-staining and washable product with suitable consistency to avoid leakage from tubes or other containers. Straight or branched chain, mono- or dibasic alkyl esters such as diisoadipate, isocetyl stearate, propylene glycol diester of coconut fatty acids, isopropyl myristate, decyl oleate, isopropyl palmitate, butyl stearate, 2-ethylhexyl palmitate or a blend of branched chain esters known as Crodamol CAP may be used, the last three being preferred esters. These may be used alone or in combination depending on the properties required. Alternatively, high melting point lipids such as white soft paraffin and/or liquid paraffin or other mineral oils can be used.

Formulations suitable for rectal administration may be presented as a suppository with a suitable base comprising, for example, cocoa butter or a salicylate.

Formulations suitable for vaginal administration may be presented as pessaries, tampons, creams, gels, pastes, foams or spray formulations containing in addition to the compound, such carriers as are known in the art to be appropriate.

Formulations suitable for parenteral administration (e.g., by injection, including cutaneous, subcutaneous, intramuscular, intravenous and intradermal), include aqueous and non-aqueous isotonic, pyrogen-free, sterile injection solutions which may contain anti-oxidants, buffers, preservatives, stabilizers, bacteriostats in addition to the compound, and solutes which render the formulation isotonic with the blood of the intended recipient; and aqueous and non-aqueous sterile suspensions which may include suspending agents and thickening agents, and liposomes or other microparticulate systems which are designed to target the compound to blood components or one or more organs. Examples of suitable isotonic vehicles for use in such formulations include Sodium Chloride Injection, Ringer's Solution, or Lactated Ringer's Injection. Typically, the concentration of the compound in the solution is from about 1 ng/ml to about 1 µg/ml, although other concentrations are possible and are encompassed within the invention. The formulations may be presented in unit-dose or multi-dose sealed containers, for example, ampoules and vials, and may be stored in a freeze-dried (lyophilized) condition requiring only the addition of the sterile liquid carrier, for example water for injections, immediately prior to use. Extemporaneous injection solutions and suspensions may be prepared from sterile powders, granules, and tablets. Formulations may be in the form of liposomes or other microparticulate systems which are designed to target the compound to blood components or one or more organs.

It will be appreciated that appropriate dosages of the compounds, and compositions comprising the compounds, can vary from patient to patient. Determining the optimal dosage will generally involve the balancing of the level of therapeutic benefit against any risk or deleterious side effects of the treatments of the present invention. The selected dosage level will depend on a variety of factors including, but not limited to, the activity of the particular compound, the route of administration, the time of administration, the rate of excretion of the compound, the duration of the treatment, other drugs, compounds, and/or materials used in combination, and the age, sex, weight, condition, general health, and prior medical history of the patient. The amount of compound and route of administration will ultimately be at the discretion of the physician, although generally the dosage will be to achieve local concentrations at the site of action which achieve the desired effect without causing substantial harmful or deleterious side-effects.

Administration in vivo can be effected in one dose, continuously or intermittently (e.g., in divided doses at appropriate intervals) throughout the course of treatment. Methods of determining the most effective means and dosage of administration are well known to those of skill in the art and will vary with the formulation used for therapy, the purpose of the therapy, the target cell being treated, and the subject being treated. Single or multiple administrations can be carried out with the dose level and pattern being selected by the treating physician. In general, a suitable dose of the compound is in the range of about 100 µg to about 250 mg per kilogram body weight of the subject per day.

The composition may be administered once, on a continuous basis (e.g. by an intravenous drip), or on a periodic/intermittent basis, including about once per hour, about once per two hours, about once per four hours, about once per eight hours, about once per twelve hours, about once per day, about once per two days, about once per three days, about twice per week, about once per week, and about once per month. The composition may be administered until a desired reduction of symptoms is achieved.

The present compounds, compositions, and methods may be administered as part of a therapeutic regimen along with other treatments appropriate for the particular injury or disease being treated.

4. Kits

In another aspect, the disclosure provides a kit, which may be used for detecting Hsp90 in a sample, for detecting cancer in a sample, or for treating cancer in a subject.

A kit will include a compound of formula (I) as described herein. A kit may also include instructions for use of the compound of formula (I). Instructions included in kits can be affixed to packaging material or can be included as a package insert. While the instructions are typically written or printed materials they are not limited to such. Any medium capable of storing such instructions and communicating them to an end user is contemplated by this disclosure. Such media include, but are not limited to, electronic storage media (e.g., magnetic discs, tapes, cartridges, chips), optical media (e.g., CD, DVD), and the like. As used herein, the term "instructions" can include the address of an internet site that provides the instructions.

In one embodiment, the disclosure provides a kit for detecting Hsp90 in a sample. The kit comprises at least one compound of formula (I), and instructions for assaying the test sample for Hsp90. For example, the kit can comprise instructions for assaying the test sample for Hsp90 by fluorescence detection. The kit may further comprise a calibrator or control, e.g., purified, and optionally lyophilized, (e.g., Hsp90), and/or at least one container (e.g., tube, microtiter plates or strips) for conducting the assay, and/or a buffer, such as an assay buffer or a wash buffer, either one of which can be provided as a concentrated solution. Preferably, the kit comprises all components, i.e., reagents, standards, buffers, diluents, etc., which are necessary to perform the assay. The instructions also can include instructions for generating a standard curve or a reference standard for purposes of quantifying Hsp90.

The kit can also optionally include other reagents required to conduct a diagnostic assay or facilitate quality control evaluations, such as buffers, salts, enzymes, enzyme cofactors, substrates, detection reagents, and the like. Other components, such as buffers and solutions for the isolation and/or treatment of a test sample (e.g., pretreatment reagents), also can be included in the kit. The kit can additionally include one or more other controls. One or more of the components of the kit can be lyophilized, in which case the kit can further comprise reagents suitable for the reconstitution of the lyophilized components.

The various components of the kit optionally are provided in suitable containers as necessary, e.g., a microtiter plate. The kit can further include containers for holding or storing a sample (e.g., a container or cartridge for a blood sample). Where appropriate, the kit optionally also can contain reaction vessels, mixing vessels, and other components that facilitate the preparation of reagents or the test sample. The kit can also include one or more instrument for assisting with obtaining a test sample, such as a syringe, pipette, forceps, measured spoon, or the like.

It will be readily apparent to those skilled in the art that other suitable modifications and adaptations of the compounds and methods of the present disclosure described herein are readily applicable and appreciable, and may be made using suitable equivalents without departing from the scope of the present disclosure or the aspects and embodiments disclosed herein. Having now described the present disclosure in detail, the same will be more clearly understood by reference to the following examples which are merely intended only to illustrate some aspects and embodiments of the disclosure, and should not be viewed as limiting to the scope of the disclosure. The disclosures of all journal references, U.S. patents and publications referred to herein are hereby incorporated by reference in their entireties.

EXAMPLES

General Experimental and Analytical Details

Reagents were obtained from commercial sources and used without further purification. 1,19-Diamino-4,7,10,13,16-pentaoxanonadecane was obtained from Berry and Associates. Proton NMR spectra were obtained on Varian 400 and 500 MHz spectrometers. LC/MS were obtained on an Agilent ion-trap LC/MS system. HRMS results were obtained on an Agilent 6224 LCMS-TOF and are reported as an average of four runs. Dyes were made as described or purchased.

Cell Culture and Reagents

MDA-MB-468 cells were maintained in DMEM containing 10% FBS and penicillin/streptomycin. MCF10A cells were maintained in DMEM/F-12 medium containing 5% horse serum, 100 ng/mL cholera toxin, 10 µg/mL insulin, 0.5 mg/mL hydrocortisone, 20 ng/mL EGF and penicillin/streptomycin. Doxycycline was used at a final concentration of 1 µg/mL. Cells were kept in a humidified atmosphere at 37° C. and with 5% $CO_2$. All cells were acquired from the Duke Cancer Institute Cell Culture Facility (originally obtained from ATCC: MDA-MB-468, #1619410; MCF-10A, #1566190). PUH71 was purchased from APExBIO (#A3739, Houston, Tex., USA). PitStop2 (#ab120687, Abcam, Cambridge, Mass., USA) was used at a concentration of 25 µM according to the manufacturer's instructions. All chemicals and other reagents were of analytical grade.

100 Internalization Assay and Imaging

Cells were plated on uncoated 18-mm round coverslips in 12 well plates at 150,000 cells/well and were allowed to adhere overnight. 100, in a stock solution in DMSO, was diluted in serum-free/phenol red-free DMEM. After drug incubation, the cells were washed twice with ice-cold PBS, fixed with 1% PFA in PBS for 10 min, and stained with 5 µg/mL wheat germ agglutinin-488 (WGA-488, Invitrogen, Waltham, Mass.) and either Hoescht or DAPI. The coverslips were washed and mounted onto microscope slides using FluorSave mounting reagent (Millipore, Darmstadt, Germany). Slides were imaged on a Leica SP5 confocal microscope.

Images were analyzed for fluorescence and puncta using ImageJ software using a non-biased, high-throughput macro. In brief, cells were selected using an expanded selection from the DAPI channel. The regions of interest were then masked, a watershed filter was applied to split adjacent cells into separate cells, and the regions of interest were applied to the 100 channel to measure fluorescence and puncta. High resolution confocal stacks were deconvolved with Hyugen's Deconvolution Software or AiryScan.

Hsp90 Colocalization

Cells were placed on ice for 10 min and incubated with an ice-cold solution of 100 in serum-free/phenol red-free DMEM for 30 min on ice. The cells were washed and fixed as above, blocked with 5% normal goat serum for 1 hr, and were incubated with anti-Hsp90 antibody (1:1000, sc-7947, Santa Cruz Biotechnology, Inc., Dallas, Tex., USA) for 1 hr. The coverslips were washed and incubated with secondary anti-rabbit antibody conjugated to AlexaFluor-555. The cells were washed before staining with WGA-488, mounting, and imaging.

Biotin Internalization Assay

MDA-MB-468 cells were plated $1.0 \times 10_6$ cells/well in a 6-well plate. Biotin internalization assay was performed as previously described (Gabriel et al., 2009). Lysates were collected as previously described and purified on avidin beads to collect the biotinylated proteins. The biotinylated protein fractions were subjected to Western blot analysis.

MCF10A Transformation

Human HER2 cDNAs for the full-length p185 kDa protein and its p110 kDa fragment were cloned by PCR of cDNA from the T74D cell line. PCR-based site specific mutation was performed to create a p110-kDa kinase inactivation by the K736R ATP-binding side mutation. All constructs were confirmed by sequencing. Constructs were cloned into the doxycycline-inducible expression lentivirus plasmids using a modification of a previously described method (Shin et al., 2006). For the growth foci assay, cells were trypsinized, and 1,000 cells with an inducible construct were plated with 100,000 cells uninfected MCF10A per well in a 6-well plate. Media was replaced every 3-4 days. After 3 weeks, the cells were washed, fixed with ice cold methanol, rinsed, and stained with a 0.4% methylene blue solution. The cells were rinsed several times with $diH_2O$ and were dried overnight before imaging.

Western Blot Analysis

Lysates were subjected to SDS-PAGE and were subsequently transferred to a PVDF membrane. The membrane was blocked with 5% non-fat dry milk in PBS-T (PBS with 0.1% Tween), incubated with anti-Hsp90 (1:1000, sc-7947, Santa Cruz Biotechnology, Inc., Dallas, Tex., USA), anti-HER2 (1:1000, 29D8, Cell Signaling Technology, Danvers, Mass., USA) or anti-GAPDH (1:1000, D16H11, Cell Signaling Technology, Danvers, Mass., USA) antibody for 1 hr, washed 3 times in PBS-T, incubated with anti-rabbit secondary antibody conjugated with HRP, and washed 3 times in PBS-T. The membrane was developed using Clarity Western ECL Blotting Substrate (Bio-Rad, Hercules, Calif., USA) and exposure to film.

Three-Dimensional Mouse Reconstruction

All protocols involving the use of mice were approved beforehand by the IACUC at Duke University and were strictly adhered to throughout the studies. A wild-type 3-month-old male SCID mouse with a right flank xenograft with MDA-MB-468 cells was injected with 25 nmol 100 through the tail vein. Six hours later, the mouse was euthanized, prepared according to the instructions from BioInVision, Inc. (Cleveland, Ohio, USA) and shipped for Cryo-Imaging and reconstruction. An EGFP/mCherry dual band filter set was used for imaging (#59022; Chroma Technology Corporation, Bellows Falls, Vt., USA).

Histology

MMTV-neu mice treated with 10 nmol of 100 or 101 were euthanized, and tumors, eyes, and testes were fixed in neutral-buffered formalin before dehydration and embedding in paraffin blocks. Slices of 5-µm thickness were cut and placed on slides to dry overnight. Slides were then deparaffinized and either H&E stained or rehydrated and stained with DAPI before mounting. Slides were imaged at 20× magnification on a Zeiss Axio Imager widefield fluorescence microscope equipped with a color camera.

Statistical Analysis

All imaging experiments were performed in duplicate and repeated three times. After testing for normalcy, multivariate analysis of variance (ANOVA) was used to detect significant differences between experiments with more than one factor, and univariate ANOVA was used to detect significant differences between experiments with only one factor. ANOVA results were subjected to Bonferroni post-hoc tests to account for differences in sample size. A p value of <0.05 was considered significant. All statistical analysis was performed using SPSS software version 20. Data are represented as the means±S.E.M.

Example 1. Attachment of Linker: 2-((19-Amino-4,7,10,13,16-pentaoxanonadecyl)amino)-4-(3,6,6-trimethyl-4-oxo-4,5,6,7-tetrahydro-1H-indazol-1-yl)benzamide (5)

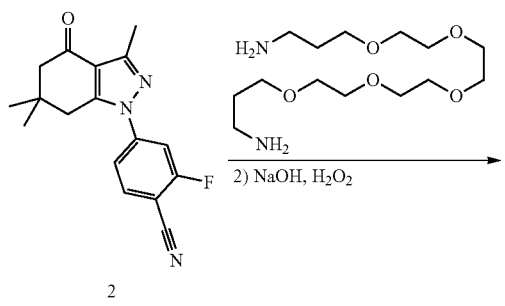

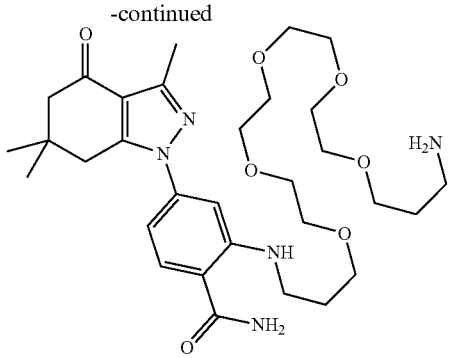

5

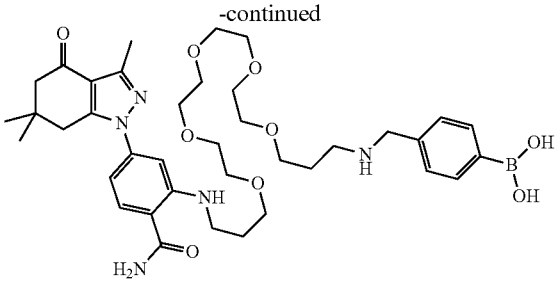

6

(4-(21((2-carbamoyl-5-(3,6,6-trimethyl-4-oxo-4,5,6,7-tetrahydro-1H-1-yl)phenyl)amino)-6,9,12,15,18-pentaoxa-2-azahenicosyl)phenyl)boronic acid (6)

A solution of amine 5 (291 mg, 482 μmop and 4-formylphenylboronic acid (74.5 mg. 496 μmop in dichloroethane (2 mL) was treated with acetic acid (30 μL) followed by solid sodium triacetoxyborohydride (235 mg, 1.1 mmol). After 1 d, the mixture was concentrated, dissolved in DMSO (1.3 mL) and water (some needed to clear solution) and purified by prep HPLC (30 to 100% methanol, 20 mL/m, Agilent C-18, 21.1×25 cm) to give 6 (233 mg. 65%) as a clear oil. $^1$H NMR (CD3OD) 8 8.5 (s, 1H formic acid), 7.74 (v br s, 2H), 7.73 (d, J=8.4 Hz, 1H), 7.44 (br d, J=8.1 Hz, 2H), 6.86 (d, J=2 Hz, 1H), 6.71 (dd, J=2, 8.4 Hz, 1H), 4.23 (s, 2H), 3.56-3.71 (m, 16H), 3.5-3.56 (m, 4H), 3.45-3.50 (m, 2H), 3.25 (t, J=6.6 Hz, 2H), 2.93 (s, 2H), 2.50 (s, 3H), 2.44 (s, 2H), 2.00 (m, 2H), 1.94 (m, 2H), 1.11 (s, 6H); 13C NMR (CDCl3) 8; 193.46, 171.63, 167.99, 150.85, 149.53, 149.09, 142.26, 129.97, 128.55, 116.93, 112.75, 108.75, 105.89, 70.33, 70.27, 70.13, 69.98, 69.67, 68.88, 68.71, 52.20, 51.01, 45.61, 39.99, 37.30, 35.64, 28.86, 28.22, 25.42, 13.27; HRMS (ESI) [M+H]+ calcd. for C38H56BN509 738.4244; found 738.4245.

A mixture of 2-fluoro-4-(3,6,6-trimethyl-4-oxo-4,5,6,7-tetrahydro-1H-indazol-1-yl)benzonitrile (2, Hughes et al, Bioorganic & medicinal chemistry 20, 3298-3305) (482 mg, 1.62 mmol) and 1,19-diamino-4,7,10,13,16-pentaoxanonadecane (1 g, 3.24 mol), diisopropylethylamine (628 mg, 4.8 mmol) and DMSO (1 mL) were heated to 90° C. for 20 m. Still at 90° C., the mixture diluted with ethanol (2 mL) and treated with 50% NaOH (10 drops) and then, very slowly, a drop at a time, with hydrogen peroxide. After each drop, the reaction foamed up substantially. After about 10 drops over 10 m, the reaction mixture was diluted with ethanol and added to silica gel (6 g) and left overnight. The next day, the slurry was concentrated to a powder, added to a silica gel column (2.5×20 cm) and chromatographed with CH$_2$Cl$_2$ (300 mL), CH$_2$Cl$_2$/MeOH/NH$_3$ 19/0.9/0.1 (300 mL), 9/0.9/0.1 (300 mL) and 4/0.9/0.1 (500 mL). Fractions containing two by-products were set aside (see below). The cleanest fractions were combined to give 5 (600 mg, 61%) as a lightly yellow glass. TLC (4/1/0.1 CH$_2$Cl$_2$/MeOH/NH$_3$) R$_f$=0.30; $^1$H NMR (CDCl$_3$) δ 7.98 (t, J=4 Hz), 7.47 (d, J=8.4 Hz, 1H), 6.77 (d, J=2 Hz, 1H), 6.60 (dd, J=2, 8.4 Hz, 1H), 6.0 (br s, 2H), 3.61 (m, 16H), 3.28 (m, 2H), 2.85 (t, 2H), 2.79 (s, 2H), 2.52 (s, 3H) 2.37 (s, 2H), 2.28 (br s, 2H), 1.94 (m, 2H), 1.76 (m, 2H), 1.07 (s, 6H); HRMS (ESI) [M+H]$^+$ calcd for C$_{31}$H$_{50}$N$_5$O$_7$, 604.3705; found 604.3715.

Example 2. Synthesis of 4-(2-((1E,3Z)-3-(4-(21-((2-carbamoyl-5-(3,6,6-trimethyl-4-oxo-4,5,6,7-tetrahydro-1H-indazol-1-yl)phenyl)amino)-6,9,12,15,18-pentaoxa-2-azahenicosyl)phenyl)-5-((Z)-3,3-dimethyl-1-(4-sulfobutyl)indolin-2-ylidene)penta-1,3-dien-1-yl)-3,3-dimethyl-3H-indol-1-ium-1-yl)butane-1-sulfonate (100)

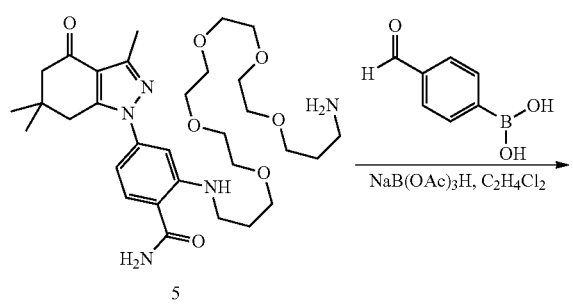

N-((1Z,3E)-2-bromo-3-(phenylimino)prop-1-en-1-yl)aniline hydrobromide (8)

Aniline (3.61 g, 38.8 mmol) was dissolved ethanol (15 mL) and cooled in an ice bath. Mucobromic acid (5 g, 19.4 mmol) in ethanol (15 mL) was added dropwise. The mixture was then heated to reflux for a 10 minutes, then allowed to cool and concentrated by about half A small aliquot was removed and plunged into water to give some solid. This was added to the salt/ice cooled reaction mixture to effect crystallization. The orange solid was filtered off and air dried to give 8 (3.11 g, 42%) as an orange powder.

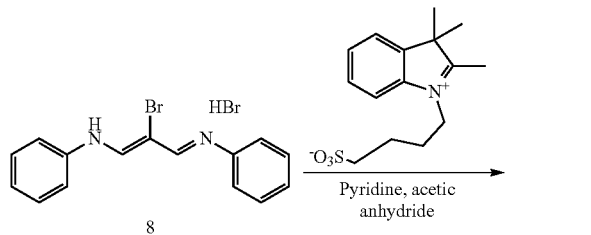

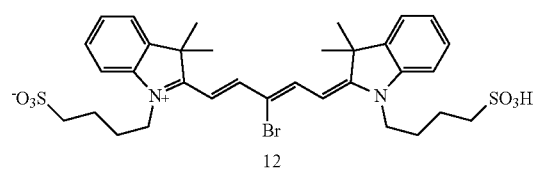

4-(2-((1E,3Z)-3-bromo-54(E)-3,3-dimethyl-1-(4-sulfobutyl)indolin-2-ylidene)penta-1,3-dien-1-yl)-3,3-dimethyl-3H-indol-1-ium-1-yl)butane-1-sulfonate (12)

N-((1Z,3E)-2-bromo-3-(phenylimino)prop-1-en-1-yl)aniline hydrobromide (8) (3 g, 7.85 mmol) and 2,3,3-Trimethyl-1-(4-sulfo-butyl)-indolium, inner salt (from Adipogen, 5.33 g, 18.2 mmol) were dissolved in pyridine (16 mL), diluted with acetic anhydride (163 mL) and heated under nitrogen to 115° C. for 2 h. The reaction mixture was concentrated then dissolved in 9/1: CH2Cl2/MeOH, added to a column and chromatographed (silica gel, 5×20 cm, CH2Cl2/MeOH: 9/1 (500 mL), 4/1 (500 mL), 3/1 (500 mL), 2/1 (500 mL) and 1/1 (1 L)). The active fractions were concentrated to give 12 (4.9 g, 96%) as a blue solid. TLC (4/0.9/0.1: CH2Cl2/MeOH/NH3) gave product with Rf=0.5. LC/MS gave a base peak at m/z=707.2. $^1$H NMR (dmso-d6) δ 8.50 (d, J=13 Hz, 2H), 7.68 (d, J=8 Hz, 2H), 7.56 (d, J=8 Hz, 2H), 7.43 (t, J=8 Hz, 2H), 7.31 (t, J=8 Hz, 2H), 6.34 (d, J=13 Hz, 2H), 4.19 (br t, 4H), 2.50 (m, 4H), 1.86 (m, 4H), 1.71 (s, 12H), 1.69 (m, 4H).

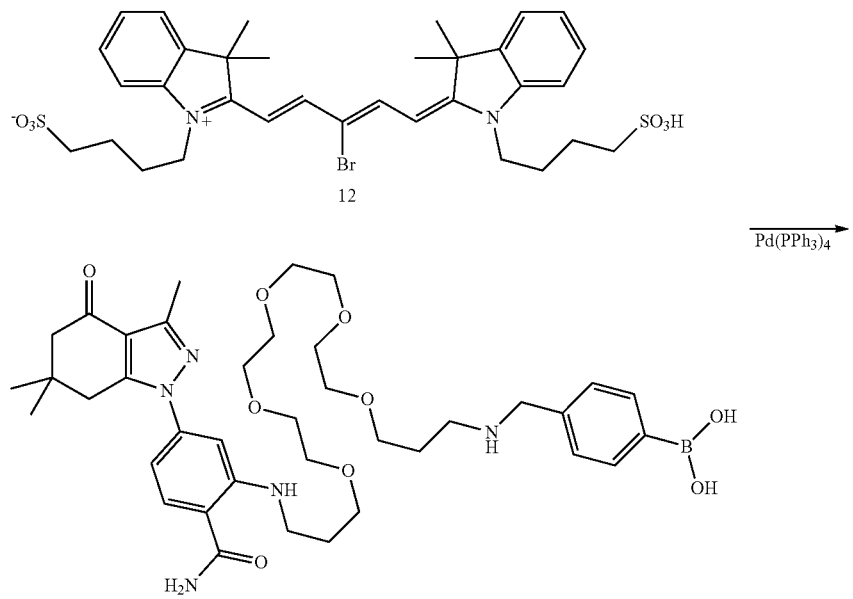

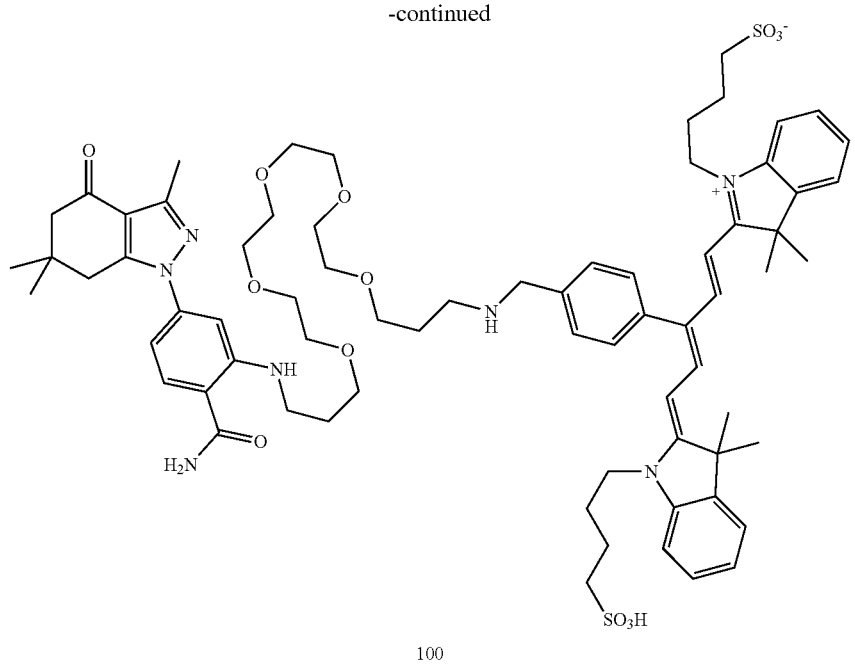

100

4-(2-((1E,3Z)-3-(4-(21-((2-carbamoyl-5-(3,6,6-trimethyl-4-oxo-4,5,6,7-tetrahydro-1H-indazol-1-yl)phenyl)amino)-6,9,12,15,18-pentaoxa-2-azahenicosyl)phenyl)-5-((Z)-3,3-dimethyl-1-(4-sulfobutyl)indolin-2-ylidene)penta-1,3-dien-1-yl)-3,3-dimethyl-3H-indol-1-ium-1-yl)butane-1-sulfonate (100)

Compound 6 (50 mg, 68 μmol), compound 12 (48 mg, 68 μmol), tetrakis (triphenylphosphine) palladium(0) (8 mg, 6.8 μmol and potassium carbonate (19 mg, 136 μmol were combined in dioxane/water (1 mL and 1 mL), bubbled with $N_2$ and heated to 100° C. After 1 h, the reaction mixture was cooled and concentrated and chromatographed (2.5×25 cm. with $CH_2Cl_2$ (25 mL), then 19/0.9/0.1, 9/0.9/0.1, 6/0.9/0.1, 4/0.9/0.1. $CH_2Cl_2$/MeOH/$NH_3$ (100 mL ea.)) to give 100 (61 mg, 68%) as a blue iridescent solid. LC/MS shows a major peak at m/z=659.9, [M+214]2+ with minor impurities. The sample was dissolved in DMSO (~1 mL) and loaded onto a Grace C-18 flash column and chromatographed (40 g column, 0 to 100% methanol over 1.5 h, 4 mL/min, 5%/5 min manual gradient) using a Waters HPLC and manual fraction collection. The blue material started moving at 65% and was fully eluted at 90%. The blue band was concentrated to give 100 (45 mg, 50%) as a blue solid. LC/MS gave a single peak with m/z=659.9, [M+21-1]$^{2+}$ NMR (dmso-$d_6$) δ 9.19 (br s, 2H), 8.48 (d, J=14 Hz, 2H), 8.41 (br t, J=5 Hz, 1H), 7.94 (br s, 1H), 7.75 (d, J=8 Hz, 1H), 7.68 (d, J=8 Hz, 2H), 7.63 (d, J=8 Hz, 2H), 7.41 (t, J=8 Hz, 2H), 7.36 (d, J=7 Hz, 2H), 7.35 (d, J=7 Hz, 2H), 7.24 (t, J=8 Hz, 2H), 6.77 (d, J=2 Hz, 1H), 6.67 (dd, J=2, 8 Hz, 1H), 5.59 (d, J=14 Hz, 2H), 4.31 (br s, 2H), 3.69 (br m, 4H), 3.56-3.46 (m, 20H), 3.2 (m, 2H), 3.07 (m, 2H), 2.92 (s, 2H), 2.39 (s, 3H), 2.32 (s, 2H), 2.27 (m, 4H), 2.02 (m, 2H), 1.80 (m, 2H), 1.73 (s, 12H), 1.51 (m, 8H), 1.01 (s, 6H).

Example 3. Synthesis of a Standard for Use with Compound 100, 4-(2-((E,3Z)-5-((E)-3,3-dimethyl-1-(4-sulfobutyl)indolin-2-ylidene)-3-(4-(((3-ethoxypropyl)amino)methyl)-phenyl)penta-1,3-dien-1-yl)-3,3-dimethyl-3H-indol-1-ium-1-yl)butane-1-sulfonate (19)

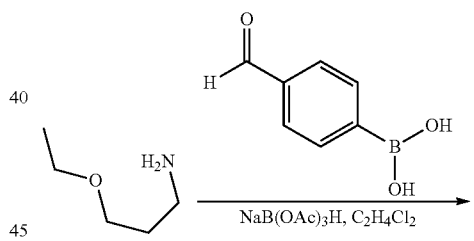

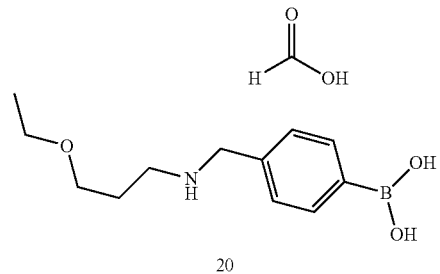

20

(4-(((3-ethoxypropyl)amino)methyl)phenyl)boronic acid (20).

A solution of 4-formylphenylboronic acid (250 mg, 1.7 μmol) and 4-3-ethoxypropylamine (344 mg. 3.3 mmol) in dichloroethane (4 mL) was treated with acetic acid (95 μL) followed by solid sodium triacetoxyborohydride (706 mg, 3.3 mmol). After one day, the reaction mixture was concentrated, dissolved in DMSO and purified by prep HPLC (0. to 100% methanol w/0.2% formic acid, 20 mL/m, Agilent C-18, 21.1×25 cm). The product was concentrated to give 20 (407 mg, 86% as a formate) as a clear oil. LC/MS gave a single peak with m/z=238.2, [M+1]+.

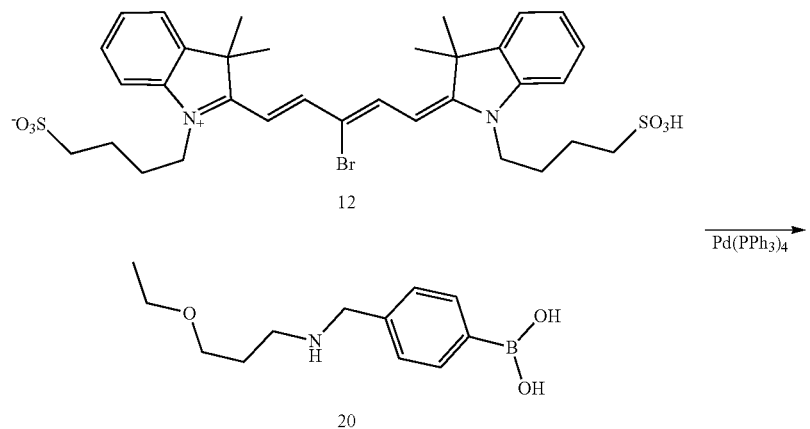

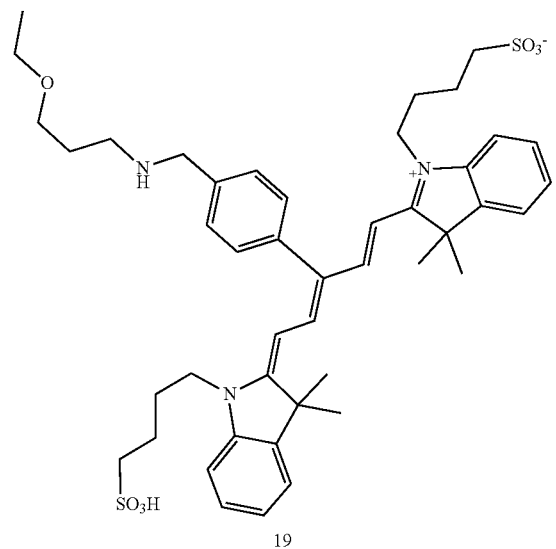

4-(2-(((1E,3Z)-5-((E)-3,3-dimethyl-1-(4-sulfobutyl) indolin-2-ylidene)-3-(4-(((3-ethoxypropyl)amino) methyl)phenyl)penta-1,3-dien-1-yl)-3,3-dimethyl-3H-indol-1-ium-1-yl)butane-1-sulfonate (19)

Borate 20 (formate salt, 30 mg, 105 μmol), Cy5 dye 12 (37 mg, 52 μmol), tetrakis(triphenylphosphine)palladium(0) (3.7 mg, 3.2 μmol) and potassium carbonate (14 mg, 100 μmol) were combined in dioxane/water (1 mL and 1 mL), bubbled with $N_2$ and heated to 100° C. After 1.5 h, the reaction mixture was concentrated and chromatographed (silica gel, 0 to 20% 9/1:MeOH/NH4OH in CH2Cl2 gradient) to give 19 (15 mg, 35%) as a deep blue solid. LC/MS gave a single peak with m/z=818.4, [M+1]+.

Example 4. Synthesis of Standard for Use with Compound 100, 4-(2-(((1E,3Z)-5-((E)-3,3-dimethyl-1-(4-sulfobutyl)indolin-2-ylidene)-3-(4-(21-((2-(dimethylcarbamoyl)-5-(3,6,6-trimethyl-4-oxo-4,5,6,7-tetrahydro-1H-indazol-1-yl)phenyl)amino)-6,9,12,15,18-pentaoxa-2-azahenicosyl)phenyl)penta-1,3-dien-1-yl)-3,3-dimethyl-3H-indol-1-ium-1-yl) butane-1-sulfonate (101)

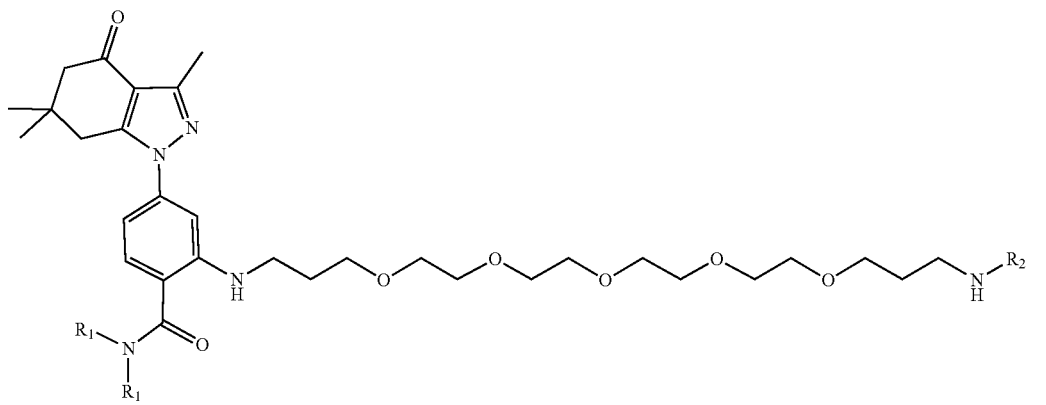

5   $R_1$ = H, $R_2$ = H
21  $R_1$ = H, $R_2$ = BOC
22  $R_1$ = CH₃, $R_2$ = BOC
23  $R_1$ = CH₃, $R_2$ = H
11  $R_1$ = CH₃, $R_2$ = pCH₂C₆H₄B(OH)₂

12, Pd(PPh₃)₄

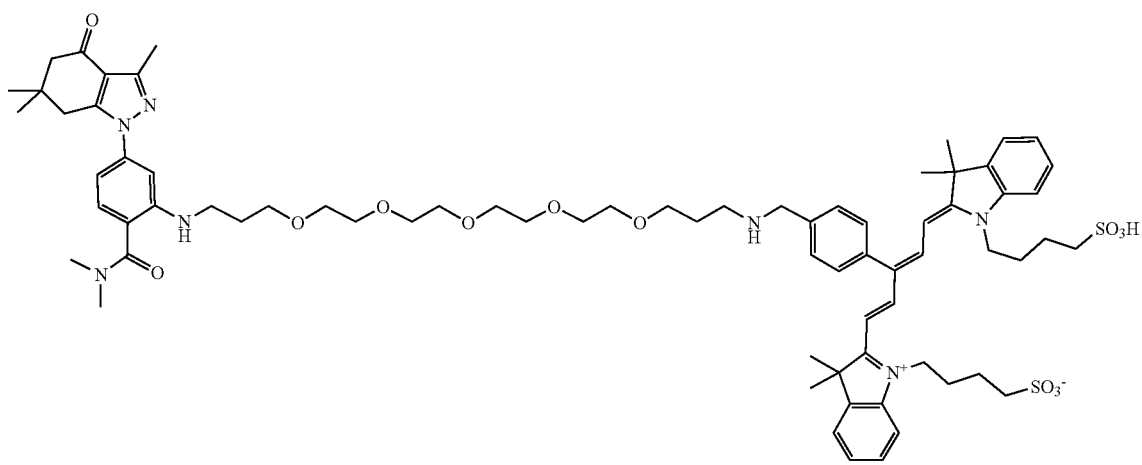

101 tert-Butyl (19-((2-carbamoyl-5-(3,6,6-trimethyl-4-oxo-4,5,6,7-tetrahydro-1H-indazol-1-yl)phenyl)amino)-4,7,10,13,16-pentaoxanonadecyl)carbamate (21)

Amine 5 was dissolved in methylene chloride (50 mL) and treated with BOCOBOC (940 mg, 1.04 mL, 4.5 mmol). After 30 minutes the reaction mixture was concentrated and chromatographed (silica gel, 0 to 2.5% MeOH in $CH_2Cl_2$) to give the product 21 (1.52 g, 50%) as a clear viscous oil. LC/MS gave a single peak with m/z=704.4, $^1$HNMR (dmso-$d_6$) δ 8.41 (br t, J=6 Hz, 1H), 7.92 (br s, 1H), 7.74 (d, J=8 Hz, 1H), 7.27 (br s, 1H) 6.77 (d, J=2 Hz, 1H), 6.75 (br t, J=6 Hz, 1H), 6.68 (dd, J=2, 8 Hz, 1H), 3.46-5.53 (m, 18H), 3.44 (m, 2H), 3.35 (t, J=6 Hz, 2H), 3.2 (q, J=6 Hz, 2H), 2.94 (q, J=6 Hz, 2H), 2.92 (s, 2H), 2.40 (s, 3H), 2.33 (s, 2H), 1.81 (p, J=6 Hz, 2H), 1.57 (p, J=6 Hz, 2H), 1.36 (s, 9H), 1.01 (s, 6H).

tert-butyl (19-((2-(dimethylcarbamoyl)-5-(3,6,6-trimethyl-4-oxo-4,5,6,7-tetrahydro-1H-indazol-1-yl)phenyl)amino)-4,7,10,13,16-pentaoxanonadecyl)carbamate (22)

BOCamide 21 (893 mg, 1.27 mmol) was dissolved in THF (20 mL) and treated with potassium t-butoxide (142 mg, 1.27 mL of IN solution in THF, 1.27 mmol) followed by slow addition of methyl iodide (180 mg, 79 µL, 1.27 mmol). After 1 h, the reaction mixture was again treated with potassium t-butoxide (142 mg, 1.27 mL of TN solution in THF, 1.27 mmol) followed by slow addition of methyl iodide (180 mg, 79 µl, 27 mmol). After an hour, the entire reaction mixture was added to silica gel (7 g) and concentrated and flashed (silica gel, 0 to 30% MeOH in EtOAc) to give 22 (397 mg, 43%) as a viscous yellow oil. LC/MS gave a single peak (>95%) with m/z=732.5. $^1$H NMR (dmso-$d_6$) δ 7.17 (d, J=8 Hz, 1H), 6.77 (d, J=2 Hz, 1H), 6.75 (br t, 1H), 6.73 (dd, J=2, 8 Hz, 1H), 5.67 (br t, J=6 Hz, 1H), 3.46-3.53 (m, 18H), 3.44 (m, 2H), 3.36 (t, J=6 Hz, 2H), 3.18 (q, J=6 Hz, 2H), 2.95 (br s, 6H), (2.94 (q, J=6 Hz, 2H), 2.90 (s, 2H), 2.39 (s, 3H), 2.33 (s, 2H), 1.78 (p, J=6 Hz, 2H), 1.58 (p, J=6 Hz, 2H), 1.36 (s, 9H), 1.02 (s, 6H).

2-((19-amino-4,7,10,13,16-pentaoxanonadecyl)amino)-N,N-dimethyl-4-(3,6,6-trimethyl-4-oxo-4,5,6,7-tetrahydro-1H-indazol-1-yl)benzamide (23)

BOCamide 22 (332 mg, 453 µmol) was treated with TFA (1 mL) in $CH_2Cl_2$ (3 mL). This sample was concentrated and purified by prep HPLC (0 to 100% methanol, 20 mL/m, Agilent C-18, 21.1×25 cm) to give 23 (137 mg, 47%) as a clear oil. LC/MS gave a single peak with m/z=632.4

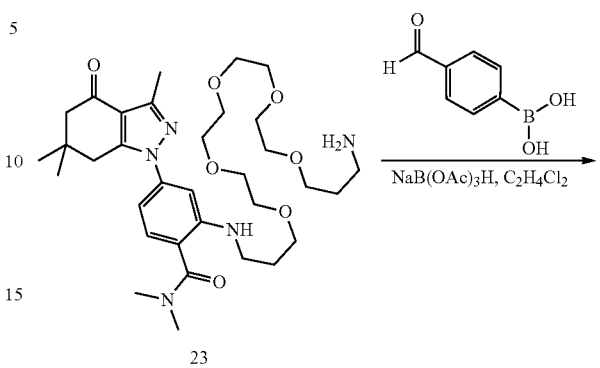

(4-(21-((2-(dimethylcarbamoyl)-5-(3,6,6-trimethyl-4-oxo-4,5,6,7-tetrahydro-1H-indazol-1-yl)phenyl)amino)-6,9,12,15,18-pentaoxa-2-azahenicosyl)phenyl)boronic acid (11)

Amine 23 (137 mg, 217 µmol), 4-formylphenylboronic acid (65 mg, 434 limo'), and acetic acid (25 µL), were dissolved in 1/1: MeOH/CH2Cl2 (2 mL) and concentrated. The glassy residue was dissolved in methylene chloride (2 mL) and treated with again with acetic acid followed by solid sodium triacetoxyborohydride (114 mg, 542 µmop. After 2 h, the mixture was treated with MeOH to stop reaction and stirred overnight. The reaction mixture was chromatographed by prep HPLC (0 to 100% methanol, 20 mL/m, Agilent C-18, 21.1×25 cm) to give pure borate 11 (114 mg, 71%) as a clear glass. LC/MS gave a single peak with m/z=766.4 [M+]$^+$.

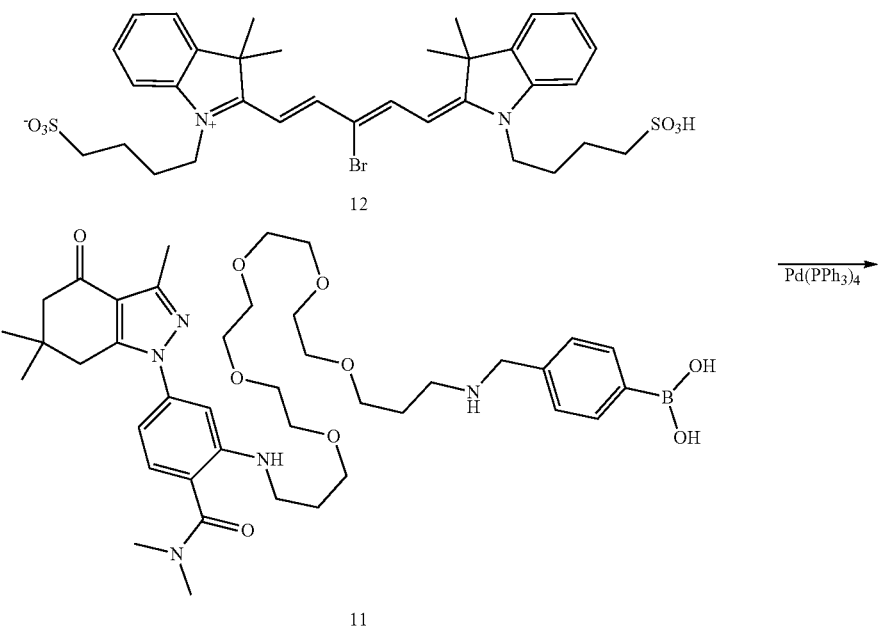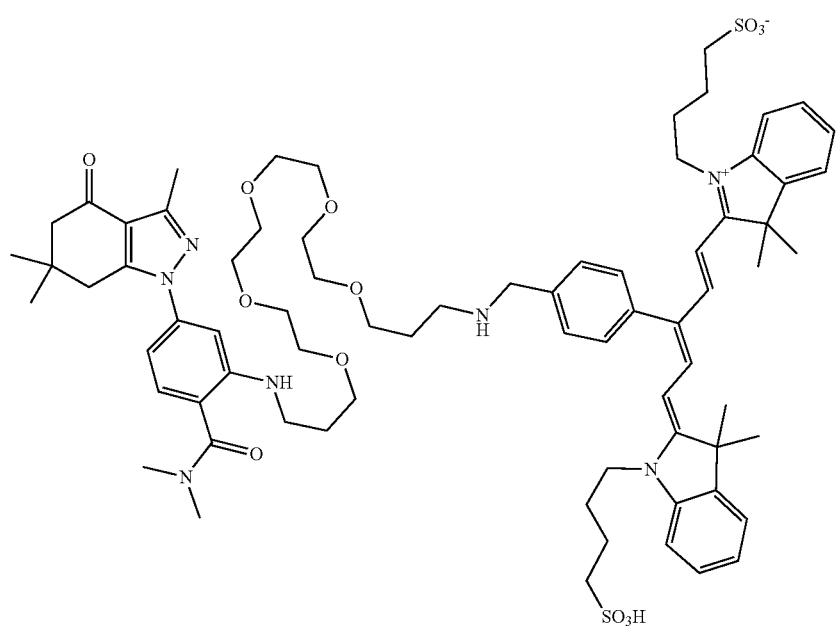

4-(2-((1E,3Z)-5-((E)-3,3-dimethyl-1-(4-sulfobutyl)
indolin-2-ylidene)-3-(4-(21-((2-(dimethylcarbam-
oyl)-5-(3,6,6-trimethyl-4-oxo-4,5,6,7-tetrahydro-1H-
indazol-1-yl)phenyl)amino)-6,9,12,15,18-pentaoxa-
2-azahenicosyl)phenyl)penta-1,3-dien-1-yl)-3,3-
dimethyl-3H-indol-1-ium-1-yl)butane-1-sulfonate
(101)

Compound 11 (52 mg, 68 μmol), compound 12 (48 mg, 68 μmol), tetrakis(triphenylphosphine)palladium(0) (8 mg, 6.8 μmol) and potassium carbonate (19 mg, 136 μmol) were combined in dioxane/water (1 mL each), bubbled with $N_2$ and heated to 100° C. for 1 hour. The reaction mixture was then concentrated, dissolved in DMSO and chromatographed by prep HPLC (0 to 100% methanol, 20 mL/m, Agilent C-18, 21.1×25 cm). The product was concentrated then concentrated twice from methanol to give 101 (49.2 mg, 54%) as a dark blue solid. LC/MS shows a 95+% peak with m/z=1346.6 [M+1]$^+$.

Example 5. Synthesis of 4-(2-((E,3Z)-3-(4-((19-((2-
carbamoyl-5-(3,6,6-trimethyl-4-oxo-4,5,6,7-tetra-
hydro-1H-indazol-1-yl)phenyl)amino)-4,7,10,13,16-
pentaoxanonadecyl)carbamoyl)phenyl)-5-((E)-3,3-
dimethyl-1-(4-sulfobutyl)indolin-2-ylidene)penta-1,
3-dien-1-yl)-3,3-dimethyl-3H-indol-1-ium-1-yl)
butane-1-sulfonate (102)

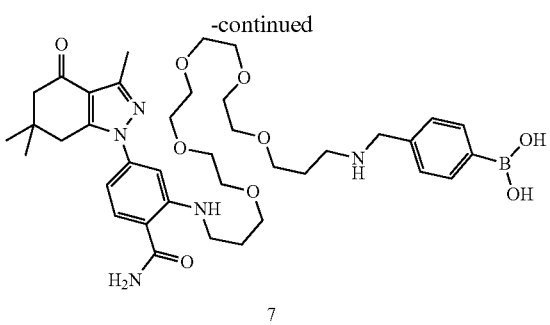

(4-((19-((2-carbamoyl-5-(3,6,6-trimethyl-4-oxo-4,5,
6,7-tetrahydro-1H-indazol-1-yl)phenyl)amino)-4,7,
10,13,16-pentaoxanonadecyl)carbamoyl)phenyl)
boronic acid (7)

A solution of amine 5 (342 mg, 567 μmol), 4-carboxyphenylboronic acid (103 mg, 623 μmol), Hunig's base (146 mg, 1.13 mmol), HOBT (77 mg, 567 μmol) and DMAP (7 mg, 737 μmol) were dissolved in methylene chloride (3 mL) and then treated with solid EDC (141 mg, 567 μmol) and stirred overnight. The mixture was then concentrated, dissolved in DMSO (2 mL) and purified by preparative HPLC (Agilent C-18, 21.1×25 cm, 0 to 100% methanol, 0.2% formic, 20 mL/m) to give 7 (306 mg, 72%) as a clear glass. H NMR (CD$_3$OD) δ 8.5 (s, 1H formic acid), 7.76 (v br s, 4H), 7.70 (d, J=8.4 Hz, 1H), 6.83 (d, J=2 Hz, 1H), 6.67 (dd, J=2, 8.4 Hz, 1H), 3.51-3.64 (m, 20H), 3.46 (t, J=7.0 Hz, 2H), 3.29 (m, 2H), 2.90 (s, 2H), 2.50 (s, 3H), 2.39 (s, 2H), 1.90 (m, 2H), 1.86 (m, 2H), 1.07 (s, 6H). $^{13}$C NMR (CD$_3$OD) δ; 196.78, 174.5, 152.97, 152.42, 151.61, 144.13, 135.62, 132.24, 128.05, 118.66, 115.55, 110.97, 108.03, 72.33, 72.3, 72.28, 72.13, 72.06, 71.1, 70.53, 53.9, 41.73, 39.7, 39.58, 38.84, 37.57, 31.19, 31.09, 29.28, 14.28. HRMS (ESI) [M+H]$^+$ calcd for $C_{38}H_{54}BN_5O_{10}$ 752.4036; found 752.4034.

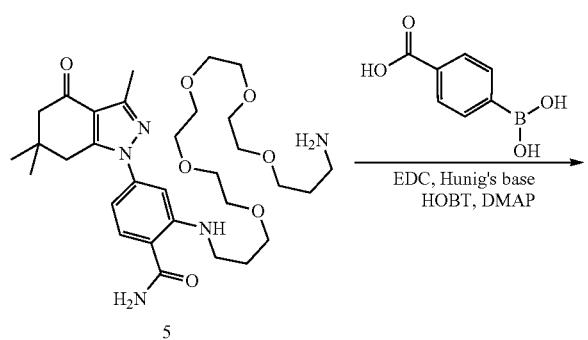

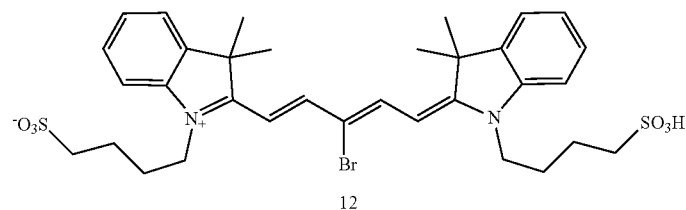

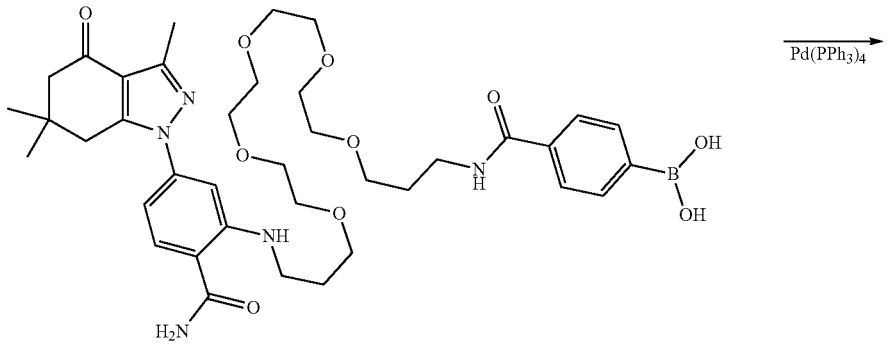

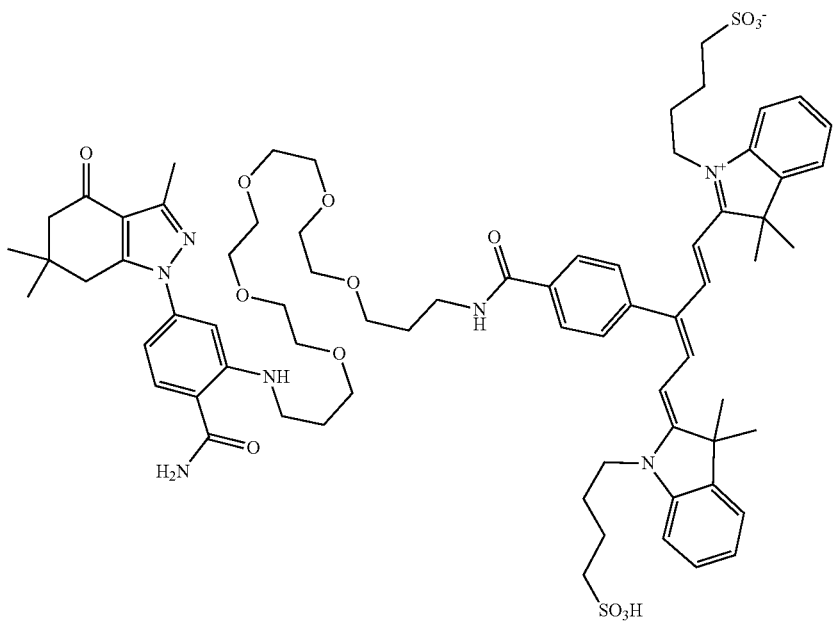

102

4-(2-((1E,3Z)-3-(4-((19-((2-carbamoyl-5-(3,6,6-trimethyl-4-oxo-4,5,6,7-tetrahydro-1H-indazol-1-yl)phenyl)amino)-4,7,10,13,16-pentaoxanonadecyl)carbamoyl)phenyl)-5-((E)-3,3-dimethyl-1-(4-sulfobutyl)indolin-2-ylidene)penta-1,3-dien-1-yl)-3,3-dimethyl-3H-indol-1-ium-1-yl)butane-1-sulfonate (102)

Boronic acid 7 (51 mg, 68 μmol), dye 12 (48 mg, 68 μmol), tetrakis(triphenylphosphine) palladium(0) (8 mg, 6.8 μmol) and potassium carbonate (19 mg, 136 μmol) were combined in dioxane/water (1 mL and 1 mL), bubbled with $N_2$ and heated to 100° C. After 1 h, TLC (4/0.9/0.1: $CH_2Cl_2$/MeOH/$NH_4OH$) showed a new product. The mixture cooled, concentrated and chromatographed (silica gel, 2.5× 25 cm. with $CH_2Cl_2$ (25 mL), then 19/0.9/0.1 (100 mL), 9/0.9/0.1, 7/0.9/0.1, (200 mL ea.): $CH_2Cl_2$/MeOH/$NH_3$) to give 102 (28 mg, 31%) as a blue indescent solid. LC/MS gave a single peak with m/z=666.9 $[M+2]^{2+}$. $^1$H-NMR (DMSO-$d_6$) δ 8.91 (br t, J=6 Hz, 1H), 8.46 (d, J=14 Hz, 2H), 8.41 (br t, J=6 Hz, 1H), 8.1 (d, J=7 Hz, 2H), 7.93 (br s, 1H), 7.75 (d, J=8 Hz, 1H), 7.64 (d, J=7 Hz, 2H), 7.41 (d, J=7 Hz, 2H), 7.39 (d, J=7 Hz, 2H), 7.37 (t, J=7 Hz, 2H), 7.26 (br s, 1H), 7.25 (t, J=7 Hz, 2H), 7.1 (br s, 2H), 6.77 (d, J=2 Hz, 1H), 6.67 (dd, J=2, 8 Hz, 1H), 5.73 (d, J=14 Hz, 2H), 3.76 (br t, 4H), 3.45-3.56 (m, 20H), 3.2 (q, J=7 Hz, 2H), 2.92 (s, 2H), 2.42 (t, J=7 Hz, 4H), 2.39 (s, 3H), 2.32 (s, 2H), 1.77-1.85 (m, 4H), 1.75 (s, 12H), 1.66 (p, J=7 Hz, 4H), 1.52 (p, J=7 Hz, 4H), 1.01 (s, 6H).

Example 6. Synthesis of 5-(2-((E,3Z)-3-(4-(21-((2-carbamoyl-5-(3,6,6-trimethyl-4-oxo-4,5,6,7-tetrahydro-1H-indazol-1-yl)phenyl)amino)-6,9,12,15,18-pentaoxa-2-azahenicosyl)phenyl)-5-((E)-3,3-dimethyl-5-sulfo-1-(4-sulfobutyl)indolin-2-ylidene)penta-1,3-dien-1-yl)-3,3-dimethyl-5-sulfo-3H-indol-1-ium-1-yl)pentane-1-sulfonate (103)

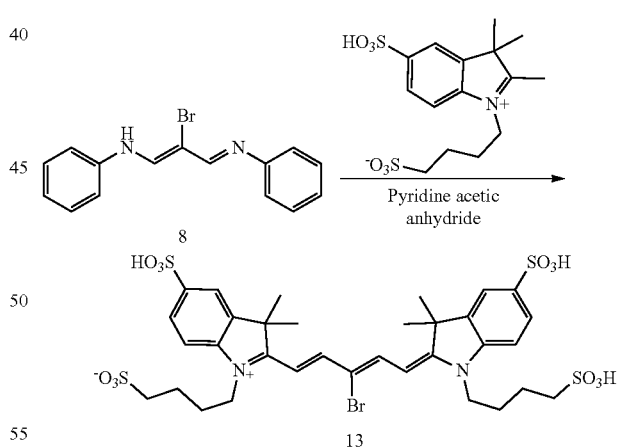

4-(2-((1E,3Z)-3-bromo-5-((E)-3,3-dimethyl-5-sulfo-1-(4-sulfobutyl)indolin-2-ylidene)penta-1,3-dien-1-yl)-3,3-dimethyl-5-sulfo-3H-indol-1-ium-1-yl)butane-1-sulfonate (13)

4-(2,3,3-trimethyl-5-sulfo-3H-indol-1-ium-1-yl)butane-1-sulfonate (665 mg, 1.77 mmol), sodium acetate (1.88 g, 23 mmol) and 8 (338 mg, 885 μmol) were dissolved in ethanol (27 mL) and stirred at RT and then heated to 50° C. for 2 d. The mixture was then concentrated, passed through ion exchange (Dowex 50, H⁺, MeOH), and chromatographed (120 g C-18, 0 to 100% MeOH) to give product 13 (94 mg, 12%) as a blue metallic looking solid. ¹H-NMR (dmso-$d_6$) δ 8.52 (d, J=14 Hz, 2H), 7.87 (d, J=1.5 Hz, 2H), 7.66 (dd, J=2, 8 Hz, 2H), 7.48 (d, J=8 Hz, 2H), 6.35 (d, J=14 Hz, 2H), 4.18 (br t, J=7 Hz, 4H), 2.59 (t, J=7 Hz, 4H), 1.84 (p, J=7 Hz, 4H), 1.73 (hidden p, J=7 Hz, 4H), 1.73 (s, 12H).
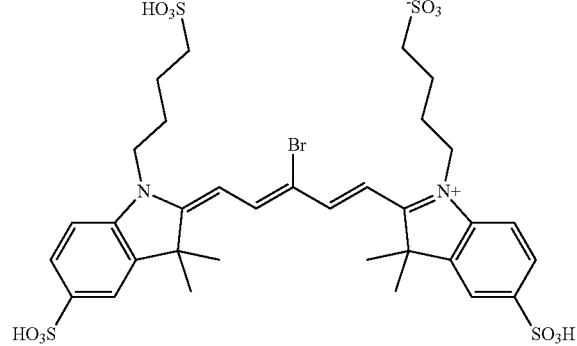
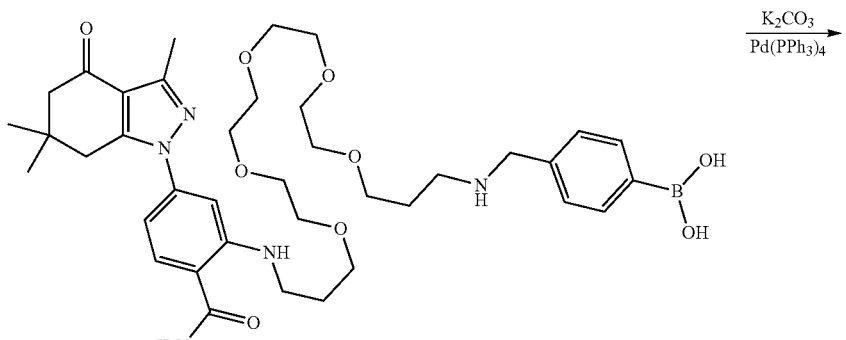
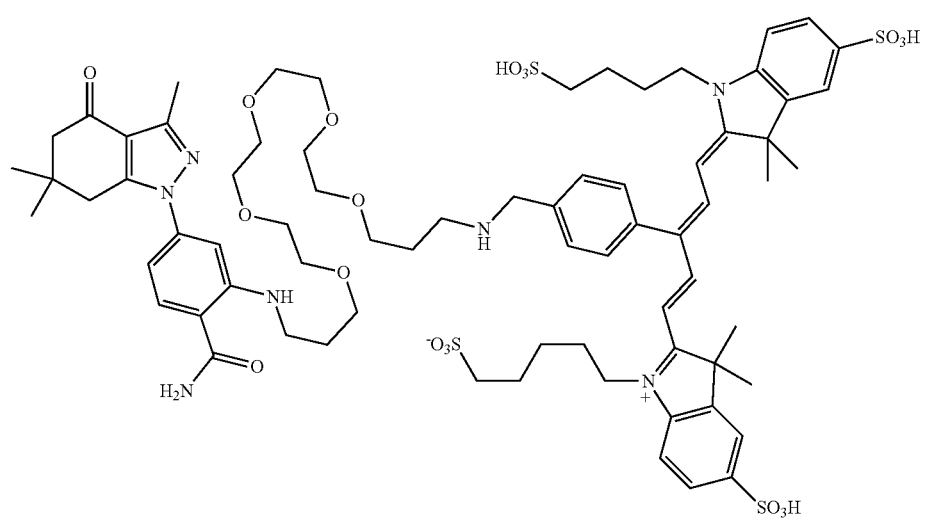

5-(2-(((1E,3Z)-3-(4-(21-((2-carbamoyl-5-(3,6,6-trimethyl-4-oxo-4,5,6,7-tetrahydro-1H-indazol-1-yl)phenyl)amino)-6,9,12,15,18-pentaoxa-2-azahenicosyl)phenyl)-5-((E)-3,3-dimethyl-5-sulfo-1-(4-sulfobutyl)indolin-2-ylidene)penta-1,3-dien-1-yl)-3,3-dimethyl-5-sulfo-3H-indol-1-ium-1-yl)pentane-1-sulfonate (103)

The dye 13 (35 mg), 85 mg, 98 μmol) and the boronate 6 (73 mg, 98 μmol) along with Pd(0)(PPh$_3$)$_4$ (11 mg, 9.8 μmol) and potassium carbonate (27 mg, 196 μmol) were dissolved in water/dioxane (1 mL ea.). The mixture was bubbled with N$_2$ and heated to 100° C. for 1 h. The reaction mixture was allowed to cool with stirring overnight and then concentrated and chromatographed (120 g isco C-18, 0 to 100% MeOH) to give product (44.7 mg, 30.7%) as a blue solid.

$^1$H-NMR (dmso-d$_6$) δ 9.19 (br s, 2H), 8.50 (d, J=14 Hz, 2H), 7.83 (s, 2H), 7.75 (d, J=8 Hz, 1H), 7.67 (d, J=7 Hz, 2H), 7.60 (d, j=7 Hz, 2H), 7.35 (d, J=7 Hz, 4H), 6.78 (d, J=2 Hz, 1H), 6.67 (dd, J=2, 8 Hz, 1H), 5.59 (d, J=14 Hz, 2H), 4.31 (br s, 2H), 3.68 (br m, 4H), 3.44-3.56 (br m, 20H), 3.21 (m, 2H), 3.06 (m, 2H), 2.92 (s, 2H), 2.39 (s, 3H), 2.32 (s, 2H), 2.27 (m, 4H), 2.02 (m, 2H), 1.81 (m, 2H), 1.74 (s, 12H), 1.51 (m, 8H), 1.01 (s, 6H).

Example 7. Synthesis of 4-(2-((E,3Z)-5-((E)-3,3-dimethyl-5-sulfo-1-(4-sulfobutyl)indolin-2-ylidene)-3-(4-(21-((2-(dimethylcarbamoyl)-5-(3,6,6-trimethyl-4-oxo-4,5,6,7-tetrahydro-1H-indazol-1-yl)phenyl)amino)-6,9,12,15,18-pentaoxa-2-azahenicosyl)phenyl)penta-1,3-dien-1-yl)-3,3-dimethyl-5-sulfo-3H-indol-1-ium-1-yl)butane-1-sulfonate (104)

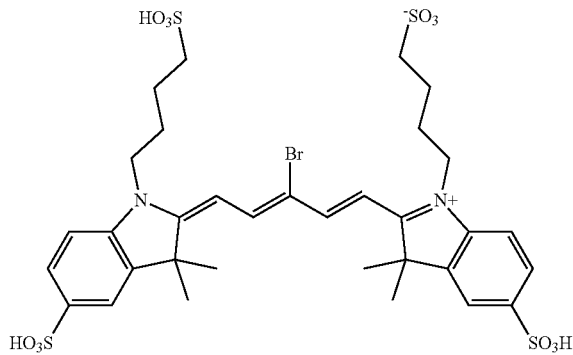

13

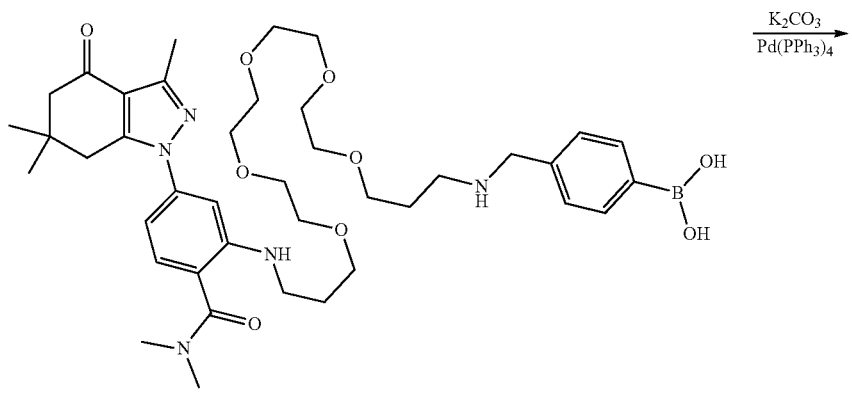

11

-continued

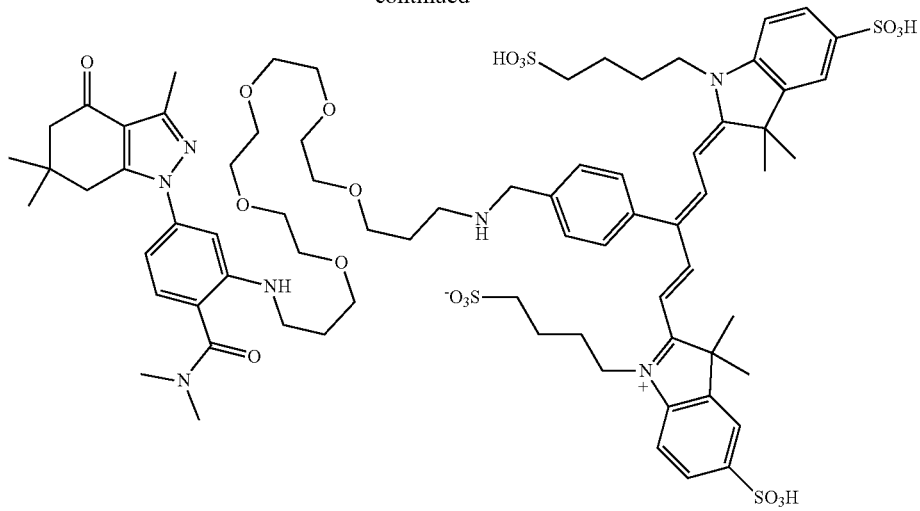

104

The dye 13 (62 mg, 72 μmol) and the dimethyl boronate 11 (73 mg, 98 μmol) along with Pd(0)(PPh$_3$)$_4$ (8 mg, 96.5 μmol) and potassium carbonate (18 mg, 131 mmol) were dissolved in water/dioxane (1 mL ea.). The mixture was bubbled with N$_2$ and heated to 100° C. After 1 h, the reaction mixture was allowed to cool and was then concentrated. The next day the sample was dissolved in water and passed over a SCX resin (Dowex 50-x8 200-400 mesh, 2 g) onto a C-18 column with water and chromatographed (50 g C-18, 0 to 100% MeOH) to give product 104 (35.8 mg, 37%) as a blue solid. LC/MS gave a single peak with m/z=753.7 for [M+2]$^{2+}$.

Example 8. Synthesis of 4-(2-((E)-2-((E)-4'-(21-((2-carbamoyl-5-(3,6,6-trimethyl-4-oxo-4,5,6,7-tetrahydro-1H-indazol-1-yl)phenyl)amino)-6,9,12,15,18-pentaoxa-2-azahenicosyl)-6-(2-((E)-3,3-dimethyl-1-(4-sulfobutyl)indolin-2-ylidene)ethylidene)-3,4,5,6-tetrahydro-[1,1'-biphenyl]-2-yl)vinyl)-3,3-dimethyl-3H-indol-1-ium-1-yl)butane-1-sulfonate (105)

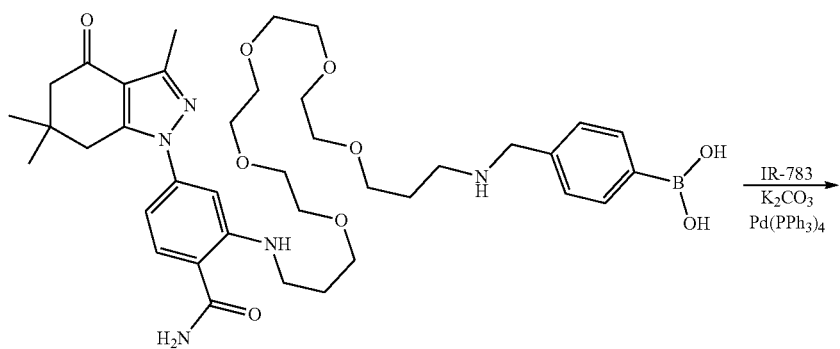

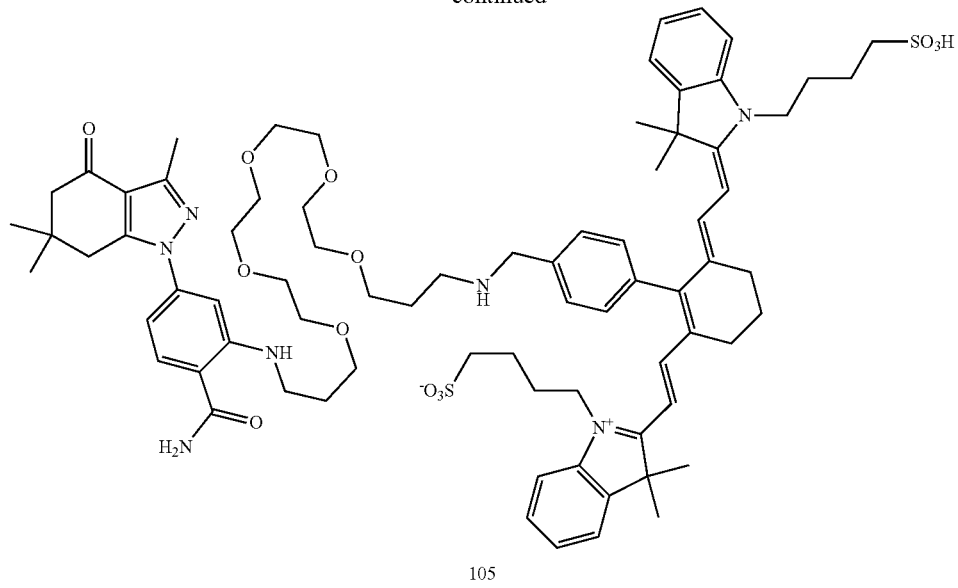

105

Phenylborate 6 (500 mg, 678 μmol), dye IR-783 14 (Aldrich, 507.9 mg, 678 μmol), tetrakis(triphenylphosphine)palladium(0) (78.3 mg, 67.8 μmol) and potassium carbonate (187 mg, 1.35 μmol) were combined in dioxane/water (7.5 mL and 7.5 mL), bubbled with N$_2$ and heated to 100° C. for 1.5 h. The mixture was concentrated, then dissolved in 9/1:MeOH/NH$_4$OH (2 mL) and diluted with CH$_2$Cl$_2$ (18 mL) and loaded onto a column and chromatographed (2.5× 15 cm. with CH$_2$Cl$_2$ (100 mL), then 9/0.9/0.1: CH$_2$Cl$_2$/MeOH/NH$_3$ (250 mL), then 4/0.9/0.1: CH$_2$Cl$_2$/MeOH/NH$_3$ (500 mL)) to give the product 105 (320 mg, 34%) as a green solid. $^1$H NMR (CD$_3$OD) δ 8.14 (s, 1H, formate), 7.75 (d, J=8.1 Hz, 2H), 7.70 (d, J=8.4 Hz, 1H), 7.35 (d, J=8.1 Hz, 2H), 7.21-7.33 (m, 6H), 7.15 (br m, 4H), 6.83, (d, J=2.1 Hz, 1H), 6.67 (dd, J=2.1, 8.4 Hz, 1H), 6.07 (br, 2H), 4.47 (s, 2H), 4.06 (br s, 4H), 3.73 (t, J=5.5 Hz, 2H), 3.52-3.70 (m, 20H), 2.89 (s, 2H), 2.83 (t, J=7.2 Hz, 4H), 2.72 (br s, 4H), 2.44 (s, 3H), 2.39 (s, 2H), 2.13 (m, 2H), 2.02 (br m, 2H), 1.76-1.94 (m, 10H), 1.53 (br s, 12H), 1.19 (s 12H), 1.06 (s, 6H). HRMS (ESI) [M+2H]$^{2+}$ calcd for C$_{76}$H$_{101}$N$_7$O$_3$S$_2$, 692.8522; found 692.8519.

Example 9. Synthesis of 4-(2-((E)-2-((E)-4'-((19-((2-carbamoyl-5-(3,6,6-trimethyl-4-oxo-4,5,6,7-tetrahydro-1H-indazol-1-yl)phenyl)amino)-4,7,10,13,16-pentaoxanonadecyl)carbamoyl)-6-(2-((E)-3,3-dimethyl-1-(4-sulfobutyl)indolin-2-ylidene)ethylidene)-3,4,5,6-tetrahydro-[1,1'-biphenyl]-2-yl)vinyl)-3,3-dimethyl-3H-indol-1-ium-1-yl)butane-1-sulfonate (106)

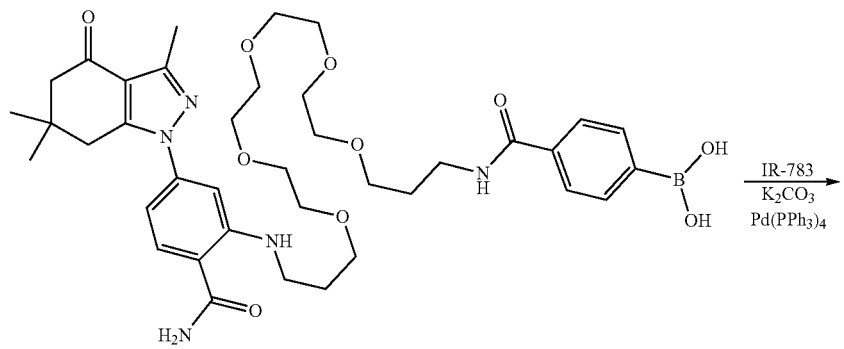

7

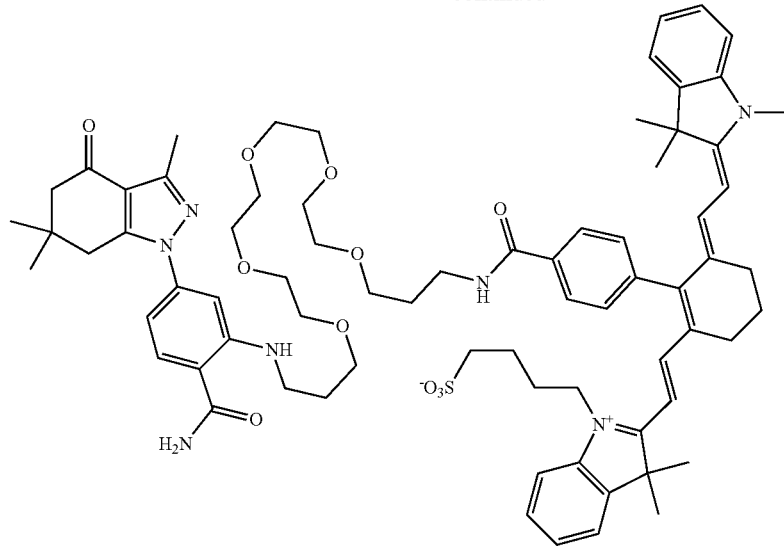

106

Boronic acid 7 (107 mg, 142 μmol), dye IR-783 14 (Aldrich, 73 mg, 97 μmol), tetrakis(triphenylphosphine) palladium(0) (17 mg, 14 μmol) and potassium carbonate (39 mg, 284 μmol) were combined in dioxane/water (2 mL and 2 mL), bubbled with $N_2$ and heated to 100° C. for 1.5 h. The reaction was allowed to cool, concentrated and chromatographed (Grace C-18 flash column, 0 to 100% methanol over 2 h, 4 mL/min) to give a green solid. The product was further purified by prep HPLC (30 to 100% methanol, 20 mL/m, Agilent C-18, 21.1×25 cm). This product was chromatographed once more (silica gel, 2.5×15 cm. with $CH_2Cl_2$ (100 mL), then 9/0.9/0.1: $CH_2Cl_2$/MeOH/$NH_3$ (250 mL), then 4/0.9/0.1: $CH_2Cl_2$/MeOH/$NH_3$ (500 mL)) to give 106 (42 mg, 31%) as a dark green solid. $^1$H NMR ($CD_3OD$-$CDCl_3$) δ 8.12 (d, J=8.2 Hz, 2H), 7.77 (s, $CHCl_3$), 7.71 (d, J=8.4 Hz, 1H), 7.37 (d, J=8.2 Hz, 2H), 7.34 (t, J=7.5 Hz, 2H), 7.28 (d, J=7.5 Hz, 2H), 7.23 (d, J=8.2 Hz, 2H), 7.18 (br d, J=14 Hz, 2H), 7.16 (t, J=7.5 Hz, 2H), 6.81 (d, J=2 Hz, 1H), 6.67 (dd, J=2.0, 8.4 Hz, 1H), 6.18 (br d, J=14 Hz, 2H), 3.71 (m, 2H), 4.08 (m, 4H), 3.56-3.70 (m, 22H), 3.30 (t, J=7 Hz, 2H), 2.90 (s, 2H), 2.89 (t, J=7 Hz, 4H), 2.74 (br m, 4H), 2.49 (s, 3H), 2.41 (s, 2H), 2.07 (br m, 2H), 2.00 (p, J=6.5 Hz, 2H), 1.88-1.96 (m, 10H), 1.18 (s, 12H), 1.10 (s, 6H). HRMS (ESI) [M–H]$^-$ calcd. for $C_{76}H_{99}N_7O_{14}S_2$ 1396.6619; found 1396.6633.

Example 10. Synthesis of 4-(2-((E)-2-((E)-6-(2-((E)-3,3-dimethyl-1-(4-sulfobutyl)indolin-2-ylidene) ethylidene)-4'-(21-((2-(dimethylcarbamoyl)-5-(3,6,6-trimethyl-4-oxo-4,5,6,7-tetrahydro-1H-indazol-1-yl) phenyl)amino)-6,9,12,15,18-pentaoxa-2-azahenicosyl)-3,4,5,6-tetrahydro-[1,1'-biphenyl]-2-yl)vinyl)-3,3-dimethyl-3H-indol-1-ium-1-yl)butane-1-sulfonate (107)

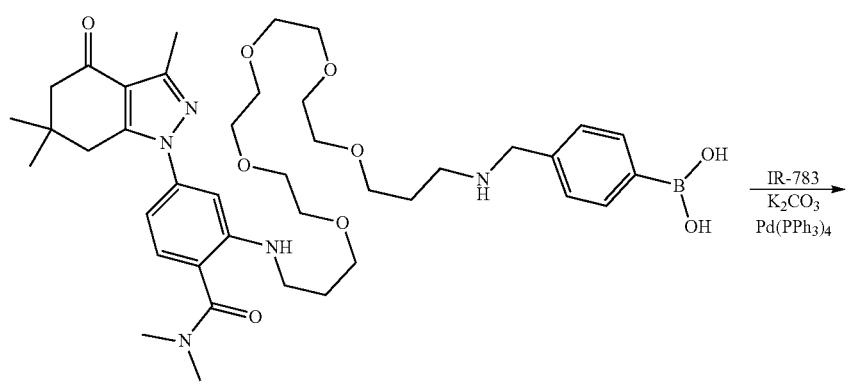

11

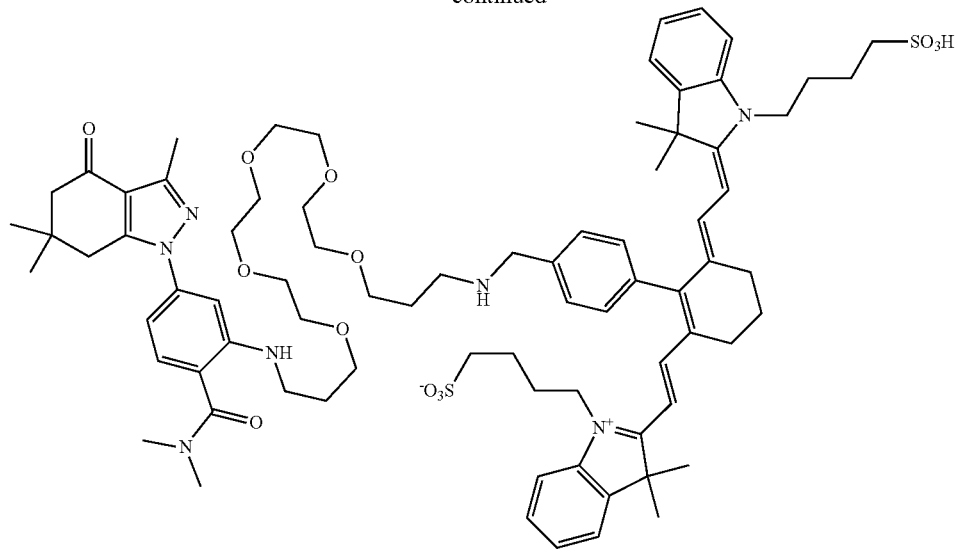

107

Boronic acid 11 (61 mg, 80 μmol), dye IR-783 14 (Aldrich, 60 mg, 80 μmol), tetrakis(triphenylphosphine)palladium(0) (9 mg, 8 μmol) and potassium carbonate (22 mg, 160 μmol) were combined in dioxane/water (1 mL each), bubbled with $N_2$ and heated to 100° C. for 1 hour. The reaction mixture was concentrated and chromatographed (silica gel, 0 to 30% MeOH/$NH_3$ in $CH_2Cl_2$) to give 105 (60.2 mg, 53%) as a dark green solid. LC/MS shows single peak with m/z=707.0 $[M+2]^{2+}$.

Example 11. Synthesis of 4-(2-((E)-2-((E)-4'-(21-((2-carbamoyl-5-(3,6,6-trimethyl-4-oxo-4,5,6,7-tetrahydro-1H-indazol-1-yl)phenyl)amino)-6,9,12,15,18-pentaoxa-2-azahenicosyl)-6-((E)-2-(1,1-dimethyl-3-(4-sulfobutyl)-1,3-dihydro-2H-benzo[e]indol-2-ylidene)ethylidene)-3,4,5,6-tetrahydro-[1,1'-biphenyl]-2-yl)vinyl)-3,3-dimethyl-3H-benzo[g]indol-1-ium-1-yl)butane-1-sulfonate (111)

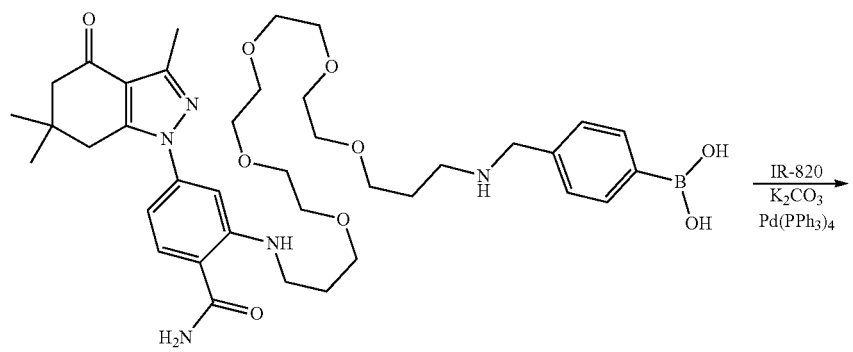

6

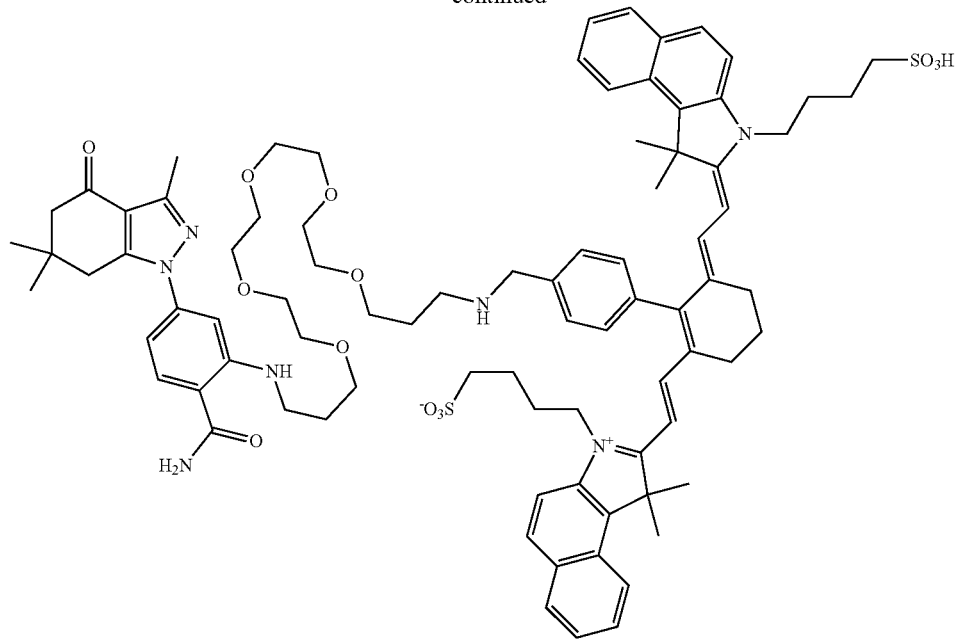

111

Phenylborate 6 (500 mg, 678 μmol), dye IR-820 17 (80% by wt., Aldrich, 720 mg, 678 μmol), tetrakis(triphenylphosphine)palladium(0) (78.3 mg, 67.8 μmol) and potassium carbonate (187 mg, 1.35 mmol) were combined in dioxane/water (7.5 mL and 7.5 mL), bubbled with N2 and heated to 100° C. for 2 h. The mixture was concentrated, then dissolved in 19/1:CH$_2$Cl$_2$/MeOH (20 mL) and loaded onto a column and chromatographed (2.5×15 cm. with CH$_2$Cl$_2$ (100 mL), then 9/0.9/0.1: CH$_2$Cl$_2$MeOH/NH$_3$ (250 mL), then 4/0.9/0.1: CH$_2$Cl$_2$/MeOH/NH$_3$ (500 mL)) to give the product 111 (252 mg, 25%) as a lime green solid. $^1$H NMR NMR (CD$_3$OD-CDCl$_3$) δ 8.18 (d, j=8.2 Hz, 2H), 8.00 (d, J=8.2 Hz, 2H), 7.93 (d, J=8.2 Hz, 2H), 7.91 (d, J=7.0 Hz, 2H), 7.77 (CHCl$_3$), 7.70 (d, J=8.4 Hz, 1H), 7.54 (t, J=7.0 Hz, 2H), 7.44 (d, J=8.2 Hz, 2H), 7.42 (t, J=7.0 Hz, 2H), 7.28 (d, J=14 Hz, 2H), 6.78 (d, J=2 Hz, 1H), 6.65 (dd, J=2, 14 Hz, 1H), 6.22 (d, H=14 Hz, 2H), 4.2 (br t, J=7.0 Hz, 4H), 3.54-3.74 (m, 22H), 3.26 (t, J=7.0 Hz, 2H), 2.91 (t, J=7.0 Hz, 4H), 2.87 (s, 2H), 2.78 (br t, 4H), 2.48 (s, 3H), 2.39 (s, 2H), 2.12 (m, 2H), 2.06 (p, J=7.0 Hz, 2H), 1.93-2.02 (br m, 8H), 1.89 (p, J=7.0 Hz, 2H), 1.51 (s, 12H), 1.07 (s, 6H). HRMS (ESI) calcd. for C$_{84}$H$_{103}$N$_7$O$_{14}$S$_2$ 1496.6932; found 1496.6942.

Example 12. Synthesis of 4-(2-((E)-2-((E)-4'-((19-((2-carbamoyl-5-(3,6,6-trimethyl-4-oxo-4,5,6,7-tetrahydro-1H-indazol-1-yl)phenyl)amino)-4,7,10,13,16-pentaoxanonadecyl)carbamoyl)-64(E)-2-(1,1-dimethyl-3-(4-sulfobutyl)-1,3-dihydro-211-benzo[e]indol-2-ylidene)ethylidene)-3,4,5,6-tetrahydro-[1,1'-biphenyl]-2-yl)vinyl)-3,3-dimethyl-3H-benzo[g]indol-1-ium-1-yl)butane-1-sulfonate (112)

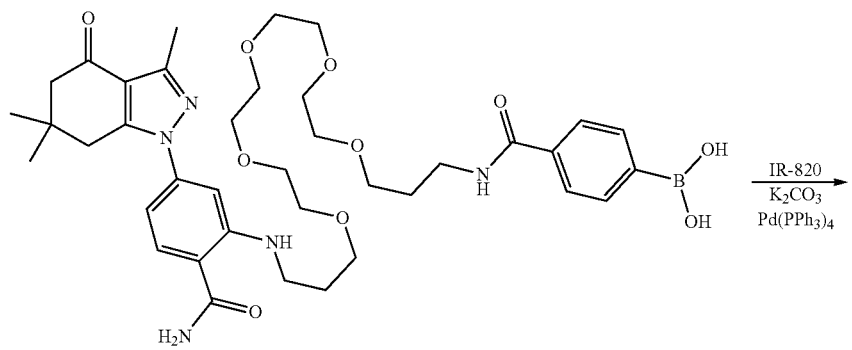

7

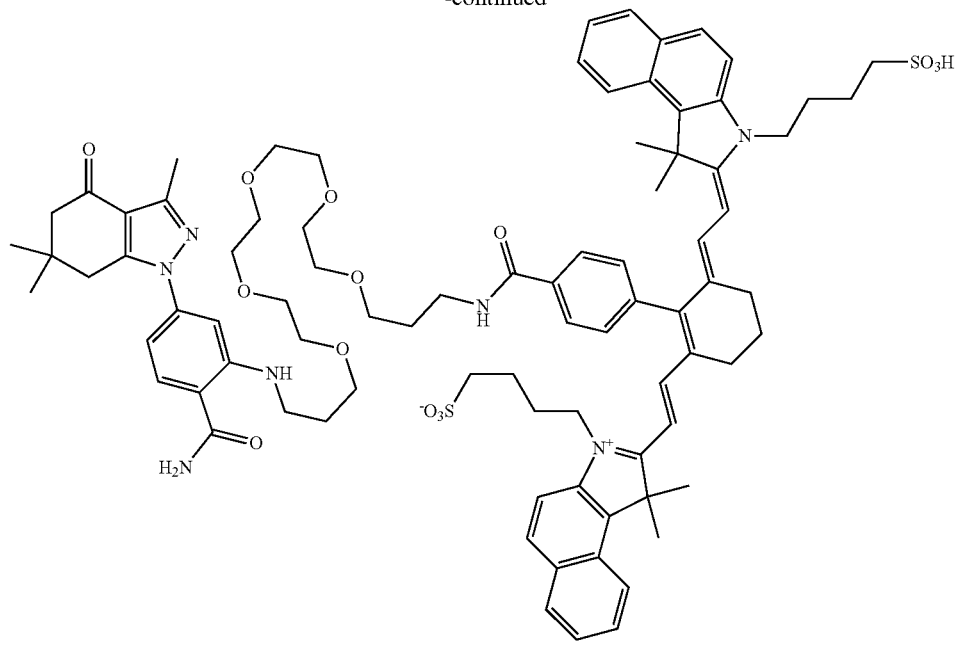

112

Phenylborate 7 (114 mg, 152 μmol), dye IR-820 17 (80% by wt., Aldrich, 161 mg, 152 μmol), tetrakis(triphenylphosphine)palladium(0) (18 mg, 15 μmol) and potassium carbonate (42 mg, 303 μmol) were combined in dioxane/water (2 mL each), bubbled with N2 and heated to 100° C. for 1.5 h. The mixture was concentrated and chromatographed (C-18, 0 to 100% MeOH in water) to give clean product 112 (65 mg, 27%) as a lime green solid. $^1$H NMR (CD$_3$OD—CDCl$_3$) δ 8.18 (d, j=8.2 Hz, 2H107 8.00 (d, J=8.2 Hz, 2H), 7.93 (d, J=8.2 Hz, 2H), 7.91 (d, J=7.0 Hz, 2H), 7.77 (CHCl$_3$), 7.70 (d, J=8.4 Hz, 1H), 7.54 (t, J=7.0 Hz, 2H), 7.44 (d, J=8.2 Hz, 2H), 7.42 (t, J=7.0 Hz, 2H), 7.28 (d, J=14 Hz, 2H), 6.78 (d, J=2 Hz, 1H), 6.65 (dd, J=2, 14 Hz, 1H), 6.22 (d, H=14 Hz, 2H), 4.2 (br t, J=7.0 Hz, 4H), 3.54-3.74 (m, 22H), 3.26 (t, J=7.0 Hz, 2H), 2.91 (t, J=7.0 Hz, 4H), 2.87 (s, 2H), 2.78 (br t, 4H), 2.48 (s, 3H), 2.39 (s, 2H), 2.12 (m, 2H), 2.06 (p, J=7.0 Hz, 2H), 1.93-2.02 (br m, 8H), 1.89 (p, J=7.0 Hz, 2H), 1.51 (s, 12H), 1.07 (s, 6H). HRMS (ESI) [M–H]$^-$ calcd. for C$_{84}$H$_{103}$N$_7$O$_{14}$S$_2$ 1496.6932; found 1496.6942.

Example 13. Synthesis of 4-(2-((E)-2-(((E)-6-((E)-2-(1,1-dimethyl-3-(4-sulfobutyl)-1,3-dihydro-2H-benzo[e]indol-2-ylidene)ethylidene)-4'-(21-((2-(dimethylcarbamoyl)-5-(3,6,6-trimethyl-4-oxo-4,5,6,7-tetrahydro-1H-indazol-1-yl)phenyl)amino)-6,9,12,15,18-pentaoxa-2-azahenicosyl)-3,4,5,6-tetrahydro-[1,1'-biphenyl]-2-yl)vinyl)-3,3-dimethyl-3H-benzo[g]indol-1-ium-1-yl)butane-1-sulfonate (113)

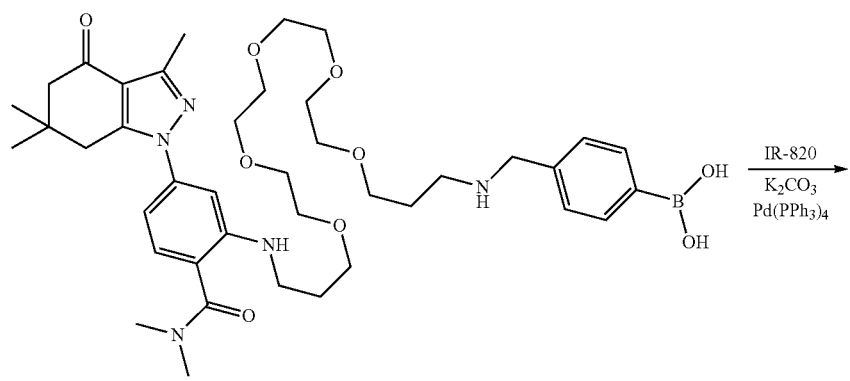

11

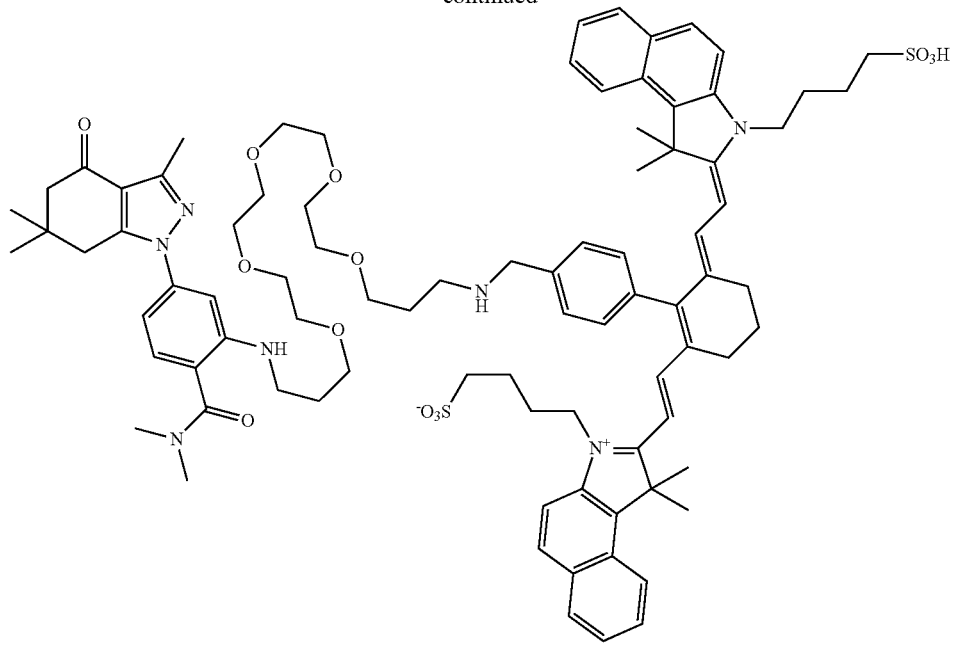

113

Boronic acid 11 (55 mg, 72 μmol), dye IR-820 17 (80% by wt., Aldrich, 76 mg, 72 tetrakis(triphenylphosphine) palladium(0) (8 mg, 7 μmol) and potassium carbonate (20 mg, 143 μmol) were combined in dioxane/water (1 mL each), bubbled with N2 and heated to 100° C. for 1 hour. The reaction mixture was concentrated and chromatographed (silica gel, 0 to 30% MeOH/NH$_3$ in CH$_2$Cl$_2$) to give 113 (44.5 mg, 41%) as a lime green solid. LC/MS shows single peak with m/z=1513.7 [M+1]$^+$.

Example 14. Synthesis of 4-(2-((E)-2-((E)-4'-(21-((2-carbamoyl-5-(3,6,6-trimethyl-4-oxo-4,5,6,7-tetrahydro-1H-indazol-1-yl)phenyl)amino)-6,9,12,15,18-pentaoxa-2-azahenicosyl)-6-(2-((E)-3,3-dimethyl-5-sulfo-1-(4-sulfobutyl)indolin-2-ylidene)ethylidene)-3,4,5,6-tetrahydro-[1,1'-biphenyl]-2-yl)vinyl)-3,3-dimethyl-5-sulfo-3H-indol-1-ium-1-yl)butane-1-sulfonate (108)

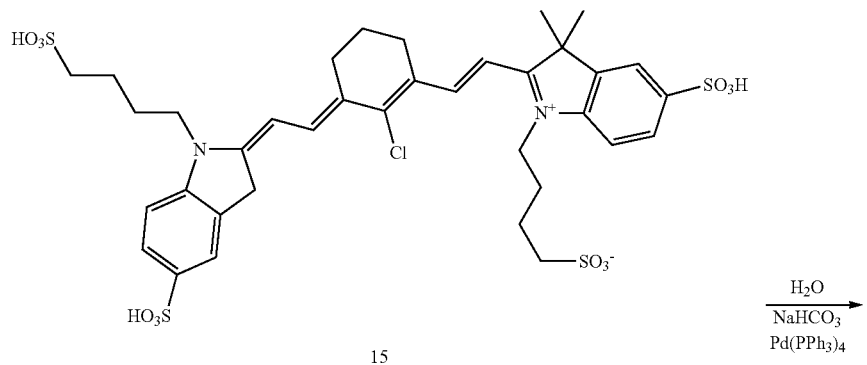

15

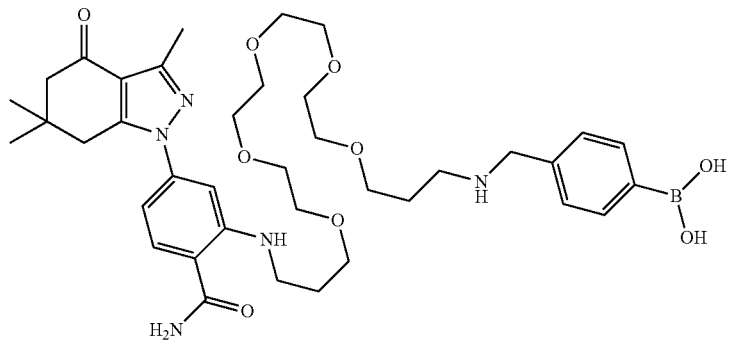

6

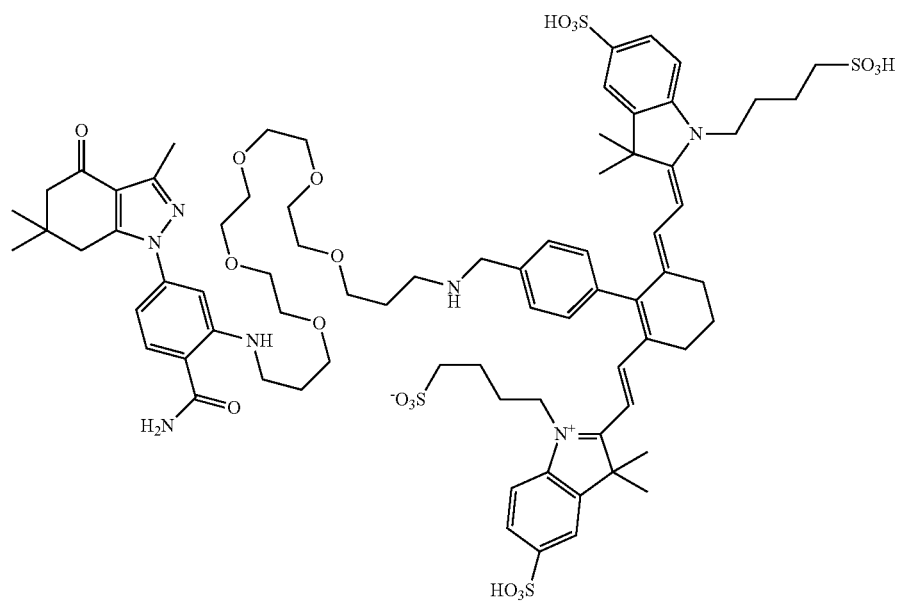

108

Phenylborate 6 (71 mg, 96 μmol), dye 26, (85 mg, 95 μmol), tetrakis(triphenylphosphine) palladium(0) (11 mg, 9.6 μmol) and sodium bicarbonate (46 mg, 431 μmol) were combined in water (2 mL), bubbled with $N_2$ for 30 m and heated to 100° C. for 1 h. The reaction mixture was dissolved in water and passed through Dowex-50 (2.75 g) onto an Isco 150 g C-18 column and chromatographed (0 to 100% MeOH in water) to give the product 108 (33.3 mg, 22%) as a dark green solid. LC/MS gave a single broad peak with m/z=772.9 $[M+2]^{2+}$ and m/z=771.0 $[M-2]^{2-}$. $^1$H NMR (DMSO-$d_6$) δ 8.98 (br s, 2H), 7.74 (d, J=8 Hz, 1H), 7.72 (d, J=7 Hz, 2H), 7.56 (d, J=7.0 Hz, 2H), 7.55 (s, 2H), 7.35 (d, J=8 Hz, 2H), 7.28 (d, J=8 Hz, 2H), 7.04 (d, J=14 Hz, 2H), 6.77 (br s, 1H), 6.66 (d, J=8 Hz, 1H), 6.23 (d, J=14 Hz, 2H), 4.86 (v br, water), 4.38 (br t, J=7.0 Hz, 4H), 4.05 (br m, 4H), 3.42-3.57 (m, 20H), 3.19 (t, J=7.0 Hz, 2H), 3.07 (br m, 2H), 2.91 (s, 2H), 2.69 (br m, 4H), 2.51 (t, J=7.0 Hz, 4H), 2.49 (DMSO), 2.38 (s, 3H), 2.32 (s, 2H), 2.01 (m, 2H), 1.94 (m, 2H), 1.79 (p, J=7.0 Hz, 2H), 1.58-1.74 (br m, 8H), 1.12 (s, 12H), 1.00 (s, 6H).

Example 15. Synthesis of 4-(2-((E)-2-((E)-6-(2-((E)-3,3-dimethyl-5-sulfo-1-(4-sulfobutyl)indolin-2-ylidene)ethylidene)-4'-(21-((2-(dimethylcarbamoyl)-5-(3,6,6-trimethyl-4-oxo-4,5,6,7-tetrahydro-1H-indazol-1-yl)phenyl)amino)-6,9,12,15,18-pentaoxa-2-azahenicosyl)-3,4,5,6-tetrahydro-[1,1'-biphenyl]-2-yl)vinyl)-3,3-dimethyl-5-sulfo-3H-indol-1-ium-1-yl)butane-1-sulfonate (109)
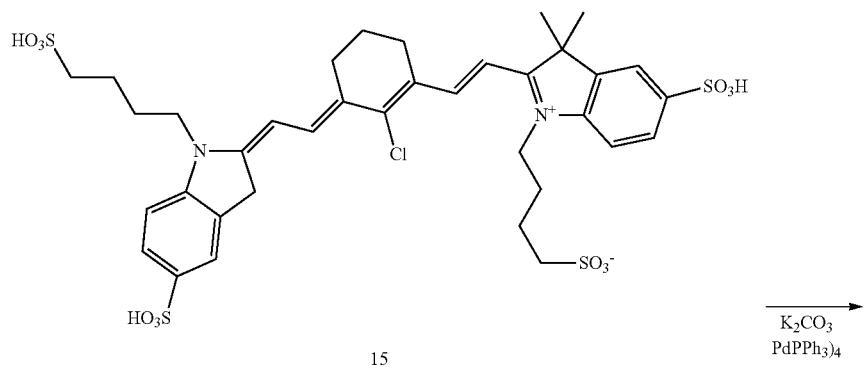
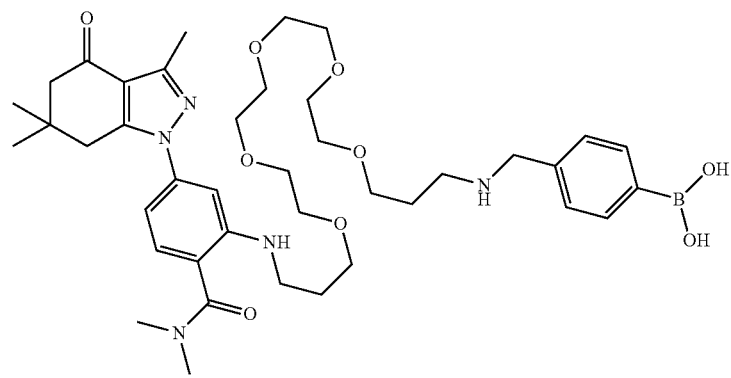
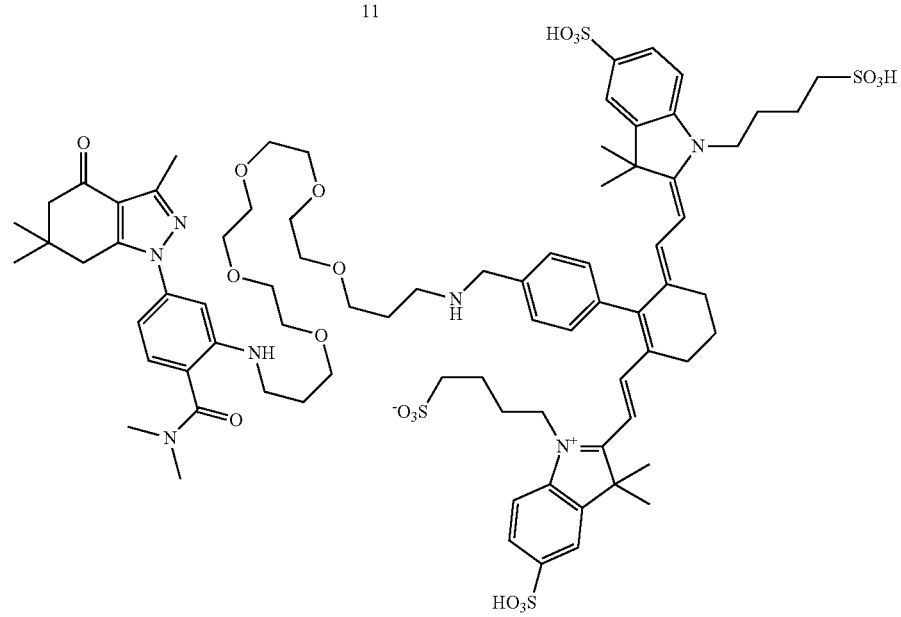

Phenylborate 11 (62 mg, 81 µmol), dye 15, (72 mg, 81 µmol), tetrakis(triphenyl-phosphine)palladium(0) (9 mg, 9.6 µmol) and potassium carbonate (34 mg, 243 µmol) were combined in dioxane/water (1 mL ea.), bubbled with $N_2$ for 30 m and heated to 100° C. for 1 h. The reaction was cooled, concentrated and chromatographed twice (C-18, 0 to 100% MeOH in water w/0.2% formic acid) then passed through Dowex 50x8 (H+ form) to remove unreacted borate and concentrated to give 110 (17 mg, 13%) as a dark green solid. LC/MS gave a broad peak with m/z=786.6 [M+2]2+.

Example 16. Synthesis of 4-(2-((E)-2-((E)-4'-(21-((2-carbamoyl-5-(3,6,6-trimethyl-4-oxo-4,5,6,7-tetrahydro-1H-indazol-1-yl)phenyl)amino)-6,9,12,15,18-pentaoxa-2-azahenicosyl)-6-((E)-2-(1,1-dimethyl-7-sulfo-3-(4-sulfobutyl)-1,3-dihydro-2H-benzo[e]indol-2-ylidene)ethylidene)-3,4,5,6-tetrahydro-[1,1'-biphenyl]-2-yl)vinyl)-1,1-dimethyl-7-sulfo-1H-benzo[e]indol-3-ium-3-yl)butane-1-sulfonate (114)

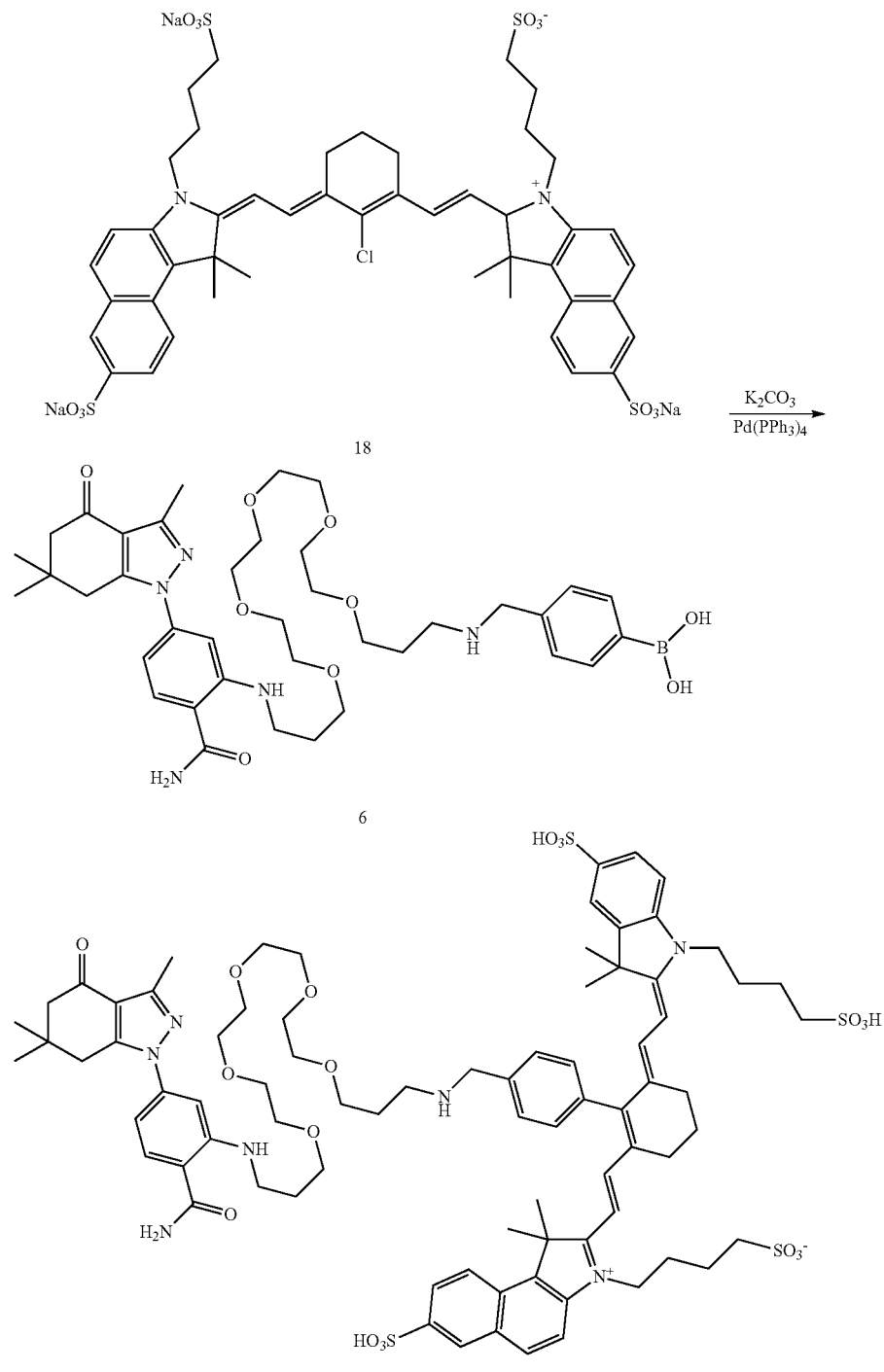

The dye 18 (S 2180 from Few Chemical GmbH, 143 mg, 136 mol) and the boronate 6 (110 mg, 149 mol) along with Pd(0)(PPh$_3$)$_4$ (19 mg, 14 mol) and potassium carbonate (19 mg, 136 mol) were dissolved in water/dioxane (2 mL ea.). The mixture was bubbled with N$_2$ for 30 m and heated to 100° C. for 1 h. The reaction mixture was allowed to cool, then concentrated, dissolved in water and passed through Dowex-50Wx8 (H$^+$ form, 200-400 mesh, 4 g) and onto a 150 g C18 column and chromatogrphed (0 to 100% MeOH w/0.2% formic acid in both) to give product 114 (100 mg, 44%) as a dark green solid. LC/MS gave a single peak with m/z=822.9, [M+2]$^{2+}$ vs expected 822.815. $^1$H-NMR (dmso-d$_6$) δ 9.09 (br s, 2H), 8.22 (s, 2H), 8.09 (d, J=9 Hz, 2H), 7.96 (d, J=8 Hz, 2H), 7.79 (d, J=8 Hz, 2H), 7.77 (d, J=8 Hz, 2H), 7.74 (d, J=8 Hz, 1H), 7.70 (d, J=9 Hz, 2H), 7.41 (d, J=8 Hz, 2H), 7.16 (d, J=14 Hz, 2H), 6.76 (d, J=2 Hz, 1H), 6.66 (dd, J=2, 8 Hz, 1H), 6.28 (d, J=14 Hz, 2H), 4.49 (br t, 2H), 4.18 (br m, 4H), 3.74 (v br, water), 3.57 (t, J=7.0 Hz, 2H), 3.34-3.54 (m, 20H), 3.18 (br m, 2H), 2.91 (s, 2H), 2.73 (br m, 4H), 2.53 (t, J=7.0 Hz, 4H), 2.49 (DMSO), 2.38 (s, 3H), 2.32 (s, 2H), 2.01 (m, 2H), 2.08 (m, 2H), 1.99 (m, 2H), 1.62-1.83 (br m, 8H), 1.43 (s, 12H), 1.00 (s, 6H).

Example 17. Synthesis of 4-(2-((E)-2-((E)-6-((E)-2-(1,1-dimethyl-7-sulfo-3-(4-sulfobutyl)-1,3-dihydro-2H-benzo[e]indol-2-ylidene)ethylidene)-4'-(21-((2-(dimethylcarbamoyl)-5-(3,6,6-trimethyl-4-oxo-4,5,6,7-tetrahydro-1H-indazol-1-yl)phenyl)amino)-6,9,12,15,18-pentaoxa-2-azahenicosyl)-3,4,5,6-tetrahydro-[1,1'-biphenyl]-2-yl)vinyl)-1,1-dimethyl-7-sulfo-1H-benzo[e]indol-3-ium-3-yl)butane-1-sulfonate (115)

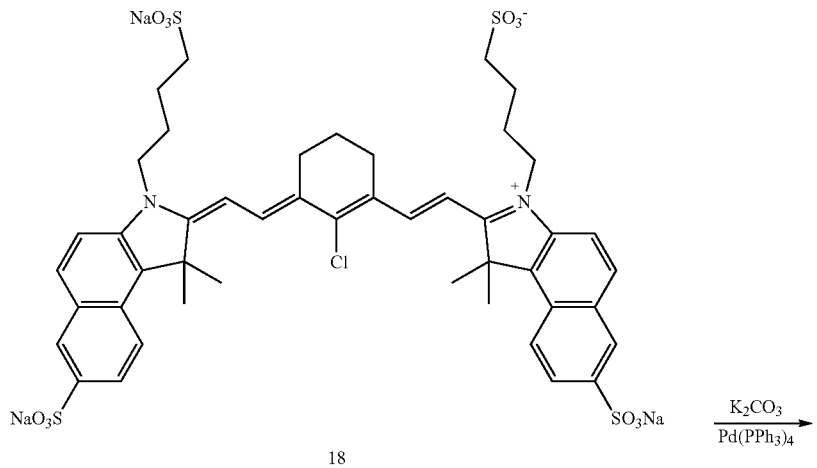

18

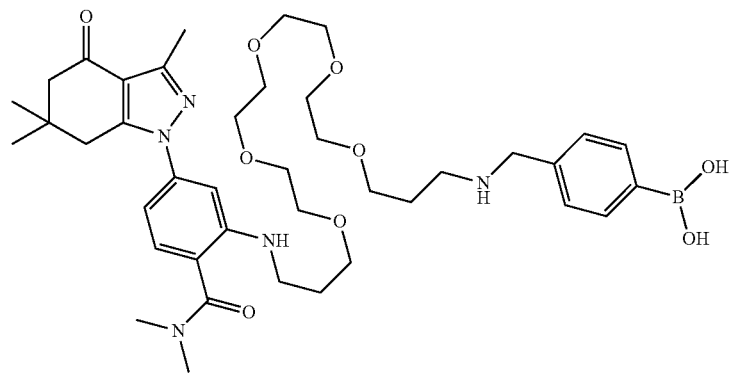

11

-continued

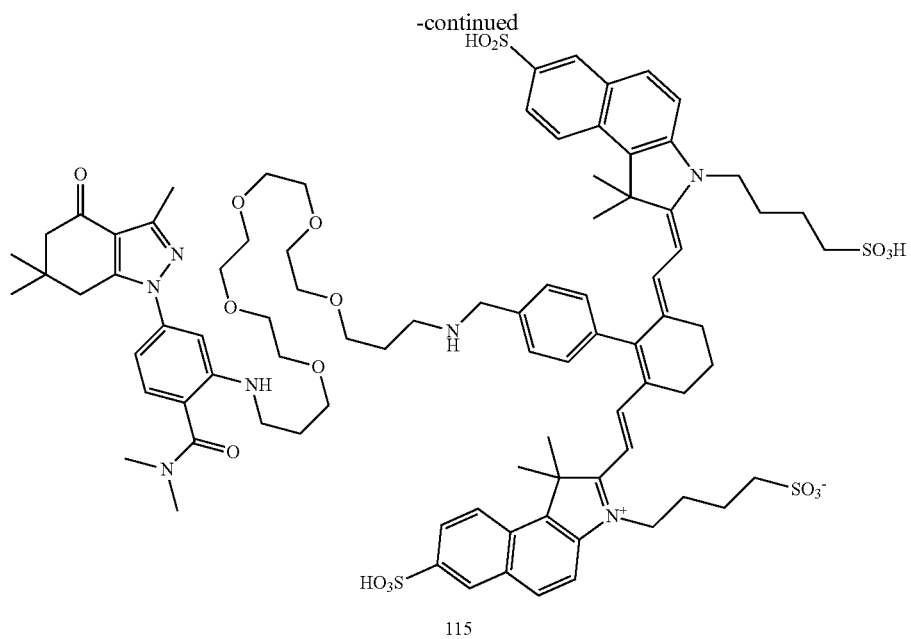

115

The dye 18 (Few Chemical GmbH, 98 mg, 93 mol) and the boronate 11 (71 mg, 93 μmol) along with Pd(0)(PPh$_3$)$_4$ (11 mg, 9 μmol) and potassium carbonate (13 mg, 93 μmol) were dissolved in water/dioxane (1 mL ea.). The mixture was bubbled with N$_2$ for 30 m and heated to 100° C. for 1 h. The reaction mixture was allowed to cool, then concentrated, dissolved in water and passed through Dowex-50Wx8 (H$^+$ form, 200-400 mesh, 4 g) and onto a 150 g C18 column and chromatographed (0 to 100% MeOH w/0.2% formic acid in both) to give product 115 (50 mg, 32%) as a green solid with gold highlights. LC/MS shows a peak with m/z=836.9, [M+2]$^{2+}$. $^1$H-NMR (dmso-d$_6$) δ 9.1 (br s, 2H), 8.22 (s, 2H), 8.09 (d, J=8 Hz, 2H), 7.96 (d, J=7 Hz, 2H), 7.79 (d, J=7 Hz, 2H), 7.77 (d, J=7 Hz, 2H), 7.70 (d, J=8 Hz, 2H), 7.53 (br s, 1H), 7.41 (d, J=7 Hz, 2H), 7.17 (d, J=14 Hz, 2H), 7.15 (d, J=7 Hz, 1H), 6.76 (s, 1H), 6.72 (d, J=7 Hz, 1H), 6.28 (d, J=14 Hz, 2H), 4.49 (br t, 2H), 4.18 (br m, 4H), 3.58 (t, 2H) 3.42-3.51 (br m, 20H), 3.16 (br t, 4H), 2.93 (br s, 6H), 2.89 (s, 2H) 2.75 (m, 4H), 2.53 (m, 2H), 2.38 (s, 3H), 2.31 (s, 2H), 2.09 (m, 2H), 1.99 (m, 2H), 1.75 (m, 4H), 1.44 (s, 12H), 1.00 (s, 6H).

Example 18. 4-(2-((1E,3Z)-3-(4-(21-((2-carbamoyl-5-(3,6,6-trimethyl-4-oxo-4,5,6,7-tetrahydro-1H-indazol-1-yl)phenyl)amino)-2-(3-iodobenzyl)-6,9,12,15,18-pentaoxa-2-azahenicosyl)phenyl)-5-((E)-3,3-dimethyl-1-(4-sulfobutyl)indolin-2-ylidene)penta-1,3-dien-1-yl)-3,3-dimethyl-3H-indol-1-ium-1-yl)butane-1-sulfonate (116)

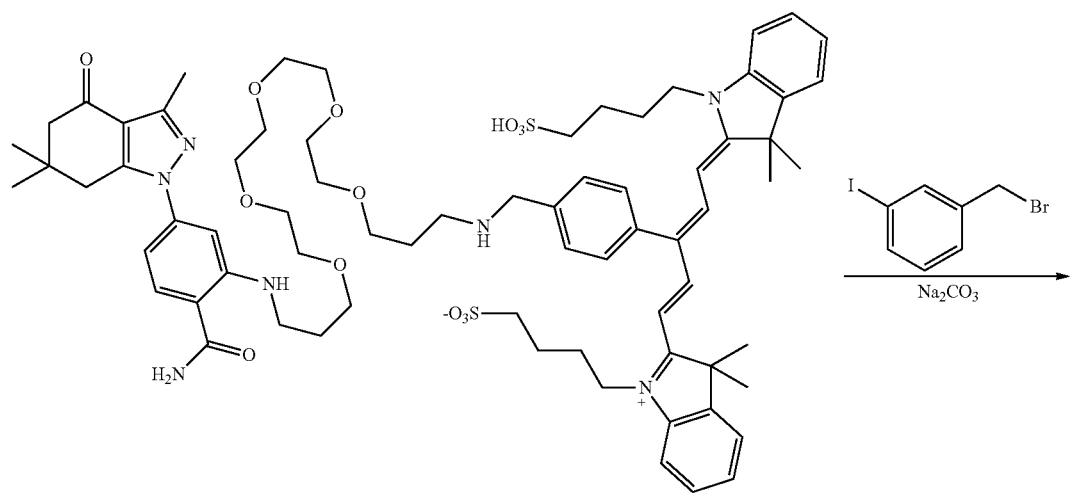

100

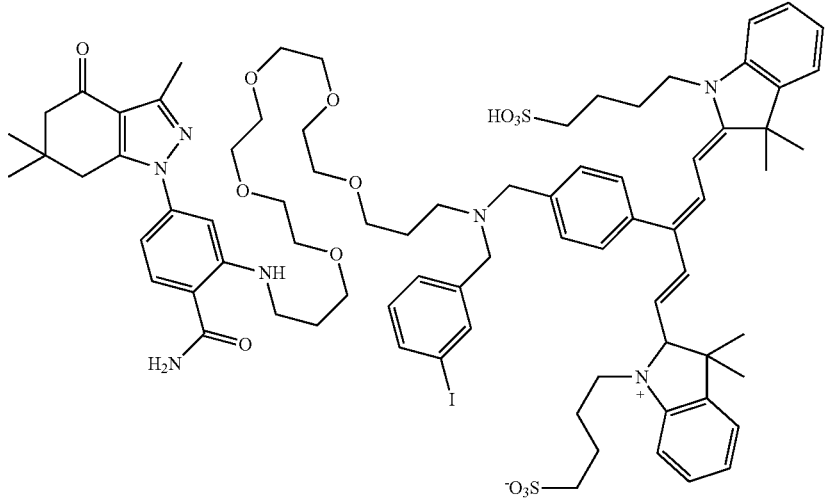

116

Compound 100 (200 mg, 152 μmol), sodium carbonate (48 mg, 455 μmol) and 3-iodobenzyl bromide (59 mg, 197 μmol) were dissolved in methanol (8 mL) and stirred at RT for 20 h. The reaction mixture was then concentrated and chromatographed twice (150 g C-18, 0 to 100% MeOH with 0.2% formic acid) to give product 116 (136 mg, 59%) as a blue solid. LC/MS shows a single peak with m/z=767.8 [M+2H]$^{2+}$. $^1$H-NMR (dmso-d$_6$) δ 10.32 (br s, 1H), 8.47 (d, J=14 Hz, 2H), 8.40 (br t, 1H), 8.03 (s, 1H), 7.93 (br s, 1H), 7.73-7.84 (m, 4H) 7.63 (d, J=7 Hz, 2H), 7.35-7.43 (m, 6H), 7.26 (t, J=7 Hz, 2H), 7.24 (d, J=7 Hz, 2H), 6.76 (s, 1H), 6.67 (d, J=7 Hz, 1H), 5.69 (d, J=14 Hz, 2H), 4.46 (br m, 2H), 4.38 (br m, 2H), 3.82 (br m, 2H), 3.6-3.72 (m, 4H) 3.38-3.50 (m, 20H), 3.19 (m, 2H), 3.08 (m, 2H), 2.91 (s, 2H), 2.42 (m, 2H), 2.39 (s, 3H), 2.32 (s, 2H), 2.10 (m, 2H), 1.79 (m, 2H), 1.75 (s, 6H), 1.73 (s, 6H), 1.42-1.65 (br m, 8H), 1.00 (s, 6H).

Example 19. 4-(2-((E)-2-((E)-4'-(21-((2-carbamoyl-5-(3,6,6-trimethyl-4-oxo-4,5,6,7-tetrahydro-1H-indazol-1-yl)phenyl)amino)-2-(3-iodobenzyl)-6,9,12,15,18-pentaoxa-2-azahenicosyl)-6-(2-((E)-3,3-dimethyl-5-sulfo-1-(4-sulfobutyl)indolin-2-ylidene)ethylidene)-3,4,5,6-tetrahydro-[1,1'-biphenyl]-2-yl)vinyl)-3,3-dimethyl-5-sulfo-3H-indol-1-ium-1-yl)butane-1-sulfonate (117)

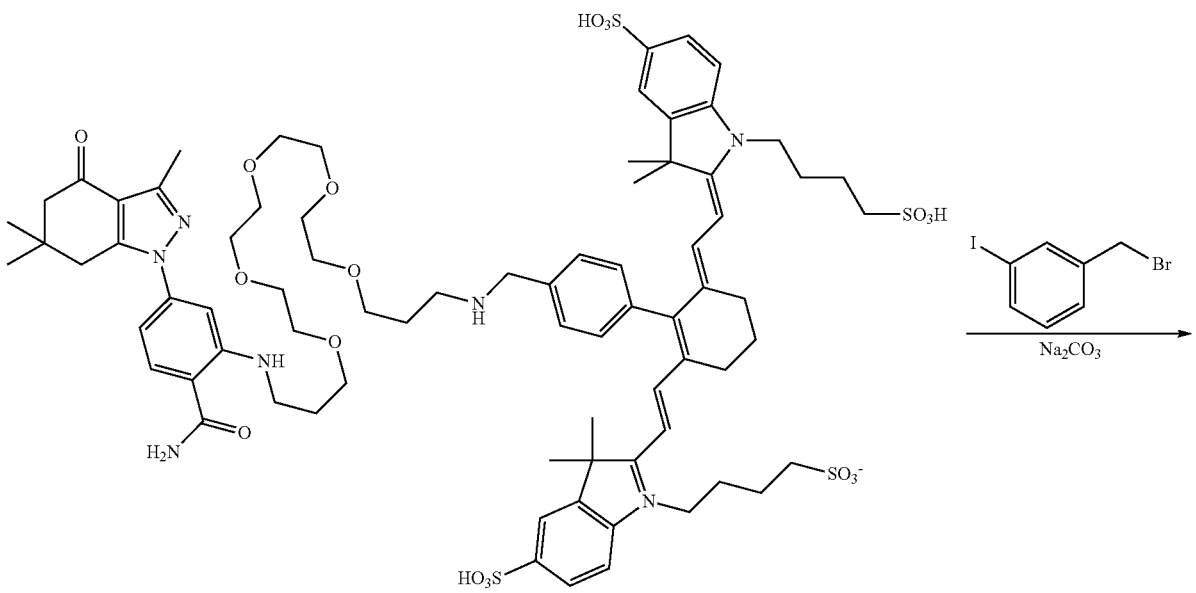

108

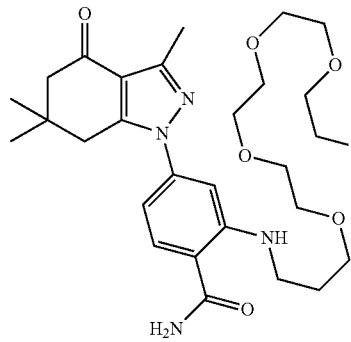
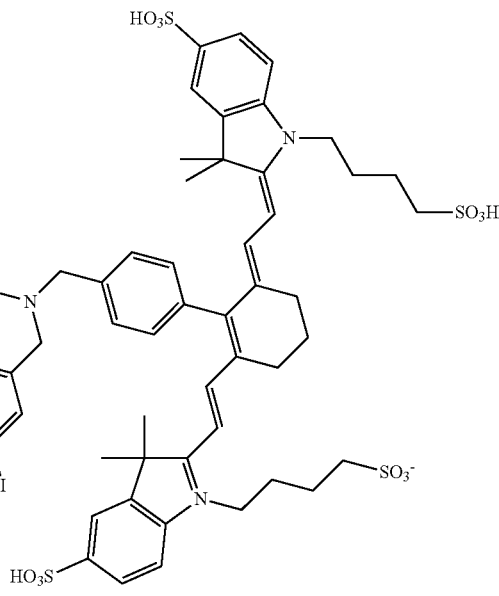

117

Compound 108 (50 mg, 32 μmol), sodium carbonate (11 mg, 97 μmol) and 3-iodobenzyl bromide (11 mg, 36 μmol) were dissolved in methanol (2 mL) and stirred at RT for 2 days. The reaction was mixture was concentrated then dissolved in water and chromatographed (50 g C18, 0.2% formic acid to 100% MeOH) to give the product 117 (37 mg, 65%) as a green solid. $^1$H-NMR (dmso-d$_6$) δ 9.99 (br s, 1H), 8.02 (s, 1H), 7.89 (d, J=8 Hz, 1H) 7.82 (d, J=8 Hz, 2H), 7.75 (d, J=8 Hz, 1H), 7.67 (d, J=8 Hz, 1H), 7.57 (d, J=8 Hz, 2H), 7.53 (s, 2H), 7.42 (d, J=8 Hz, 2H), 7.40 (t, J=8 Hz, 1H), 7.29 (d, J=8 Hz, 2H), 7.04 (d, J=14 Hz, 2H), 6.77 (d, J=2 Hz, 1H), 6.67 (dd, J=2, 8 Hz, 1H), 6.27 (d, J=14 Hz, 2H), 4.60 (s, 2H), 4.40 (s, 2H), 4.09 (br m, 4H), 3.41-3.52 (br m, 20H), 3.20 (t, J=7 Hz, 2H), 2.92 (s, 2H), 2.71 (t, J=7 Hz, 4H), 2.39 (s, 3H), 2.32 (s, 2H), 1.95 (br m, 2H), 1.79 (p, J=7 Hz, 2H), 1.70 (br m, 8H), 1.11 (s, 6H), 1.08 (s, 6H), 1.00 (s, 6H).

Example 20. 4-(2-((E,3Z)-3-(4-(21-((2-carbamoyl-5-(3,6,6-trimethyl-4-oxo-4,5,6,7-tetrahydro-1H-indazol-1-yl)phenyl)amino)-2-(3-(trimethylstannyl)benzyl)-6,9,12,15,18-pentaoxa-2-azahenicosyl)phenyl)-5-((E)-3,3-dimethyl-1-(4-sulfobutyl)indolin-2-ylidene)penta-1,3-dien-1-yl)-3,3-dimethyl-3H-indol-1-ium-1-yl)butane-1-sulfonate (118)

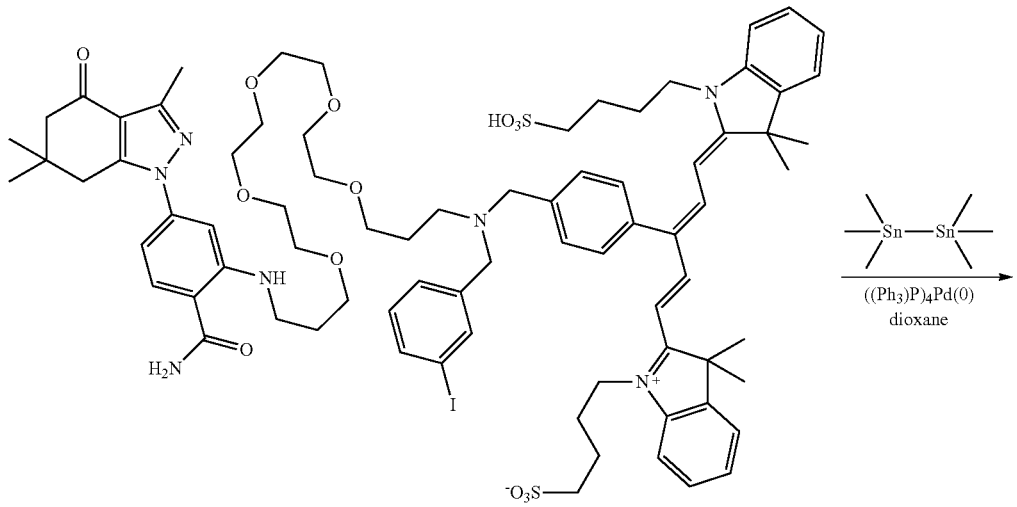

116

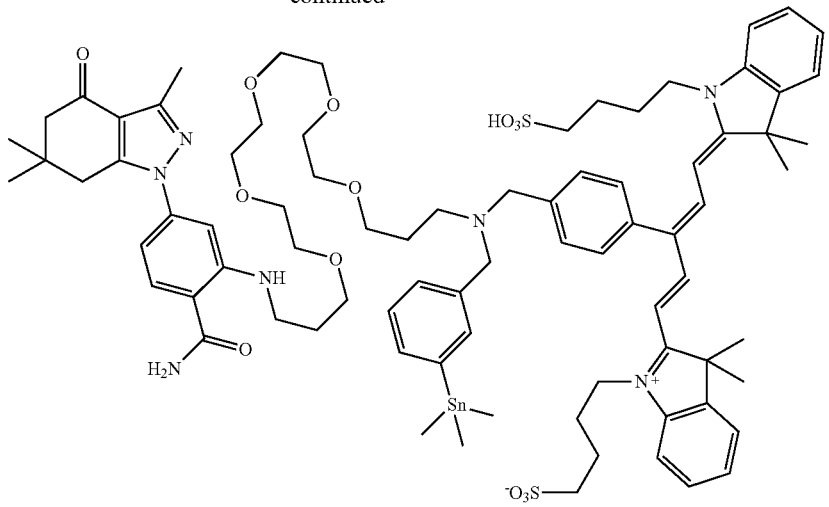

118

Compound 116 (50 mg, 33 μmol), hexamethylditin (14 mg, 9 μL, 42 μmol) and tetrakis triphenylphosphine palladium(0) (1 mg 1 μmol) were slurried in dioxane (1 mL), purged with nitrogen for 30 m and heated to 100° C. for an hour. The reaction was mixture was adsorbed onto silica gel and chromatographed (50 g C18, 0.2% formic acid to 100% MeOH) to give product 118 (13.9 mg, 27%) as a blue solid. LC/MS gives a single peak with a little shoulder with m/z=785.8 [M+2H]$^{2+}$ as part of a cluster typical of Tin compounds. LC/MS at a later date showed significant decomposition, primarily to the hydride.

Example 21. (E)-4-(4-(3',6'-bis(diethylamino)-3-oxospiro[isoindoline-1,9'-xanthen]-2-yl)styryl)-1-(2-(1-(22-((2-carbamoyl-5-(3,6,6-trimethyl-4-oxo-4,5,6,7-tetrahydro-1H-indazol-1-yl)phenyl)amino)-2-oxo-7,10,13,16,19-pentaoxa-3-azadocosyl)-1H-1,2,3-triazol-4-yl)ethyl)pyridin-1-ium (119)

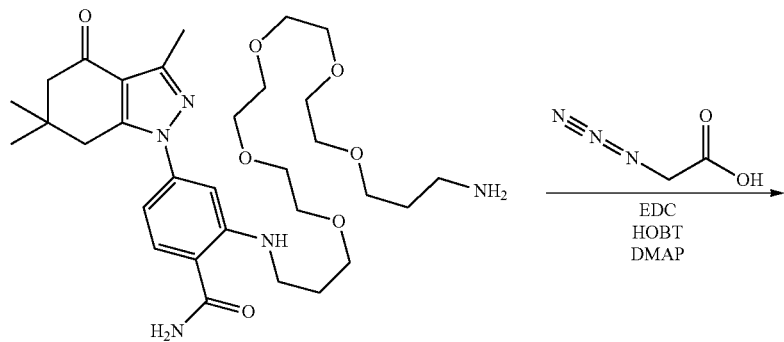

5

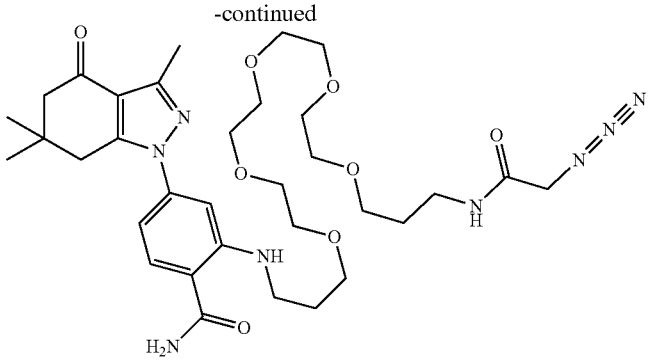

24

Acid 2-azidoacetic acid (37 mg, 358 μmol), amine 5 (180 mg, 298 μmol), HOBT (46 mg, 298 μmol), DMAP (5 mg) and EDC (114 mg, 596 μmol) were dissolved in methylene chloride (2 mL) and stirred for 3 d. The mixture was loaded onto a column and chromatographed (silica gel, 0 to 20% MeOH in CH$_2$Cl$_2$) to give 33 (109 mg, 53%) as a clear oil. LC/MS gave m/z=687.4. [M+1]$^+$. $^1$H-NMR (DMSO-d$_6$) δ 8.41 (br t, J=6 Hz, 1H) 8.06 (br t, J=6 Hz, 1H), 7.92 (br s, 1H), 7.74 (d, J=8 Hz, 1H), 7.26 (br s, 1H), 6.77 (d, J=2 Hz, 1H), 6.68 (dd, J=2, 8 Hz, 1H), 3.78 (s, 2H), 3.43-3.55 (m, 22H), 3.38 (t, J=6 Hz, 2H), 3.21 (q, J=6 Hz, 2H), 3.17 (s, 2H), 3.12 (q, J=6 Hz, 2H), 2.40 (s, 3H), 2.33 (s, 2H), 1.81 (p, J=6 Hz, 2H), 1.63 (p, J=6 Hz, 2H), 1.01 (s, 6H).

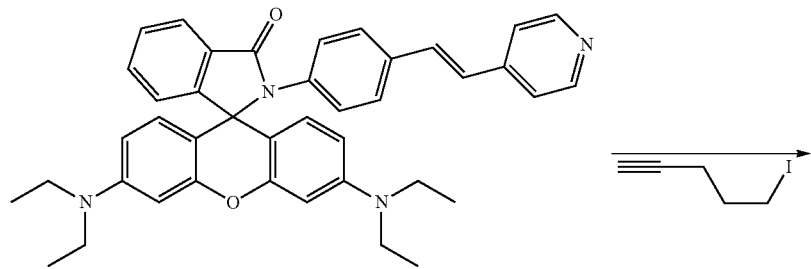

25

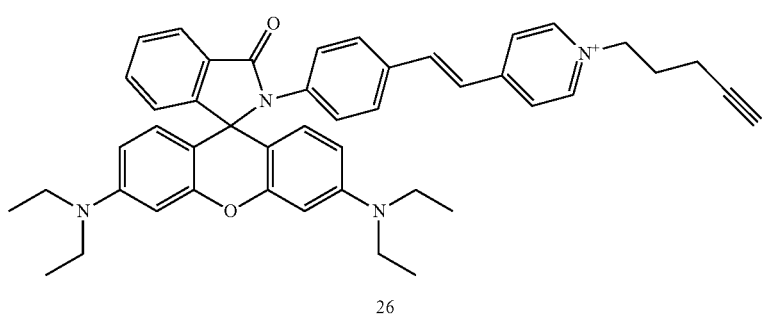

26

A solution of 25 (Moemer et al. J. Am. Chem. Soc. 2014, 136, 14003-14006. 180 mg, 290 µmol) and 5-iodo-1-pentyne (225 mg, 1.16 µmol) in methylene chloride (2 mL) and acetonitrile (1.5 mL) and heated to 70° C. for 16 h. The reaction mixture was then concentrated and chromatographed (silica gel, 0 to 20% MeOH in $CH_2Cl_2$) to 26 (201 mg, 85% as iodide) as an orange solid. $^1$H-NMR (dmso-$d_6$) δ 8.90 (d, J=7 Hz, 2H), 8.13 (d, J=7 Hz, 2H), 7.90 (dd, J=1, 6 Hz, 1H), 7.86 (d, J=16 Hz, 1H), 7.59 (td, J=1, 6 Hz, 1H), 7.56 (d, J=8 Hz, 2H), 7.56 (td, J=1, 6 Hz, 1H), 7.41 (d, J=16 Hz, 1H), 7.09 (d, J=8 Hz, 2H), 7.07 (dd, J=1, 6 Hz, 1H), 6.56 (d, J=9 Hz, 2H), 6.37 (dd, J=2, 9 Hz, 2H), 6.32 (d, J=2 Hz, 2H), 4.53 (t, J=7 Hz, 2H), 3.30 (q, J=7 Hz, 8H), 2.87 (t, J=2.5 Hz, 1H), 2.27 (dt, J=2.5, 7 Hz, 2H), 2.11 (p, J=7 Hz, 2H), 1.06 (t, J=7 Hz, 12H).

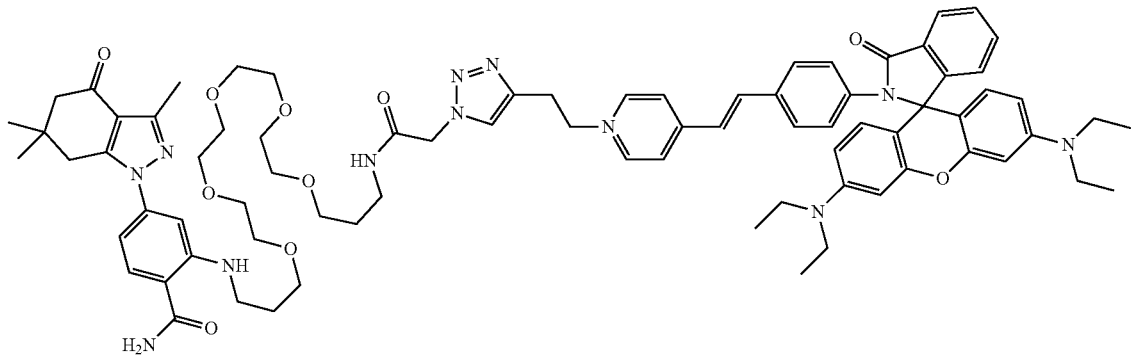

119

(E)-4-(4-(3',6'-bis(diethylamino)-3-oxospiro[isoindoline-1,9'-xanthen]-2-yl)styryl)-1-(2-(1-(22-((2-carbamoyl-5-(3,6,6-trimethyl-4-oxo-4,5,6,7-tetrahydro-1H-indazol-1-yl)phenyl)amino)-2-oxo-7,10,13,16,19-pentaoxa-3-azadocosyl)-1H-1,2,3-triazol-4-yl)ethyl)pyridin-1-ium (119)

Azide 24 (78 mg, 113 µmol) and acetylene 26 (101 mg, 125 µmol) were combined in methylene chloride (1 mL) and treated with Hunig's base (I drop) and CuI (10 mg) and stirred at RT until TLC (9/1: $CH_2Cl_2$/MeOH) showed complete reaction after 16 h. The reaction mixture was concentrated then dissolved in methylene chloride and chromatographed (silica gel, 0 to 25% 9/1: MeOH/$NH_4OH$ in $CH_2Cl_2$) to give product 119 (98 mg, 63%) as an orange crunchy solid. LC/MS gave a broad ms peak with m/z=1373.7 $[M]^+$ and 687.4 $[M+1]^2$. $^1$H-NMR (dmso-$d_6$) δ 8.91 (d, J=6 Hz, 2H), 8.4 (br t, J=5 Hz, 1H), 8.28 (br t, J=5 Hz, 1H), 8.12 (d, J=6 Hz, 2H), 7.93 (br s, 1H), 7.90 (d, J=7 Hz, 1H), 7.85 (d, J=16 Hz, 1H), 7.84 (s, 1H), 7.74 (d, J=8 Hz, 1H), 7.59 (t, J=7 Hz, 1H), 7.56 (d, J=8 Hz, 2H), 7.55 (t, J=7 Hz, 1H), 7.40 (d, J=16 Hz, 1H), 7.27 (br s, 1H), 7.09 (d, J=8 Hz, 2H), 7.06 (d, J=7 Hz, 1H), 6.77 (d, J=2 Hz, 1H), 6.67 (dd, J=2, 8 Hz, 1H), 6.56 (d, J=9 Hz, 2H), 6.37 (dd, J=2, 9 Hz, 2H), 6.32 (d, J=2 Hz, 2H), 5.00 (s, 2H), 4.55 (t, J=7 Hz, 2H), 3.42-3.53 (m, 22H), 3.38 (t, J=6 Hz, 2H), 3.3 (q, J=7 Hz, 8H), 3.2 (q, J=6 Hz, 2H), 3.12 (q, J=6 Hz, 2H), 2.92 (s, 2H), 2.68 (t, J=6 Hz, 2H), 2.39 (s, 3H), 2.32 (s, 2H), 2.26 (p, J=6 Hz, 2H), 1.8 (p, J=6 Hz, 2H), 1.63 (p, J=6 Hz, 2H), 1.06 (t, J=7 Hz, 12H), 1.00 (s, 6H).

Example 22. Synthesis of (S)-1-((2-carbamoyl-5-(3,6,6-trimethyl-4-oxo-4,5,6,7-tetrahydro-1H-indazol-1-yl)phenyl)amino)-24-(4-(((2,4-diaminopteridin-6-yl)methyl)(methyl)amino)benzamido)-21-oxo-4,7,10,13,16-pentaoxa-20-azapentacosan-25-oic acid (120)

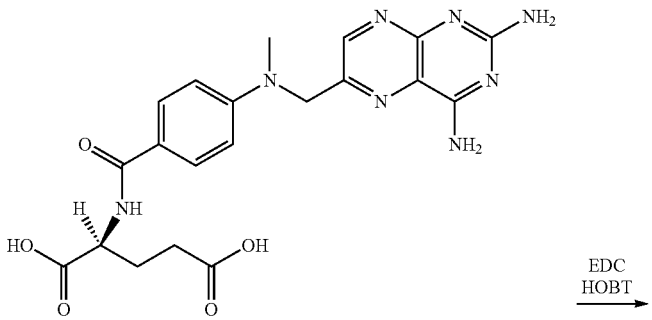

27

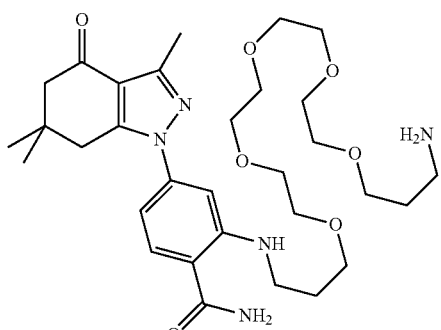
5
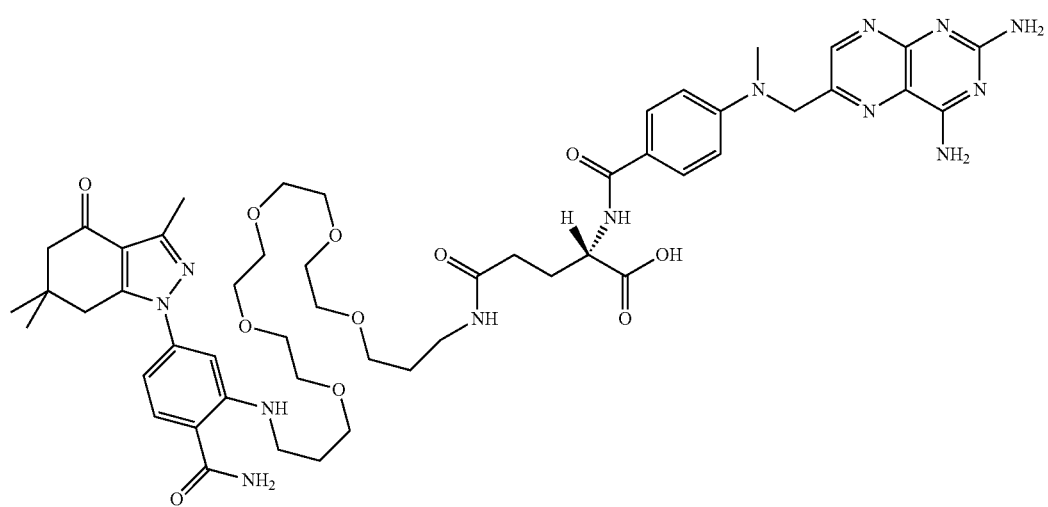
120

Amine 5 (36 mg, 60 μmol), methotrexate 27 (MTX, 36 mg, 80 μmol) and HOBT (9 mg, 63 μmol) were dissolved in DMF (0.5 mL) and then treated with EDC (14 mg, 72 μmol) in DMF (150 μL). After one day the mixture was injected onto a prep HPLC (Agilent Prep C-18, 2.5×25 cm, 5 to 100% MeOH w/2% formic acid, prep run data lost) and the product collected to give 38 (40 mg, 64%) as a yellow glass. LC/MS gave m/z=1040.6 [M+1]$^+$.

Example 23. Synthesis of (5R,8S,11R,12S,15S,18R, 19S,22R)-2-(((3-((3-(3-((2-carbamoyl-5-(3,6,6-trimethyl-4-oxo-4,5,6,7-tetrahydro-1H-indazol-1-yl)phenyl)amino)propoxy)propyl)amino)-3-oxopropyl) thio)methyl)-15-(3-guanidinopropyl)-8-isobutyl-18-((1E,3E,5S,6S)-6-methoxy-3,5-dimethyl-7-phenylhepta-1,3-dien-1-yl)-1,5,12,19-tetramethyl-3, 6,9,13,16,20,25-heptaoxo-1,4,7,10,14,17,21-heptaazacyclopentacosane-11,22-dicarboxylicacid (121)

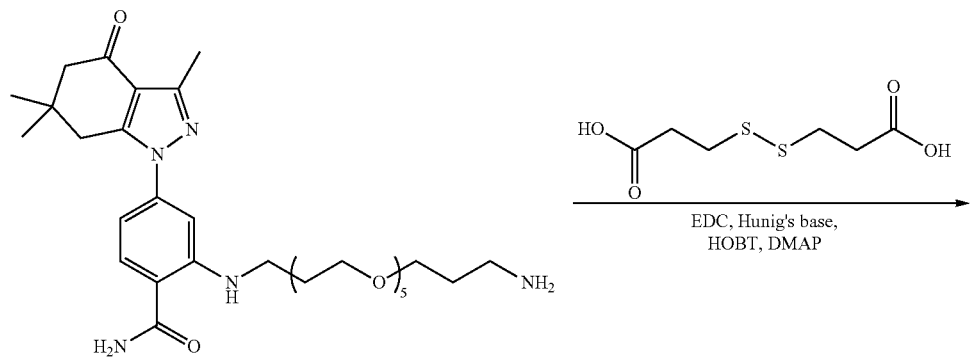

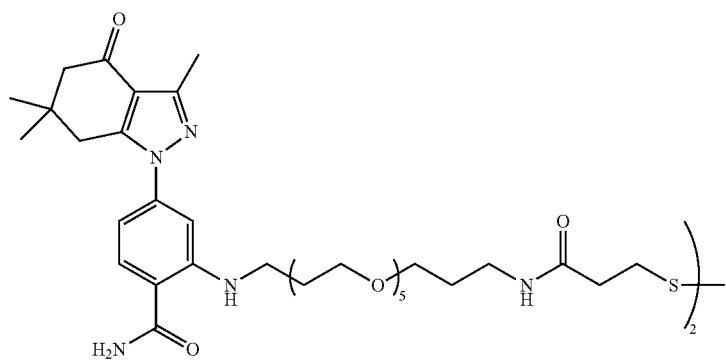

2,2'-((21,28-dioxo-4,7,10,13,16,33,36,39,42,45-decaoxa-24,25-dithia-20,29-diazaoctatetracontane-1,48-diyl)bis(azanediyl))bis(4-(3,6,6-trimethyl-4-oxo-4,5,6,7-tetrahydro-1H-indazol-1-yl)benzamide) 28

Amine 5 (2242 mg, 400 μmol), 3,3'-dithiodipropionic acid (42 mg, 200 μmol), Hunig's base (78 mg, 600 μmol), HOBT (27 mg, 200 μmol) and DMAP (3 mg) were dissolved in methylene chloride (2 mL) and treated with EDC (115 mg, 600 μmol) and stirred at RT for 2 days. The mixture was passed through silica gel (4/1. $CH_2Cl_2$/MeOH), concentrated and purified by prep HPLC (30 to 100% methanol, 20 mL/m, Agilent C-18, 21.1×25 cm) to give disulfide 28 (96 mg. 35%) as an oil. LC/MS gave m/z=11381.6 $[M+1]^+$. $^1$H-NMR (dmso-$d_6$) δ 8.41 (br t, J=5 Hz, 1H), 7.92 (br s, 1H), 7.90 (br t, J=5 Hz, 1H), 7.74 (d, J=8 Hz, 1H), 7.27 (br s, 1H), 6.77 (d, J=2 Hz, 1H), 6.67 (dd, J=2, 8 Hz, 1H), 3.42-3.53 (m, 20H), 3.37 (t, J=6 Hz, 4H), 3.20 (q, J=6 Hz, 2H), 3.07 (q, J=6 Hz, 2H), 2.92 (s, 2H), 2.86 (t, J=7 Hz, 2H), 2.43 (t, J=7 Hz, 2H), 2.40 (s, 3H), 2.32 (s, 2H), 1.81 (p, J=6 Hz, 2H), 1.60 (p, J=6 Hz, 2H), 1.01 (s, 6H).

Disulfide 28

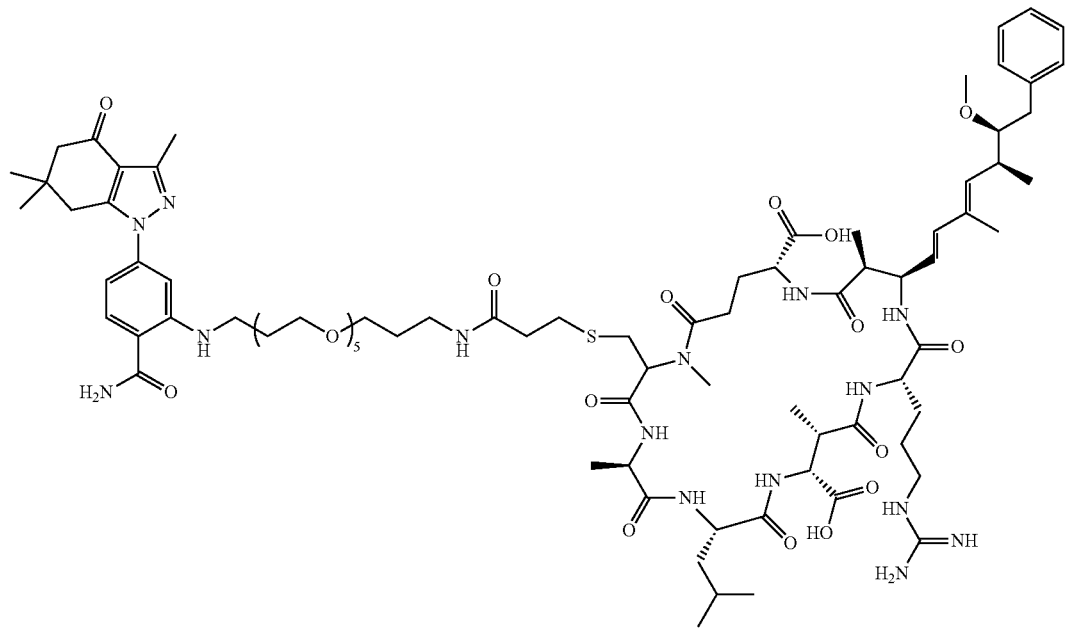

121

The disulfide 28 (0.6 mg, 430 nmol, 10% in ethanol, 6 μL) and TCEP (90 μg, 300 nmol, 1% in water, 8 μL) were combined with a little more ethanol (10 μL) and left overnight. The next day microcystin LR (0.22 mg, 220 nmol, 200 μL of 1 mg/mL) was added. LC/MS showed thiol, MC LR and a trace of disulfide. Hunig's base (0.39 mg, 3 μmol, 4 μL of 10% solution) was then added. After 1 day, the LC/MS looked about the same as before except for a very minor blip with m/z=844.0 at 11 minutes (MC at 10, thiol at 11.5 m). More Hunig's base (25 μL of 10% in EtOH) was added and the sample was concentrated to a glass then taken up in EtOH (25 μL). After another day, LC/MS shows a small but perceptible increase in product. The sample was concentrated to a glass. After another day, LC/MS looks real good. No Microcystin and the little peak has grown up to be a big peak. So now there is a bunch of disulfide, a bit of thiol and a comparable bit of product 121, at least by mass spect (m/z=844.0, $[M+2]^{2+}$).

Example 24. Synthesis of (14S,16S,32S,33S,2R,4S, 10E,12E,14R)-86-chloro-14-hydroxy-85,14-dimethoxy-33,2,7,10-tetramethyl-12,6-dioxo-7-aza-1(6,4)-oxazinana-3(2,3)-oxirana-8(1,3)-benzenacyclotetradecaphane-10,12-dien-4-yl N-(3-((1-(3-(3-((2-carbamoyl-5-(3,6,6-trimethyl-4-oxo-4,5,6,7-tetrahydro-1H-indazol-1-yl)phenyl)amino)propoxy)propyl)-2,5-dioxopyrrolidin-3-yl)thio)propanoyl)-N-methyl-L-alaninate (122)

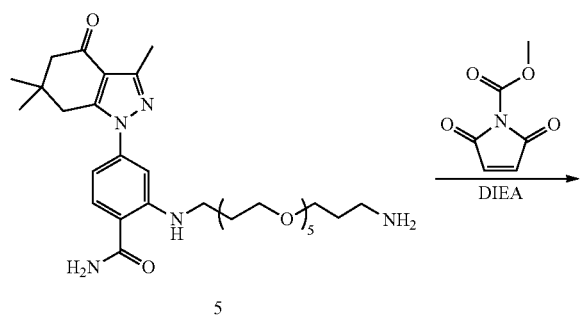

5

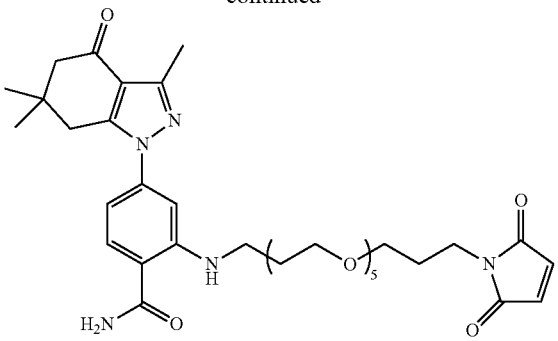

29

Amine 5 (366 mg. 606 μmol), Hunig's base (314 mg, 2.43 μmol) and methoxycarbonylmaleimide (104 mg, 667 μmol) were dissolved in dichloroethane (5 mL) and heated at 70° C. After twenty hours, the mixture was concentrated and chromatographed (silica gel, 0 to 10% MeOH in $CH_2Cl_2$) to give maleimide 29 (227 mg, 54%) as a glass. LC/MS gave a single peak with m/z=684.3 [M+1]$^+$, $^1$H NMR (DMSO-$d_6$) δ 8.41 (t, J=5 Hz, 1H), 7.92 (br s, 1H), 7.74 (d, J=8 Hz, 1H), 7.26 (br s, 1H), 6.99 (s, 2H), 6.77 (d, J=2 Hz, 1H), 6.67 (dd, J=2, 8 Hz, 1H), 3.3.38-3.53 (m, 20H), 3.35 (t, J=6 Hz, 2H), 3.2 (q, J=6 Hz, 2H), 2.92 (s, 2H), 2.4 (s, 3H), 2.33 (s, 2H), 1.81 (p, J=6 Hz, 2H), 1.69 (p, J=6 Hz, 2H), 1.01 (s, 6H).

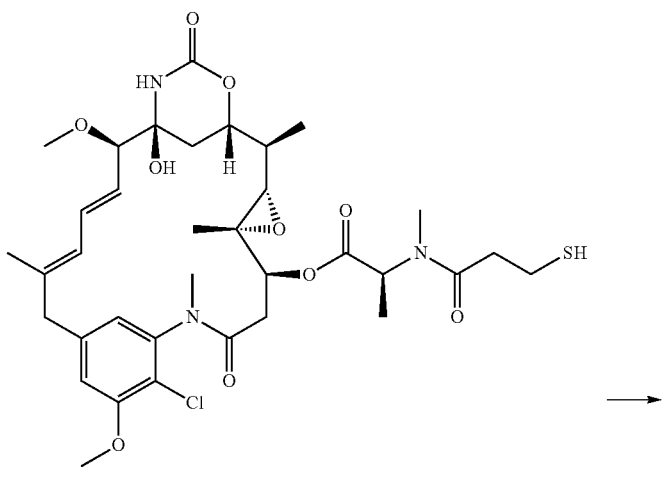

DM-1

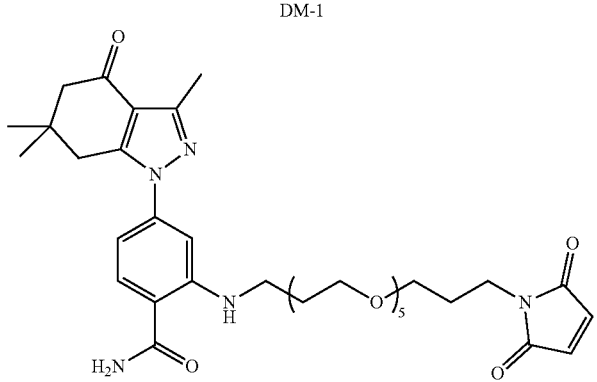

29

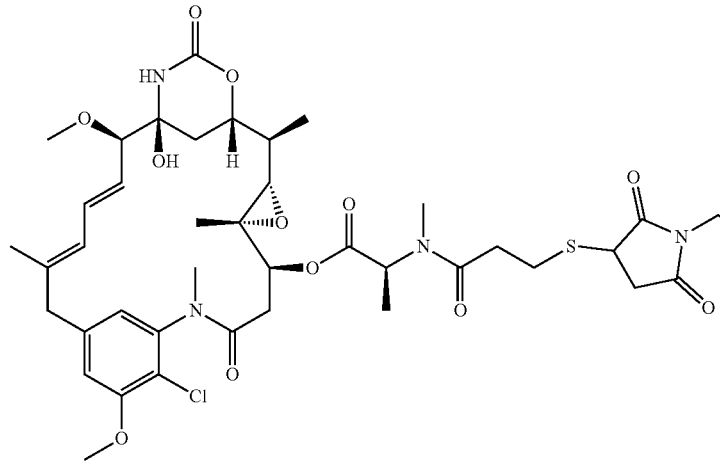
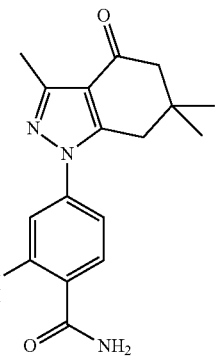

122

Maleimide 29 (111 mg, 163 μmol) was dissolved in acetonitrile (3 mL) and added to solid DM-1 (from Genentech, 100 mg, 135 μmol) and stirred at RT for one day. The mixture was concentrated and chromatographed (silica gel, 0 to 10% MeOH in $CH_2Cl_2$) to give product 122 (144 mg, 75%) as a white crunchy powder. LC/MS gave a single peak with m/z=1421.5 $[M+1]^+$.

Example 25. Tumor Cell-Specific eHsp90 Internalization

Figure 2A:
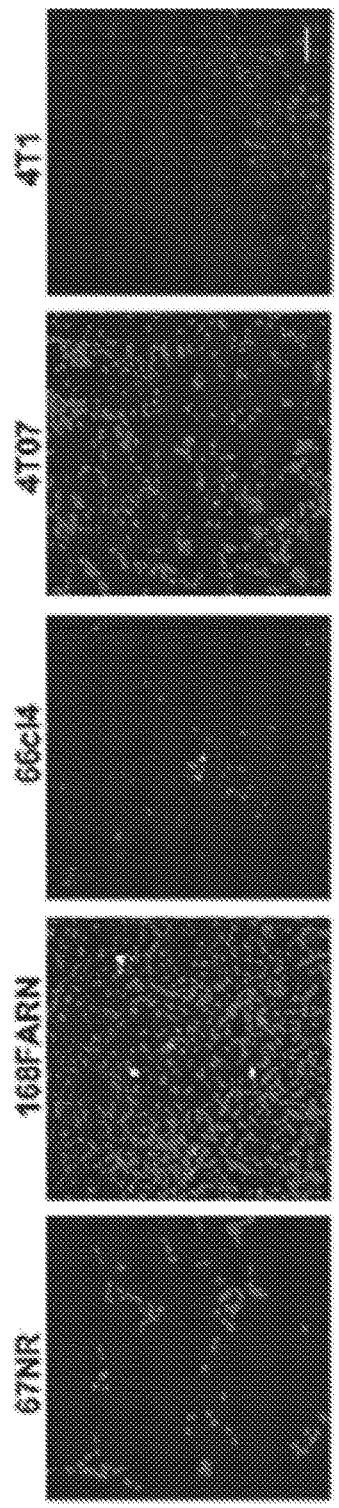
FIG. 2. 100 is a fluorescent specific small-molecule Hsp90 inhibitor. (a) Internalization of 100 (25 μM, 45 min) in 67NR, 168FARN, 66c14, 4T07, and 4T1 cells, quantified in (b); scale bar=50 μm. (c) Dose-dependent internalization of 100 and 101 in MDA-MB-468 cells. (d) 100 is internalized in a time-dependent manner. (e) Fluorescence of 100-treated MDA-MB-468 cells (25 μM, 45 min) in competition with 1 μM HS-10 or 10 μM PUH71. (f) Biotinylated eHsp90 is detected via Western blot. BT, total biotinylated lysate, and Bs, biotinylated lysate from stripped cells. Cells were incubated at 37° C. to stimulate endocytosis, cooled, and stripped of external biotin. **, $p<0.001$, univariate ANOVA with Bonferroni's post-hoc test. Data are represented as the means±SEM.
Figure 2B:
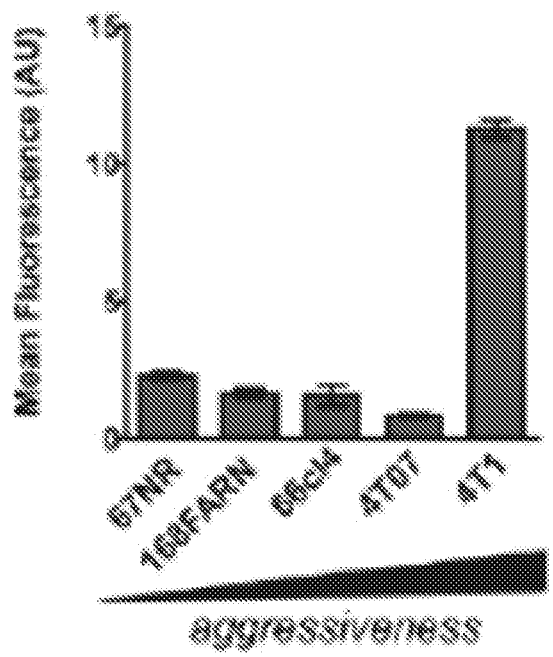
Figure 2C:
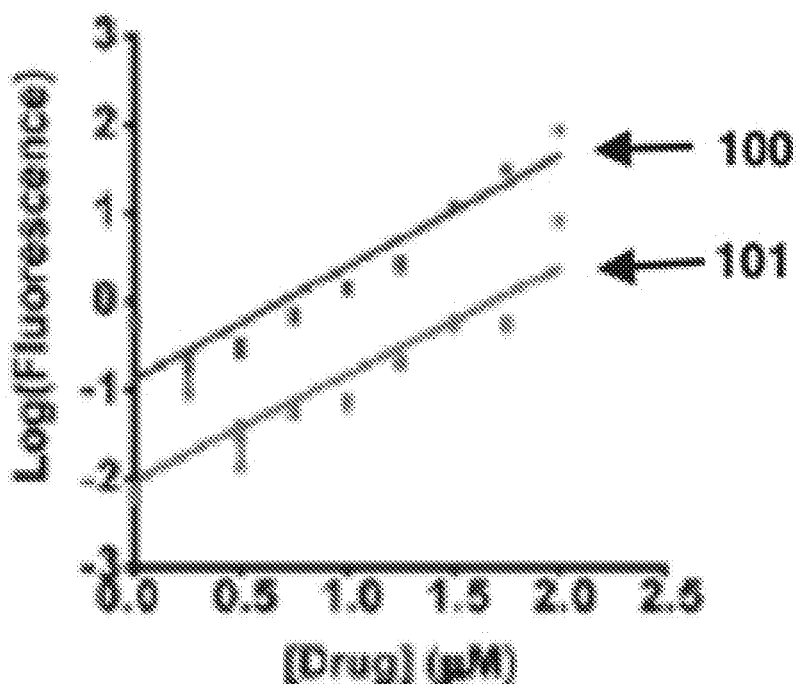
Figure 2D:
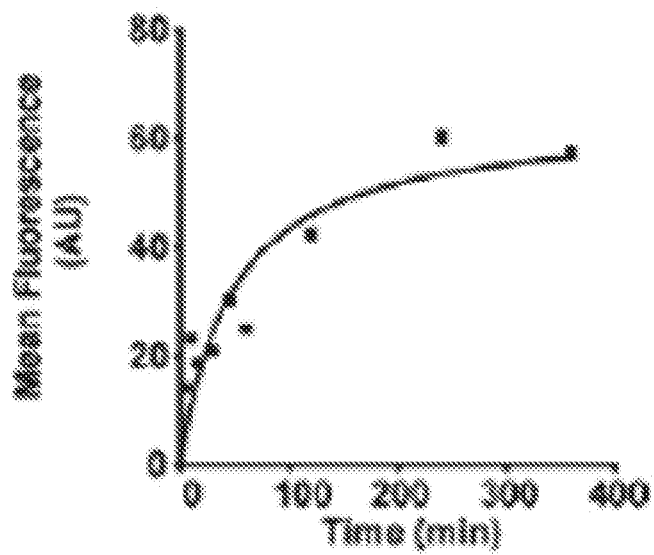
Figure 2E:
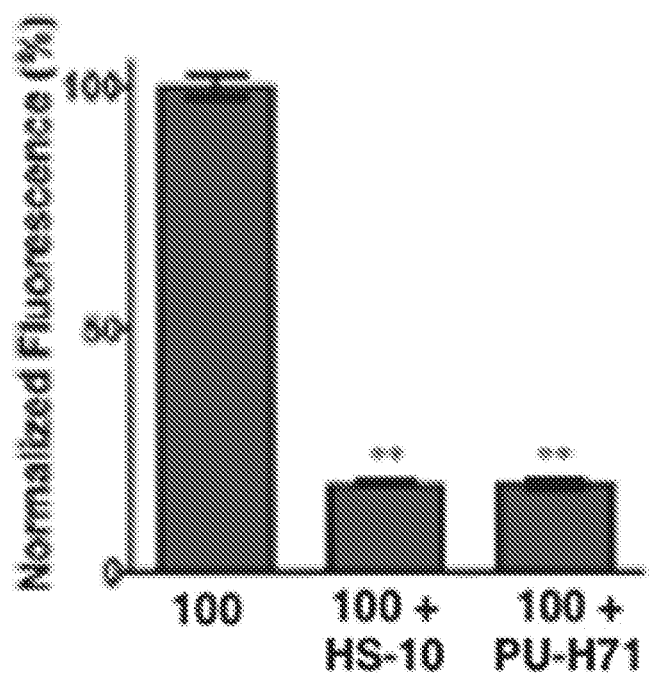
Figure 2F:
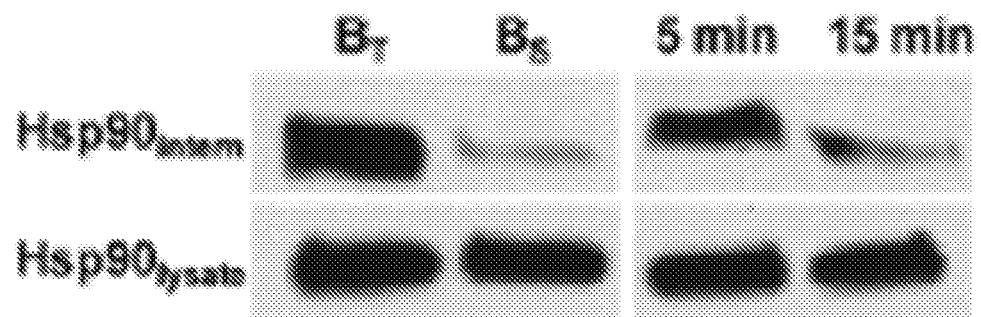

Because 100 is not cell permeable, it binds exclusively to eHsp90, providing specific access to this particular pool of one of the most abundant proteins in the cell. To analyze the internalization of eHsp90 in transformed cells, the 4T1 cell model was utilized. The five isogenic cell lines (67NR, 168FARN, 4T07, and 4T1) were isolated from a single spontaneous mammary tumor and exhibit varying degrees of metastatic disease when injected into mice. 100 was internalized to a higher extent in 4T1 cells (the most aggressive of the five lines) over the less metastatic lines (FIG. 2a, b). In MDA-MB-468 cells, uptake of 100 was dose- and time-dependent (FIG. 2c, d), and binding of the probe to eHsp90 was competed with HS-10 and PUH71 (FIG. 2e). In contrast, the inactive analog 101 was only weakly internalized at higher concentrations (FIG. 2c).

Example 26. eHsp90 Aggregation into Puncta Prior to Internalization

Figure 3A:
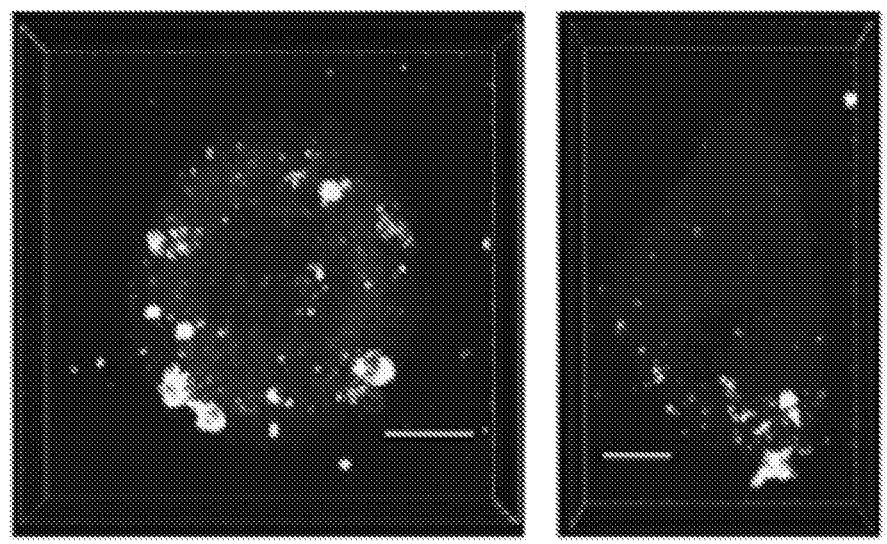
FIG. 3. 100 accumulates into Hsp90-positive puncta within the cell and can be induced by transformation of non-malignant cells results. (a) Three-dimensional confocal images of MDA-MB-468 cells expressing 100-positive puncta after a 45 min treatment with 25 μM 100. Scale bar, 5 μm. (b) Number of puncta/cell of MDA-MB-468 cells treated with 25 μM 100 at increasing time points. (c) 100 fluorescence and Hsp90 immunoreactivity on the surface of a non-permeabilized MDA-MB-468 cell. Membrane is labeled green. (d) Number of moving puncta (tracks) detected in cells treated with 10 μM 100 or 101, or 100 competed with 100 μM HS-10. (e) Fluorescence of 100 internalization (25 μM, 45 min incubation) after treatment with endocytotic inhibitors. CytoD, cytochalasin D, 2 μM; EIPA, 5-(N-Ethyl-N-isopropyl)amiloride, 25 μM; PitStop2, 25 μM; Filipin III, 5.0 μg/mL. (f) Representative Western blot of MCF10A clones showing HER2 and Hsp90 expression. GAPDH was used as an internal loading control. (g) Growth foci in MCF10A cells overexpressing full-length HER2, p110HER2, or p110HER2KD induced with doxycycline. (h) Representative fluorescence images of MCF10A mutants treated with 25 μM 100 for 45 min. (i) Quantification of 100 fluorescence taken as a ratio of doxycycline-treated cells to non-induced cells. *, $p<0.05$; **, $p<0.001$, univariate ANOVA with Bonferroni's post-hoc test. Data are represented as the means±SEM. See also FIG. S3.
Figure 3B:
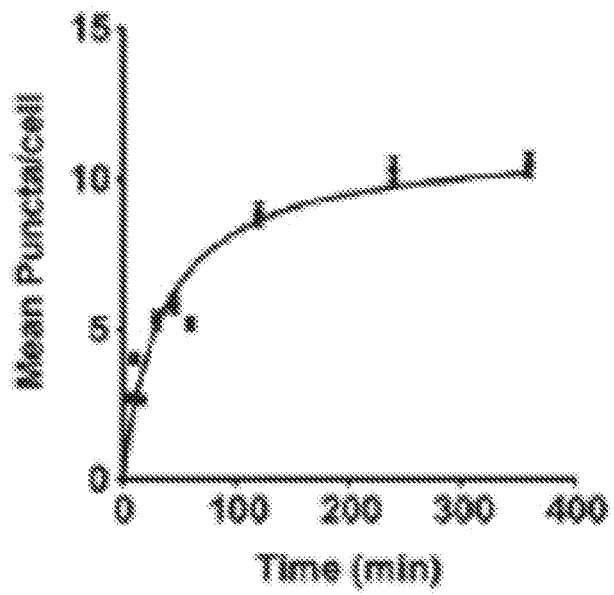

High resolution confocal images of 100-treated cells revealed striking punctate formations both on the cell surface and within the cell itself, as well as diffuse fluorescence throughout the cell (FIG. 3a). Close examination of the larger structures shows that the average size of these puncta are 0.95±0.04 μm³ with an average fluorescence intensity of 33.01±10.37 units. Using a standard fluorescence curve, the concentration within the puncta of 100 was estimated to be 4.66±0.05 μM. Based on puncta volume and a ratio of 1:1 for 100:Hsp90 (as each monomer of Hsp90 has a single ATP-binding site), the larger puncta are estimated to contain 2659±105 monomers of eHsp90. Accumulation of the puncta intracellularly is time-dependent (FIG. 3b). Formation of the puncta is eHsp90-dependent and not related to any physiochemical properties of the probes themselves. This was demonstrated in multiple ways; first, 19, the tethered fluorophore without the ligand, does not form puncta when applied to cells; second, HS-27, a FITC-tethered Hsp90 inhibitor with a fluorophore moiety structurally unrelated to the Cy5 based fluorophore used in 100, forms puncta when applied to tumor cells; thirdly, binding of 100 and HS-27 to eHsp90 is blocked by structurally distinct untethered Hsp90 inhibitors such as SNX2112, HS-10, Ganetespib, Geldanamycin and PUH71; fourth, puncta do not form on non-malignant cells in the presence of 100 or HS-27. Additionally, formation of the puncta is reversible within cells; internal puncta number decrease after drug removal, and diffuse fluorescence can be observed throughout the cell (FIG. 2a). This diffusion may be a result of exchange with intracellular ATP or the degradation of the internalized eHsp90. Probe aggregates alone would not be expected to spontaneously dissipate without the addition of some form of organic solvent.

Figure 3C:
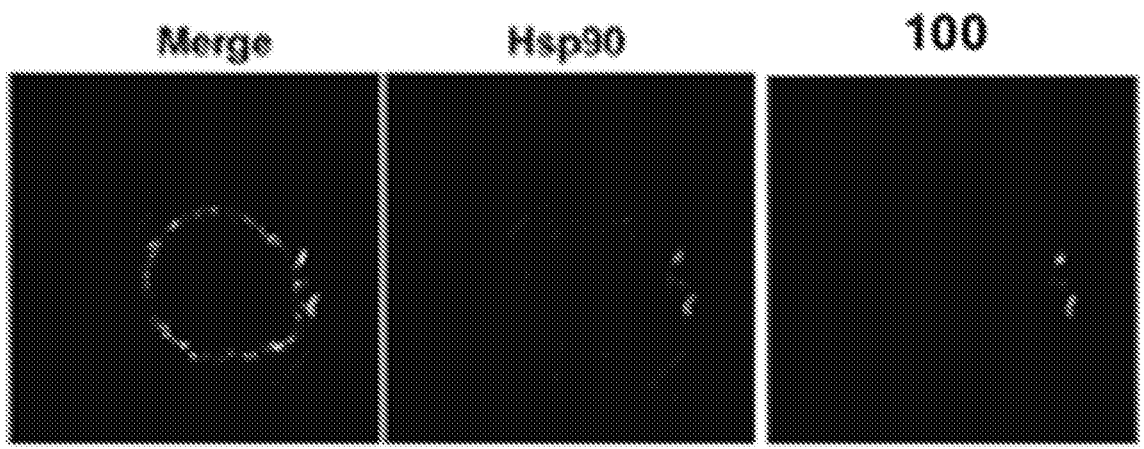
Figure 3D:
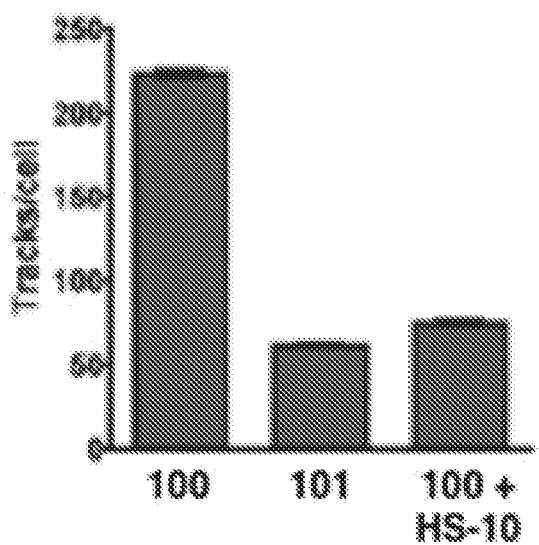
Figure 3E:
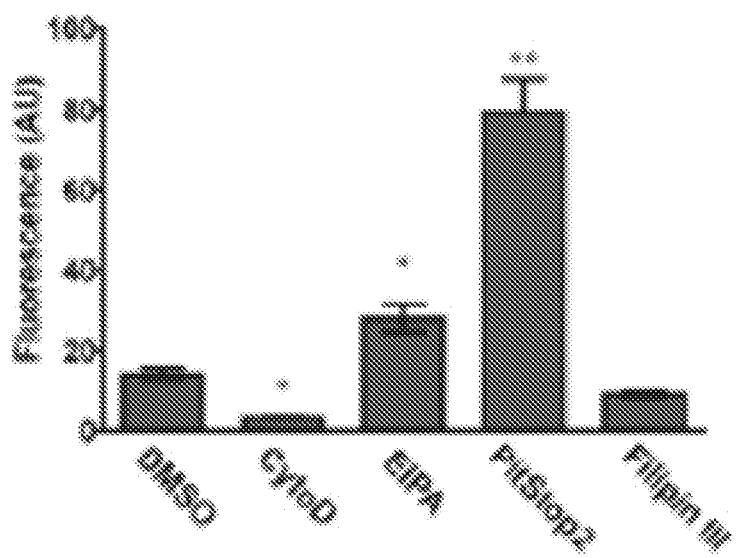

Live imaging of cells treated with 100 with a lattice light sheet microscope shows puncta traveling throughout the cell, consistent with active trafficking. Interestingly, whereas some puncta are stationary, others move rapidly through the cell. The finding that the puncta can also be seen in live imaging experiments and that some puncta are clearly more mobile than others suggests that their formation is part of an organized biological process rather than an in vivo artifact of probe addition. Live imaging was also performed on cells treated with 100 alone, 101, or 100 and HS-10, and spots were tracked over time to investigate any differences in puncta movement and size. Outside of significantly more puncta being detected with 100, puncta size and speed of movement did not appear to be affected, even with the lower affinity 101. Puncta detected with 100 were competed with HS-10 (FIG. 3d). No puncta were observed to travel to or within the nucleus. Importantly, puncta formation requires a live cell because simply incubating highly purified Hsp90 with 100 alone does not cause the protein to spontaneously aggregate as determined by gel filtration or other forms of chromatography. The puncta are therefore a natural phenomenon occurring in live malignant cells only that have been revealed by the 100 probe.

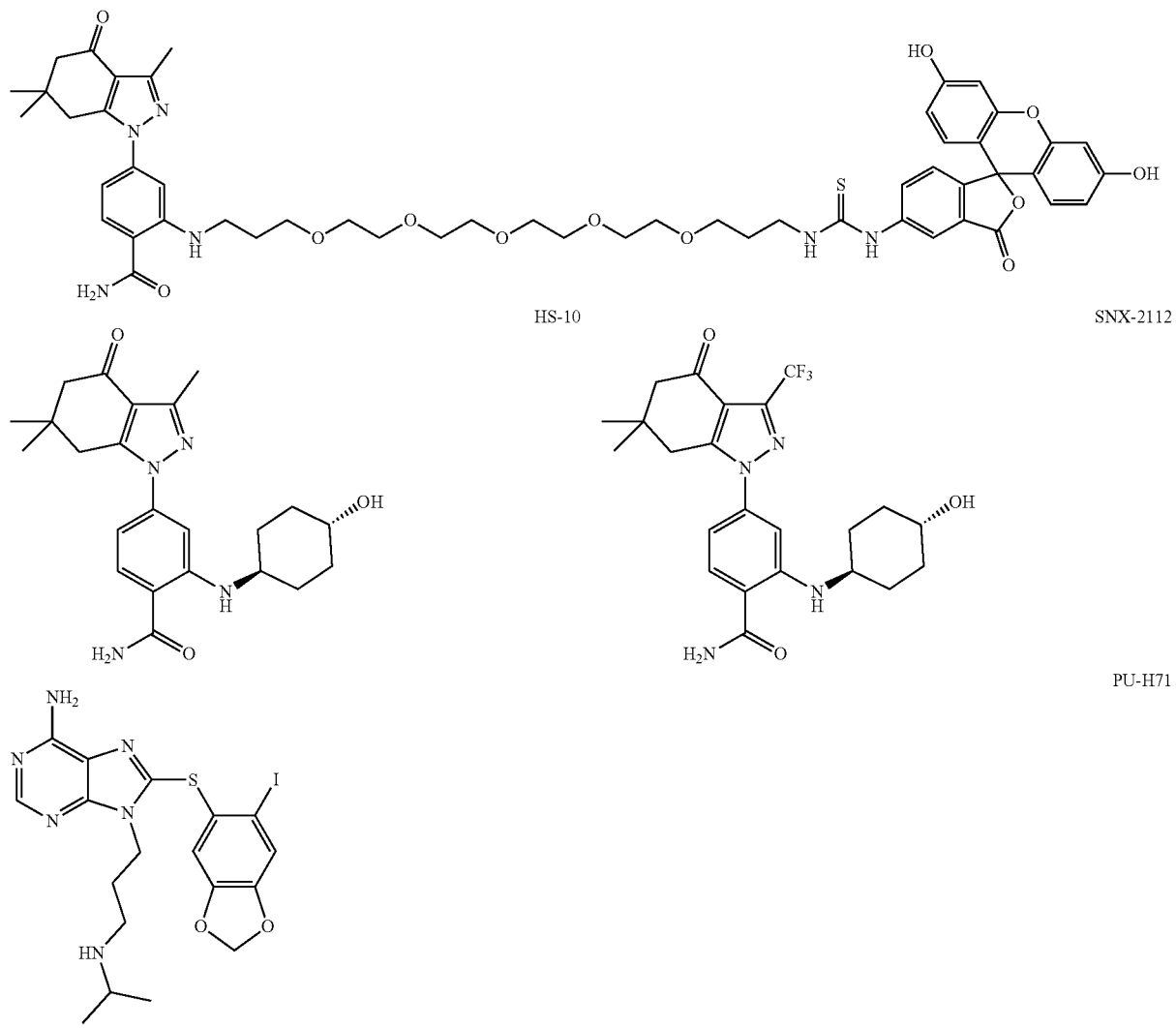

Puncta were not revealed using Hsp90 antibodies alone. Several reasons are likely to account for this; foremost antibodies are twice the molecular size of eHsp90, in contrast to HS131 which 1/100$_{th}$ the molecular size of the protein. Antibody binding is therefore likely to sterically hinder puncta formation, perhaps explaining why Hsp90 antibodies when added to intact tumor cells block fluorophore-tethered Hsp90 internalization. Additionally, puncta formation is likely to hide antigenic epitopes on most of the aggregated eHsp90. By contrast, 100 binding occurs within the active site of the eHsp90 and presumably every protein within the aggregate. The small molecular size of 100 also affords better molecular resolution on a molar basis that could never be achievable with a large molecule such as an antibody. 100 co-localizes with eHsp90 using antibodies when added after the probe. Cells were cooled to 4° C. to halt endocytosis, treated with 100, fixed, then stained with Hsp90 antibodies without being permeabilized to allow the antibodies to react only with surface eHsp90 (FIG. 3c).

Figure 3F:
Figure 3G:
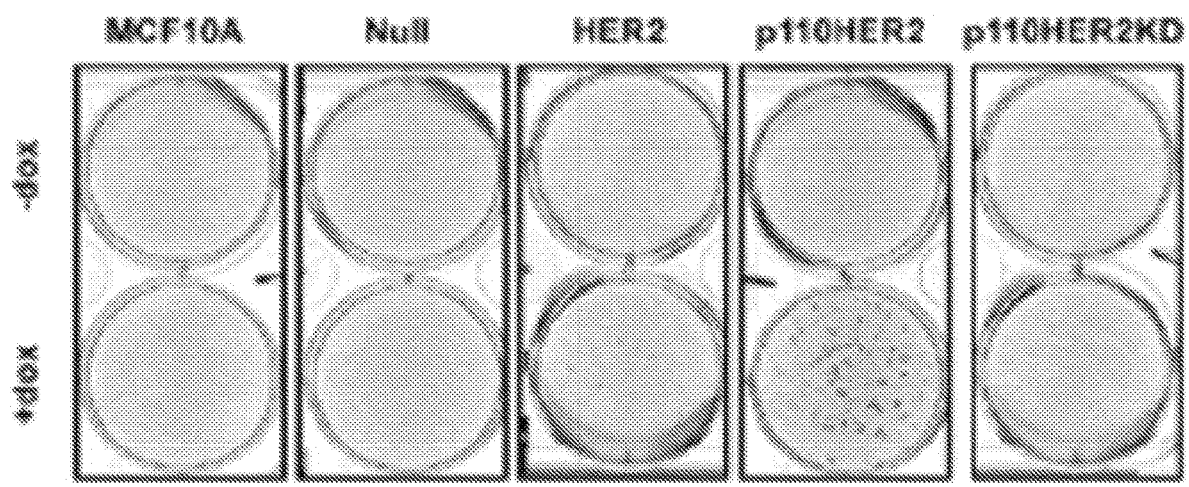
Figure 3H:
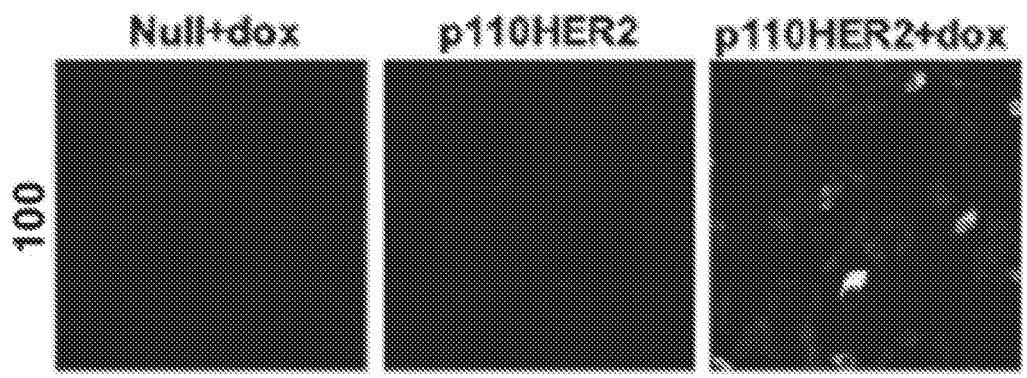
Figure 3I:
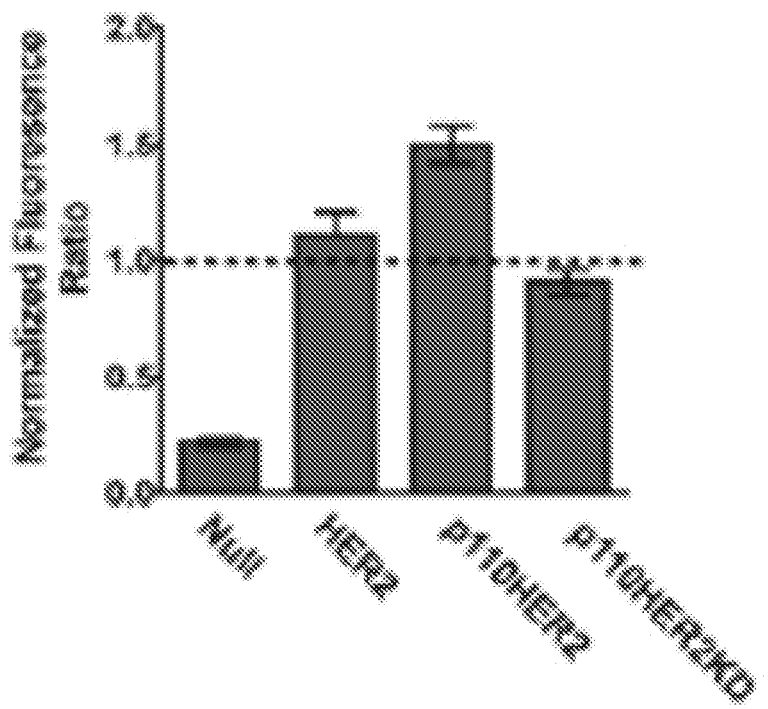

Example 27. Transformation of Non-Malignant Breast Cells Increases Hsp90 Internalization In previous reports, and as shown in FIG. 2a, expression of eHsp90 correlates with malignant phenotypes in cancer lines. However, all cancers are derived from the transformation of non-malignant normally functioning cells. MCF10A cells, a benign human breast epithelial cells that minimally internalize 100 compared with malignant breast cells, were transformed through the stable infection of a construct encoding a doxycycline-inducible p110HER2. Upon induction of p110HER2 expression, MCF10A cells exhibited a transformed phenotype as demonstrated by increased growth foci and showed a significant increase in 100 internalization (FIGS. 3f-i). Expression of p110HER2 also increased Hsp90 expression. Whereas overexpression of a kinase-dead version of p110HER2 did increase Hsp90 expression, it did not exhibit a transformed phenotype nor did it promote internalization of 100 (FIG. 3f, g, i). Since none HER2 dependent breast tumor cells (e.g. MDA-MB- 468 and 4T1) also form puncta and internalize 100 these results suggest that eHsp90 trafficking is part of a larger oncogenic process.

Example 28. Whole Mouse 3D Cryo-Imaging and Histology Demonstrates that Expression of eHsp90 is a Phenomenon of Tumorigenicity Studies in cells suggest that aggressive tumor cell lines, almost exclusively, express eHsp90; however, the body is comprised of hundreds of distinct cells with specific functions, in specific microenvironments and under constant homeostatic surveillance. The majority of cells are fully differentiated and not actively dividing, whereas some subpopulations of cells are constantly undergoing division and growth, such as the endothelial layer lining the intestinal tract. To determine if non-tumor cells express/internalize eHsp90, 3D cyrosectioning of mice bearing MDA-MB-468 flank tumors 6 hours post 100 injection was carried out. Probe uptake into the tumor in the live animal was first confirmed in a Licor instrument.

Figure 4A:
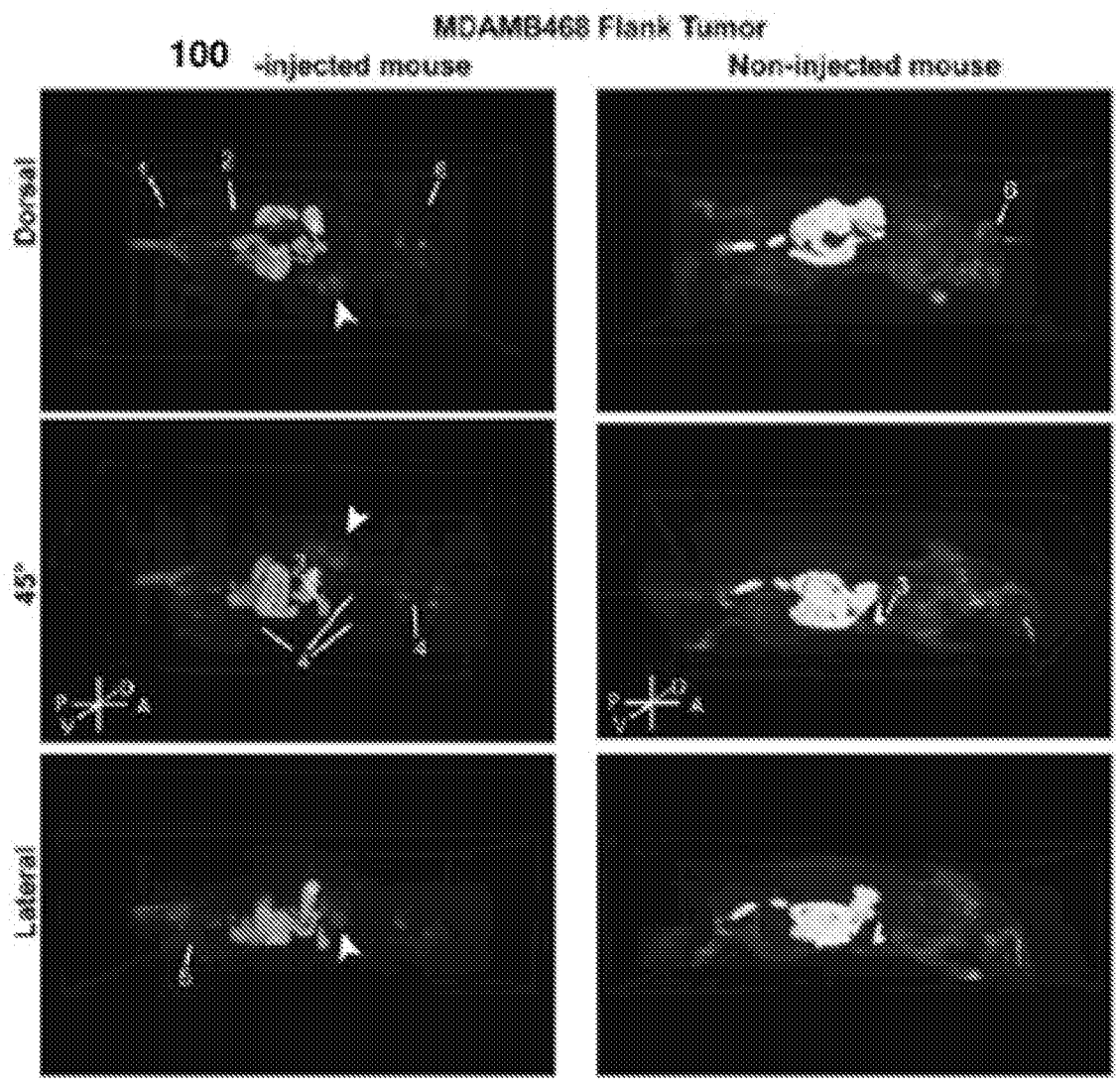
FIG. 4. 100 can be visualized in tumors in vivo. (a) Left: Mouse with right flank xenograft tumor formed from MDA-MB-468 cells. Right: control mouse (no tumor or drug treatment). Arrowhead, tumor; 1, injection site; 2, bladder; 3, gallbladder; 4, lymph nodes; 5, testes; 6, Harderian glands. (b) Fluorescence and brightfield images in representative 40-μm section of tumor and other organs; LN, lymph node. (c) Top: 100-treated MMTV-neu mouse with spontaneous tuor near left rear leg. Bottom: 101-treated MMTV-neu mouse with spontaneous tumor on bottom right abdomen. Arrowheads indicate tumor location. (d) Cross-section of tumor with drug fluorescence. See also Movies S3-S5.

Whereas fluorophore-tethered probes are useful for detecting and following uptake of tumors on the skin surface in live animals, even with the most sensitive of far red or nIR detectors, due to light scattering, detection of emitted fluorescent light is limited to a depth of few mm of tissue. However, when used in conjunction with live imaging, 3D cryosectioning enables the biodistribution of fluorescent probes to the histological level throughout the body. Following sacrifice the animal was cryopreserved in liquid $N_2$, then longitudinal cryosectioned at 40-μm slices. Each slice was imaged for fluorescence with an mCherry band filter (excitation 550-590 nm, emission 600-670 nm) as well as bright field (all slice image data can be down loaded at https://goo.gl/Z30dXJ). The images were reconstructed to create a 3D fluorescence and bright field images of the entire mouse anatomy (FIG. 4a). This process allowed for the first time a detailed examination of the complete biodistribution of 100 at the histological level in every organ. A control non-treated mouse was also imaged using an EGFP-mCherry dual band filter set. The limits of detection of 100 by fluorescence are estimated to be at <1-2 μmol. In a parallel study, an MS analysis was conducted on specific fluorescent tissues to confirm the presence of 100 parent ion (m/z=660.0 $[M+2]_{2+}$).

Figure 4B:
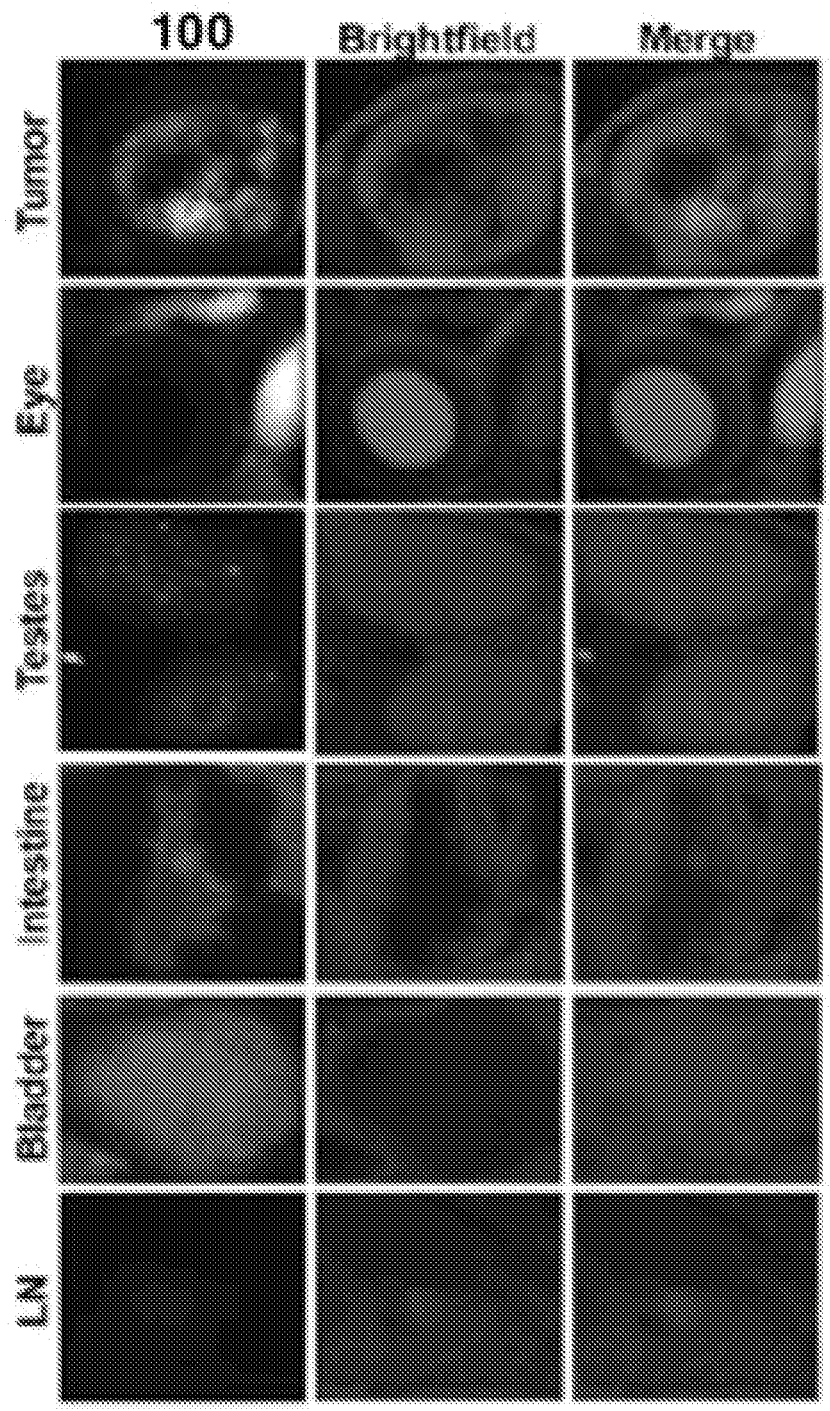

The 3D fluorescence static images in FIGS. 4a-b show bright fluorescence associated with the gall bladder, bile ducts, and upper intestinal tract. Fluorescence in these regions, however, is also observed in the non-injected control mouse. MS analysis of the intestines isolated from an animal (6 hr post-drug injection) did not show the presence of the parent 100 ion. It is thought that the origin of the fluorescence in the intestine and gall bladder is due to natural fluorescent compounds within the mouse food. FIG. 4b also shows a higher resolution cross section of a representative region of the upper intestine. All of the fluorescence is associated with the digested material in the lumen with no evidence of 100 in the gut wall or endothelial lining. Diarrhea is a dose limiting toxicity associated with many Hsp90 inhibitors in clinical trials and is thought to be related to inhibition of cell proliferation of the endothelial wall lining the upper and lower intestines. The lack of uptake of 100 suggests that the intestinal endothelium does not express or internalize eHsp90. Other fluorescent regions include the Harderian glands behind the eye and a thin layer within the eyes (FIGS. 4a and b). However, MS analysis of the eyes did not show evidence of the 100 parent ion. The Harderian glands are found in all rodents (and some other species) and are a photo-protective organ that excretes a complex oily fluorescent substance used to preen the fur. This fluorescence can also be seen in the control mouse, suggesting it is autofluorescence. Other major organs including heart, lungs, liver, kidney, spleen, brain, skeletal muscle, stomach, skin, thyroid, prostate and fur were completely devoid of 100 related fluorescence at the 6 hour time point. Aside from fluorescence that had leaked from the injection site, 100 was cleared from the entire vasculature by the 6 hour time point. No uptake of the 100 was detected in the any of the skeletal structures, including long bones, bone marrow, spine, skull, vertebrae, ribs, pelvis, spinal fluid, and synovial fluid within joints. This was also confirmed by MS analysis.

Significant fluorescence specifically associated with 100 was detected in the bladder and flank tumor. Overlay of the bright field image section with the fluorescence showed that all of the fluorescence was associated with urine within the bladder and not the bladder itself (FIG. 4b). This was confirmed by MS analysis of the urine that detected the parent ion at a concentration approximately 50 nM. These results suggest 100 is primarily eliminated intact through the kidney. Examination of both the bright field image of the tumor as well as a 3D reconstruction of the tumor mass shows its anatomy including the fibrotic wall, necrotic regions, microvasculature and live tumor tissue (FIG. 4b). When the fluorescence image is overlaid on the bright field image, 100 uptake is shown to be exclusively associated with live tumor tissue and not the fibrotic wall or necrotic regions. MS analysis confirmed the presence of the intact parent 100 molecule at a concentration of ~325 nM (w.w.). Faint fluorescence was also detected in the testes. Finally, analysis suggests uptake of 100 into the lymph nodes in several places around the animal. Readily visible nodes include the superficial parotid node in the neck region, the proper axillary node, and the subiliac and sciatic nodes in the forelimb and hindlimb regions, respectively. Higher magnification of the individual lymph nodes shows discrete staining within the node itself confined to a few cellular structures in the hilum. Although Hsp90 inhibition has repressive effects on T lymphocytes, the uptake of 100 into the lymph nodes is unlikely to involve T cells because the studies used SCID mice.

Figure 4C:
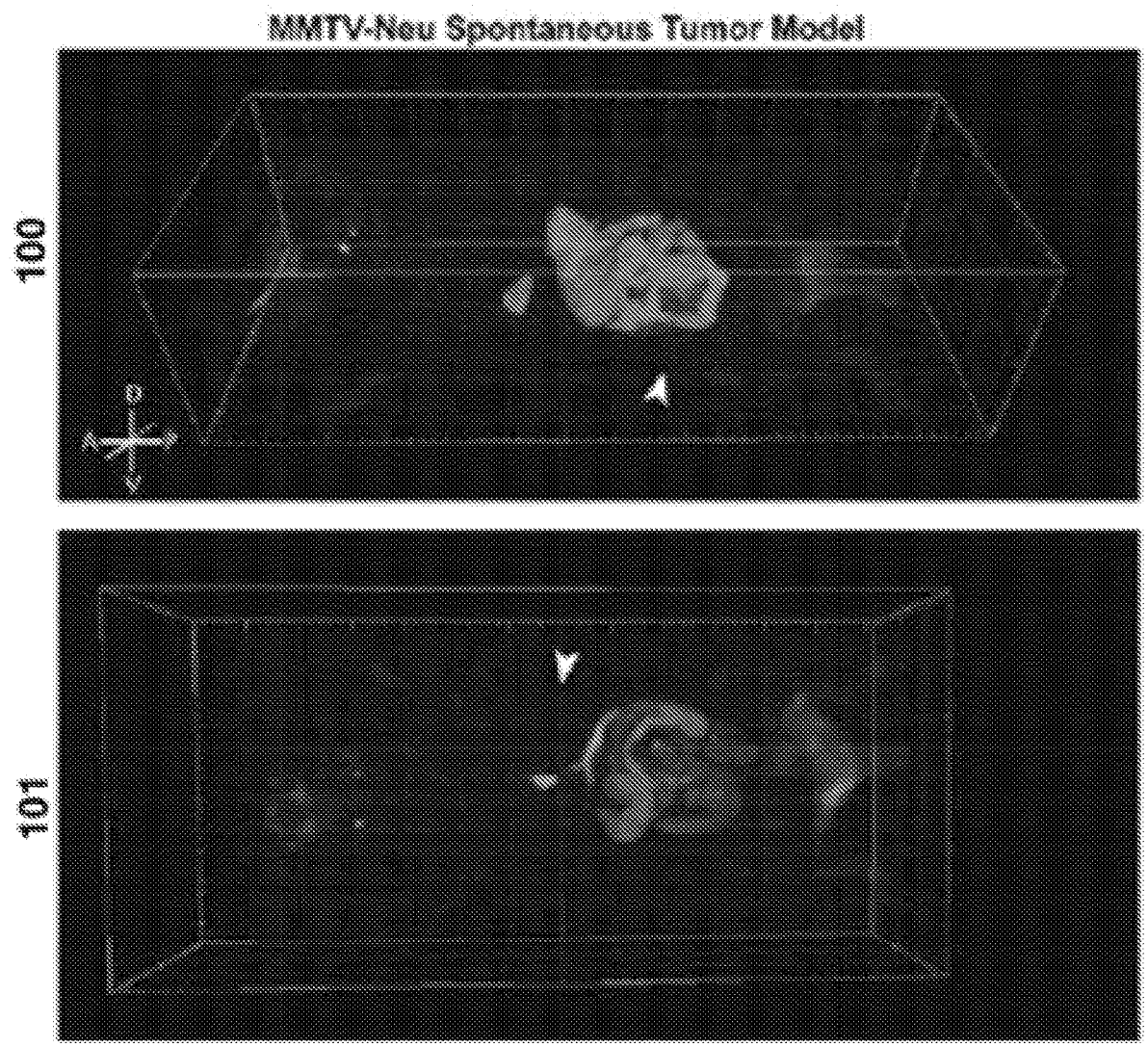
Figure 4D:
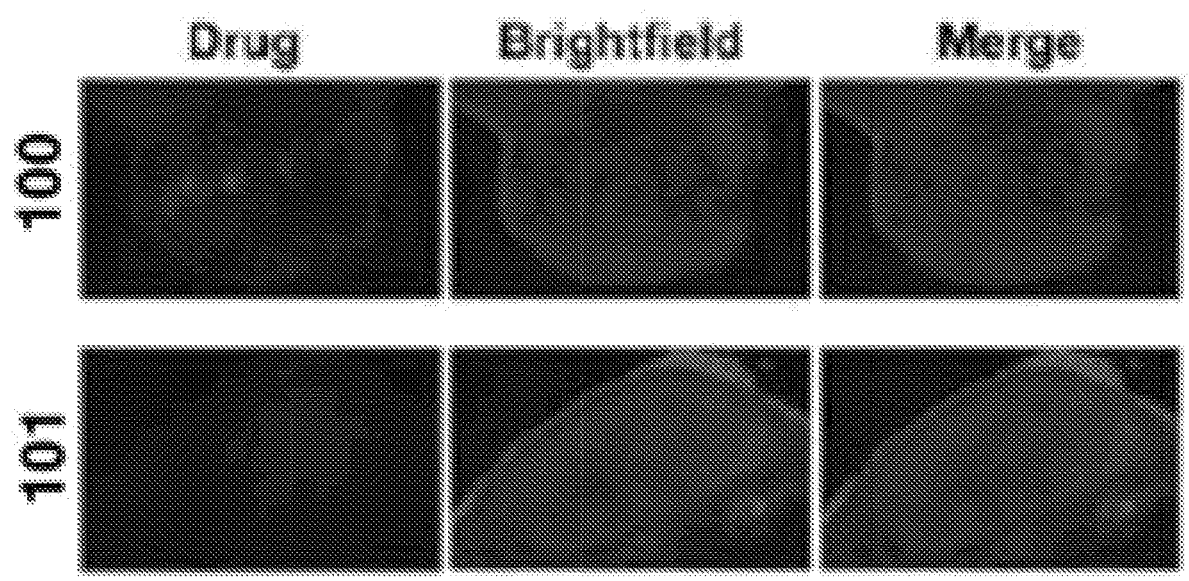
Figure 5:
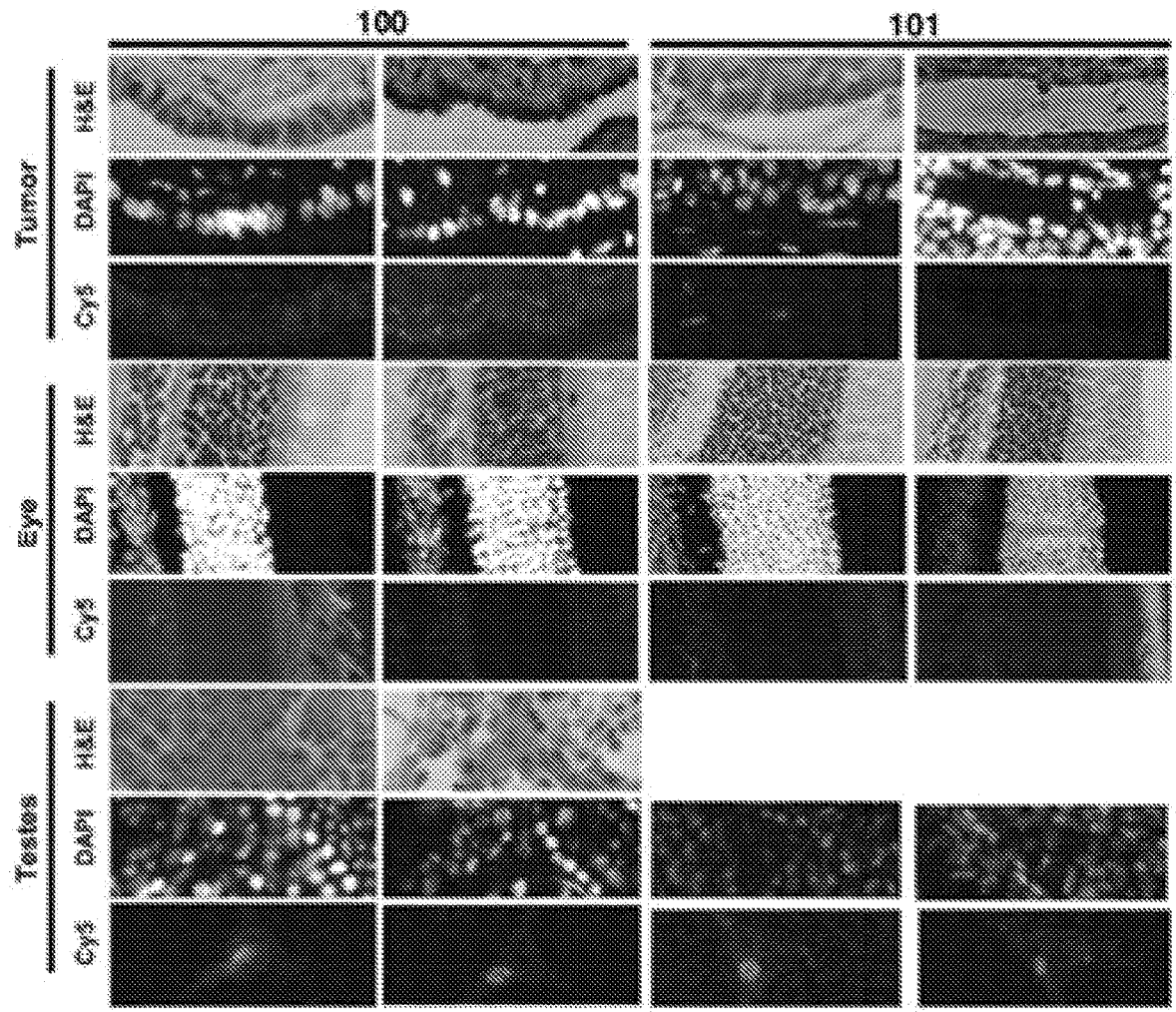
FIG. 5. Histology of fluorescent tissues reveals tumor specificity. Serial sections of various organs were imaged, either with H&E staining or with DAPI/Cy5 (drug) fluorescence. Specific drug fluorescence is observed in duct epithelium of tumor cells in the 100-treated mouse, but not in the 101-treated mouse. Tissues from the 101-treated mouse reveal autofluorescence in the rods and cones layer of the eye and in the Leydig cells of the testes.

Flank tumors, due to their homogeneity, do not accurately reflect the physiology of human tumors. To investigate the tumor specificity and eHsp90 internalization in a more relevant model of human breast cancer, the MMTV-neu spontaneous mammary tumor mouse model was used (FIGS. 4c-d). Two MMTV-neu mice bearing equal sized mammary tumors (~150 mm$_3$) were injected in parallel (i.v.) with 25 nmol of 100 or the inactive analog 101, and after 6 hours the animals cryopreserved as previously described. Following cryoslicing, each 40 μm slice was imaged for fluorescence and brightfield. FIGS. 4c and d also show that the 100 uptake is confined to the tumor in comparison to 101, confirming that probe uptake is eHsp90-dependent. Importantly, 100 shows the same biodistribution as observed with the flank tumor animal shown in FIG. 5a. Interestingly, 100 uptake in the MMTV tumor mass is more discrete than the more homogenous uptake in the flank tumor. Closer inspection via histology revealed that 100 fluorescence within the MMTV tumor is confined to select areas of ductal epithelial cells (FIG. 5). Based on studies with isolated breast cell lines, these findings suggest that the cells discretely stained within 100 exhibit a malignant phenotype and may be analogous to ductal carcinoma in situ (DCIS) in human breast cancer. No uptake was observed in these cells within the tumor isolated from the 101-treated animal, again supporting the hypothesis that 100 is eHsp90 dependent. In addition, comparison with tissues from the 101-treated mice revealed that the previously observed fluorescence within the rod and conelayer of the eyes and the Leydig cells of the testes were due to autofluorescence (FIG. 5). Previous studies have reported the autofluorescence of Leydig cells in the testes due to the presence of a lipophilic pigment.

The sensitivity of the approach was illustrated with the detail shown in FIG. 4 and 3D movies, and more so upon close inspection of the archived longitudinal images. Analysis of the tumor mass for example shows uptake on 100 is confined to living tumor tissue and not the walled off or necrotic regions. Moreover, while this experiment shed light on the biodistribution of 100 throughout the body, flank tumors are often criticized for their unrealistic homogeneity. In vivo tumors exhibit vast heterogeneity and a much more complex anatomy than a flank tumor. However, the MMTV-neu mouse model develops spontaneous mammary tumors that are more indicative of real patient tumors. Importantly, cryosectioning revealed small clusters of 100-positive cells within the tumor tissue, which was further confirmed in higher resolution histological analysis which showed that 100 fluorescence was confined within the epithelial ducts.

Example 29. Expression of eHsp90 is Common in Cells with an Aggressive Malignant Cellular Phenotype Studies with 100 in other tumor cells (e.g., glioblastoma, non-small lung, prostate, and melanoma lines) suggest that expression of eHsp90 is common to cells with an aggressive malignant cellular phenotype.

Example 30. MDA-MB-231 Tumor Imaging

Figure 6:
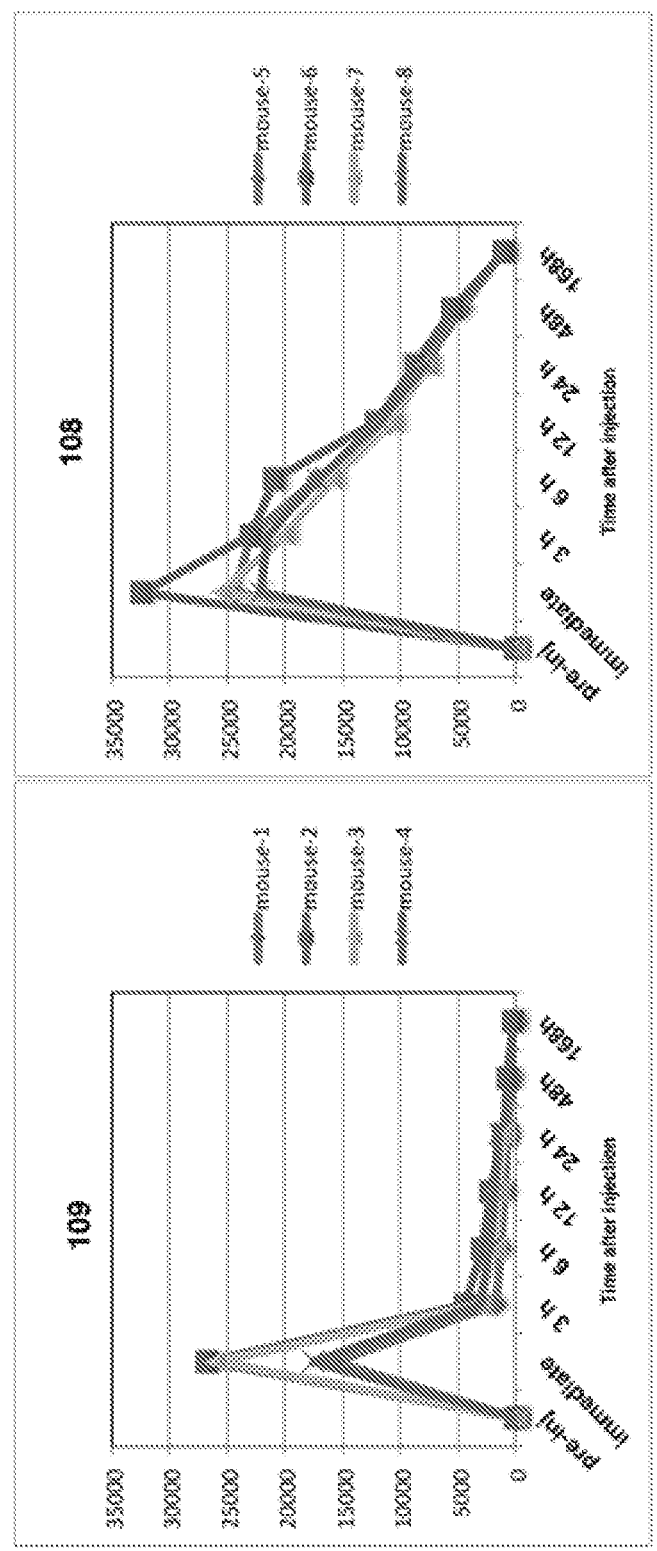
FIG. 6. Over Time Change of nIR Signal from MDA-MB-231 Tumors in HS196/HS199 injected mice. When the MDA-MB-231 tumor sizes reached about 10 mm in diameter, HS196 or HS199 (1 nmol/50 μl saline) was injected to mice via tail vein. nIR signals from the tumor area were detected by LI-COR Pearl Imager using 800 nm channel. 4 mice for each group. Over time change of the nIR signal is plotted for individual mice.
Figure 7:
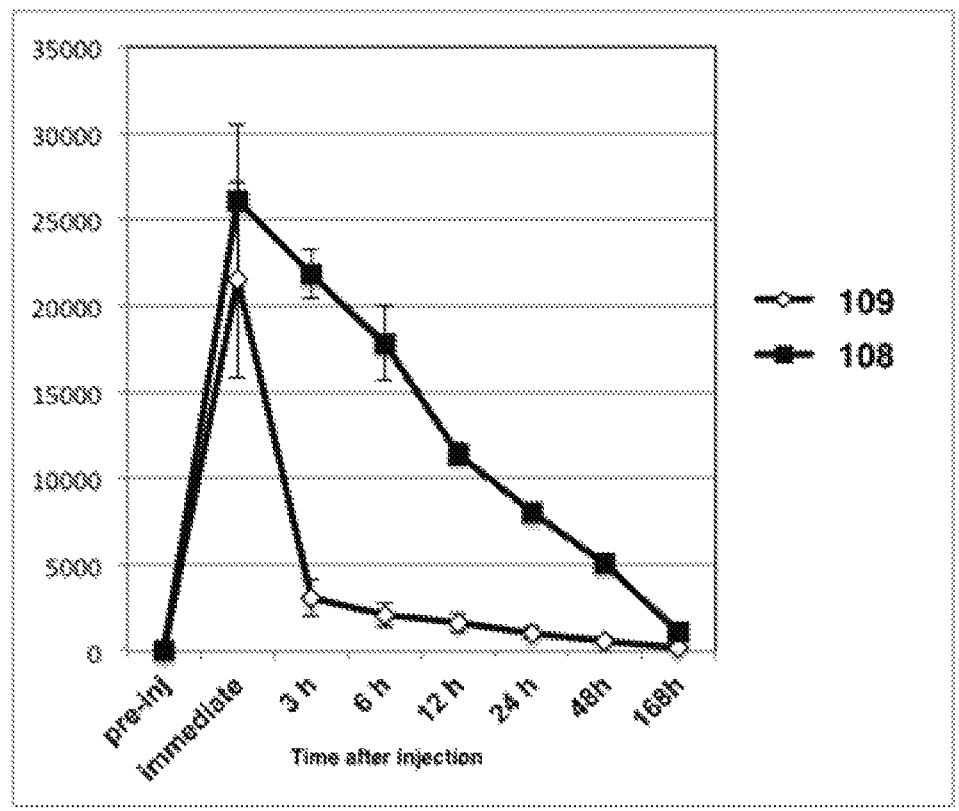
FIG. 7. Over Time Change of nIR Signal from MDA-MB-231 Tumors in HS196/HS199 injected mice. When the MDA-MB-231 tumor sizes reached about 10 mm in diameter, HS196 or HS199 (1 nmol/50 μl saline) was injected to mice via tail vein. nIR signals from the tumor area were detected by LI-COR Pearl Imager using 800 nm channel. 4 mice for each group. Average value for each group is shown. Error Bar:SD

Change Over Time of nIR Signal from MDA-MB-231 Tumors in 108/109 injected mice. When the MDA-MB-231 tumor sizes reached about 10 mm in diameter, imaging agent 108 or 109 (1 nmol/50 µl saline) was injected to mice via tail vein. nIR signals from the tumor area were detected by LI-COR Pearl Imager using 800 nm channel. 4 mice for each group. The change over time of the nIR signal is plotted for individual mice. See FIGS. 6-7.

The invention claimed is:
1. A compound of formula (I):

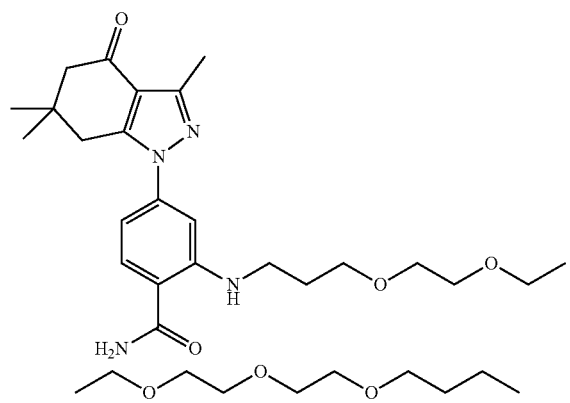

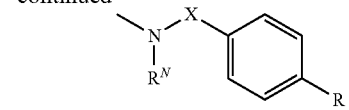

or a stereoisomer or salt thereof;
wherein
X is —CH$_2$— or —C(O)—;
R$^N$ is H, —CH$_2$(C$_6$H$_4$)—I, or —CH$_2$(C$_6$H$_4$)—Sn(CH$_3$)$_3$;
R is

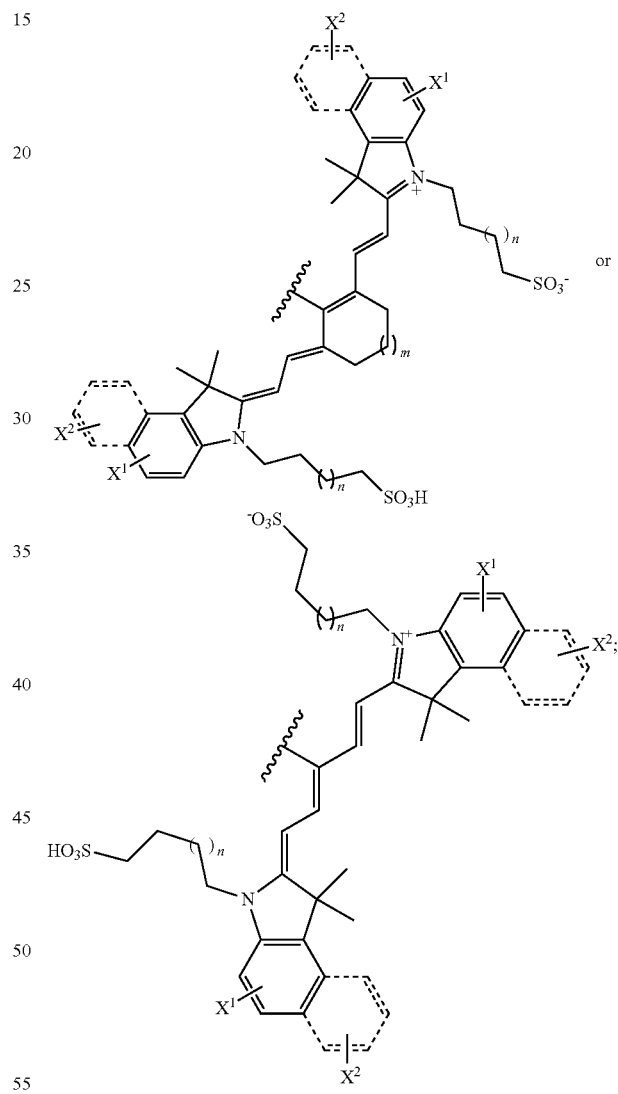

each X$^1$ and X$^2$, if present, are independently selected from H and SO$_3$H;
n is 0 or 1;
m is 0 or 1; and
the dotted lines show an optional fused ring.
2. The compound according to claim 1, or a stereoisomer or salt thereof, wherein X is —CH$_2$—.
3. The compound according to claim 1, or a stereoisomer or salt thereof, wherein X is —C(O)—.
4. The compound according to claim 1, or a stereoisomer or salt thereof, wherein R$^N$ is H.

5. The compound according to claim 1, or a stereoisomer or salt thereof, wherein $R^N$ is —CH$_2$(C$_6$H$_4$)—I.
6. The compound according to claim 1, or a stereoisomer or salt thereof, wherein R is
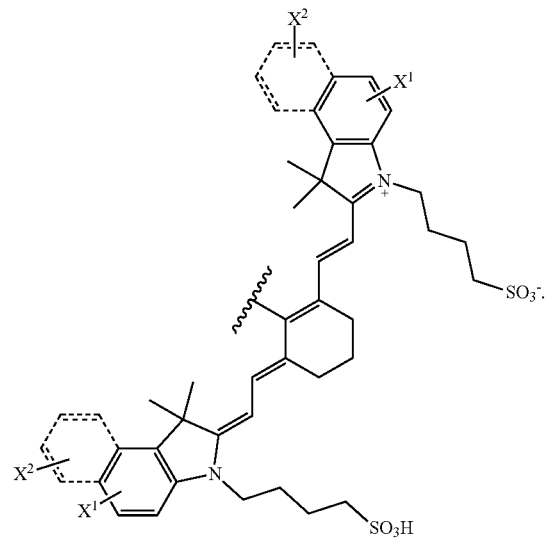
7. The compound according to claim 1, or a stereoisomer or salt thereof, wherein R is
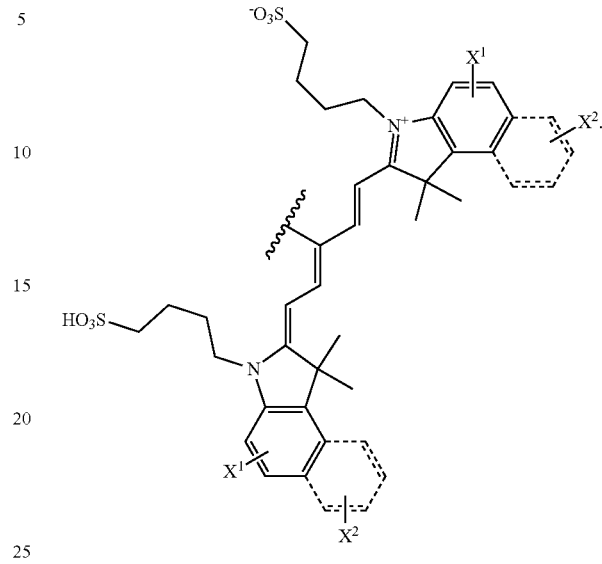
8. A compound according to claim 1 selected from:
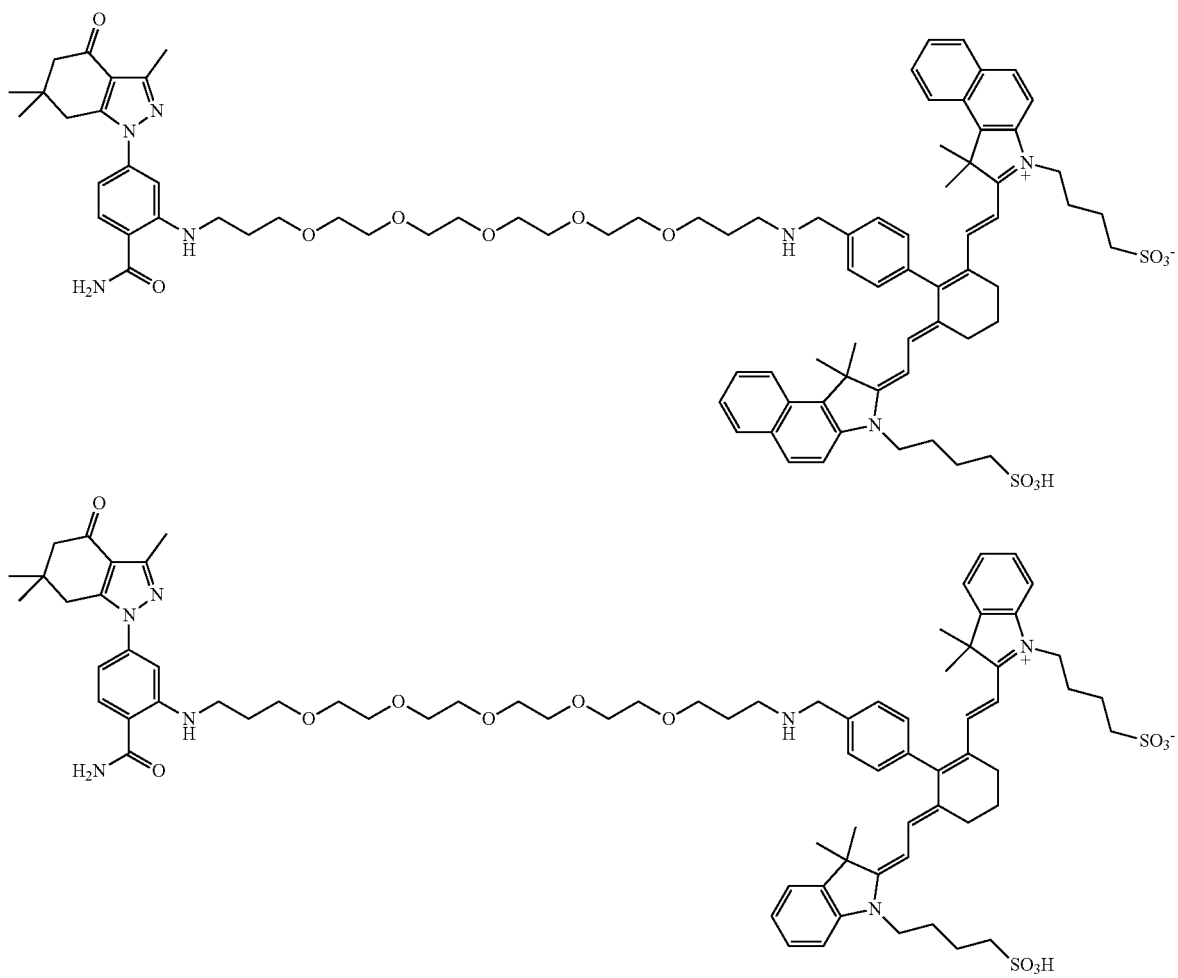

111 112
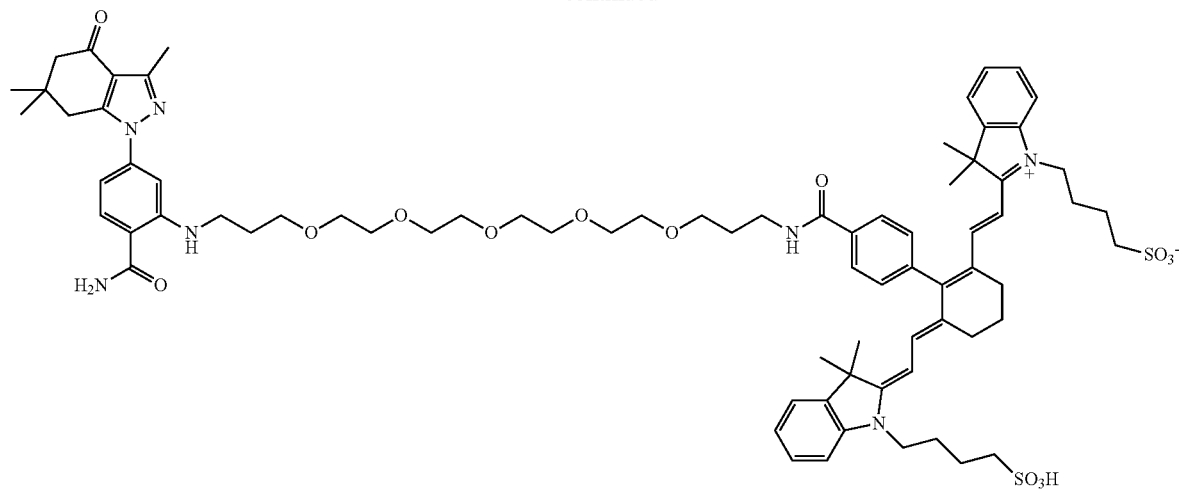
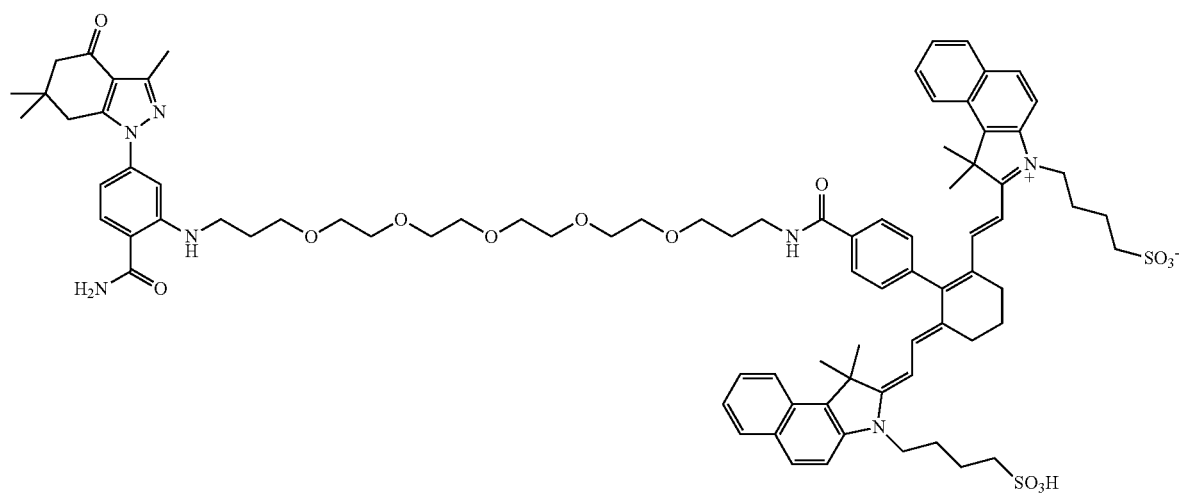
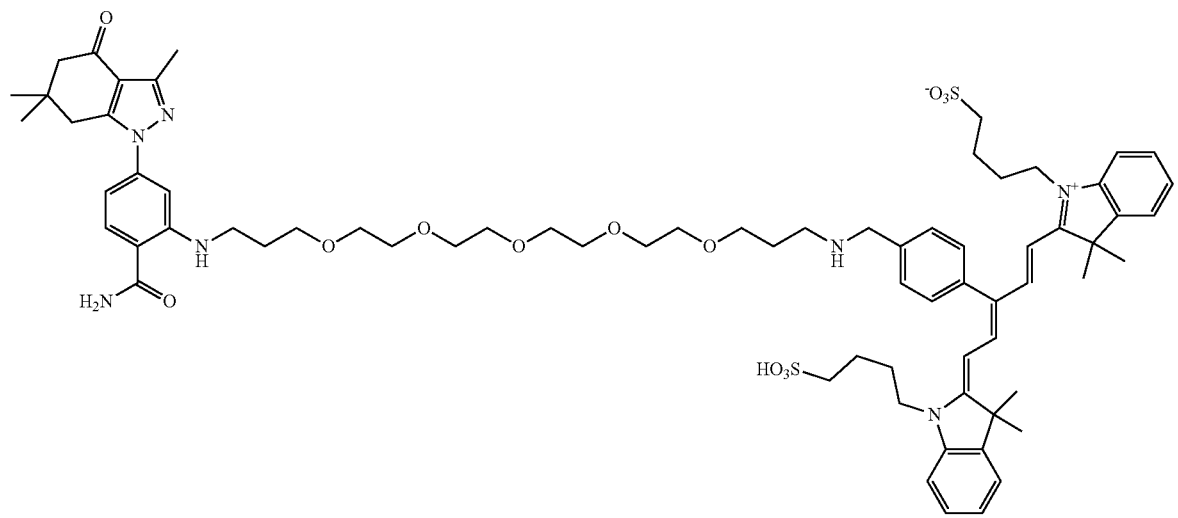

113
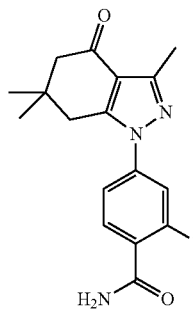
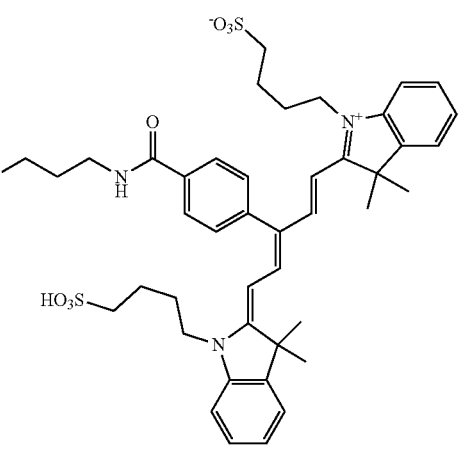
114
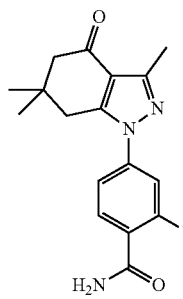
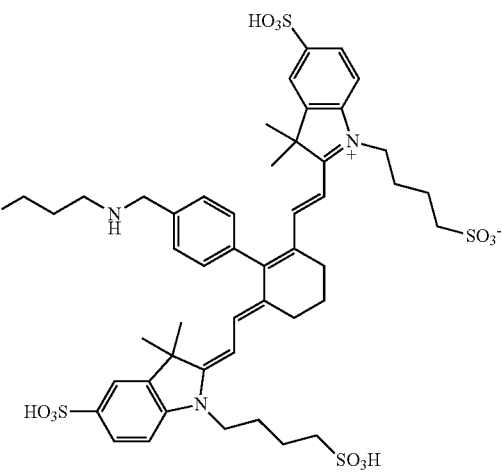
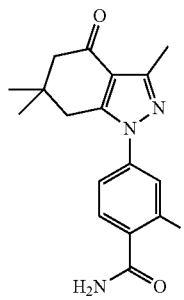
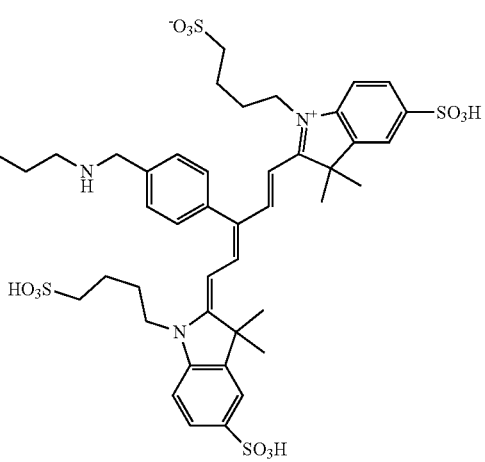

115

-continued

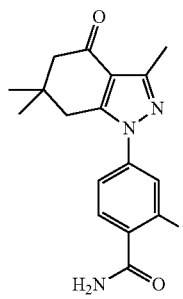
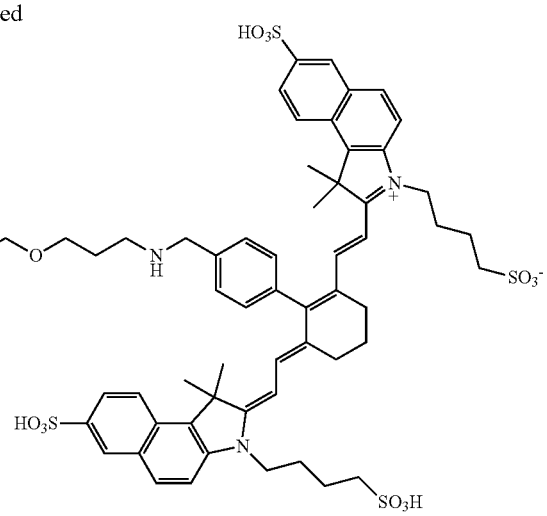

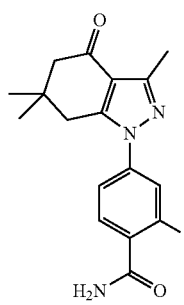
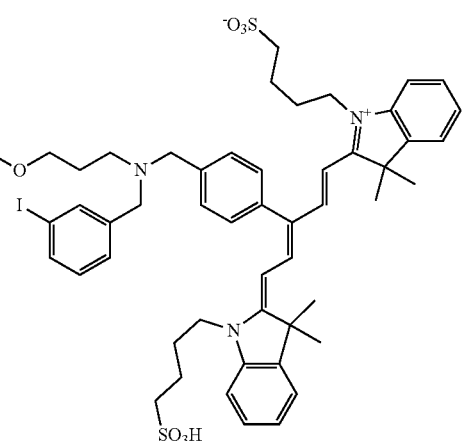

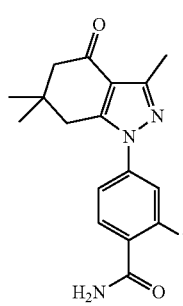
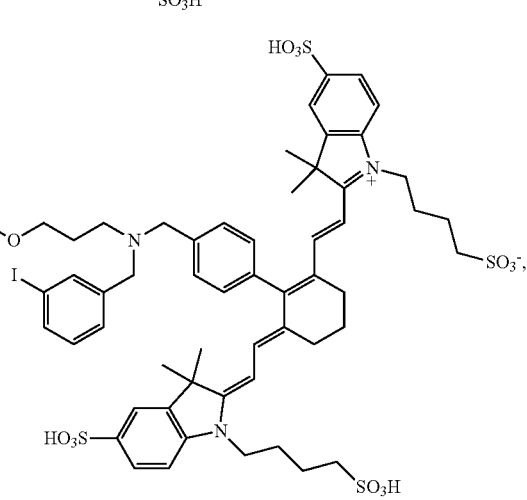

116 stereoisomer or salt thereof.

9. A method of detecting Hsp90 in a sample, comprising:
a) contacting the sample with a compound according to claim 1, or a stereoisomer or salt thereof; and b) detecting a signal.

10. The method of claim 9, wherein the Hsp90 is eHsp90.

11. A method of detecting cancer in a subject, comprising:
a) contacting a biological sample from the subject with a compound according to claim 1, or a stereoisomer or salt thereof; and b) detecting a signal; and optionally obtaining the biological sample from the subject wherein cancer is detected in the sample when the signal is higher relative to a signal from a reference sample, wherein the cancer is selected from the group consisting of breast cancer, prostate cancer, non-small lung cancer, colorectal cancer, pancreatic cancer, ovarian cancer, melanoma, liver cancer, Wilms tumor, and cervical cancer.

12. The method of claim 11, wherein the cancer is selected from the group consisting of breast cancer, prostate cancer, non-small cell lung cancer, colorectal cancer, pancreatic cancer, ovarian cancer, and melanoma.

13. A method of treating cancer in a subject in need of treatment, comprising administering to the subject a therapeutically effective amount of a compound according to claim 1, or a stereoisomer or salt thereof, wherein the cancer is selected from group consisting of breast cancer, prostate cancer, non-small cell lung cancer, colorectal cancer, pancreatic cancer, ovarian cancer, melanoma, liver cancer, Wilms tumor, and cervical cancer.

14. The method of claim 13, wherein the subject has a cancer selected from the group consisting of breast cancer, prostate cancer, non-small cell lung cancer, colorectal cancer, pancreatic cancer, ovarian cancer and melanoma.

15. A pharmaceutical composition comprising a compound according to claim 1, or a stereoisomer or salt thereof, and a pharmaceutically acceptable carrier.

16. A kit comprising a compound according to claim 1 or a stereoisomer or salt thereof.

17. A compound selected from:

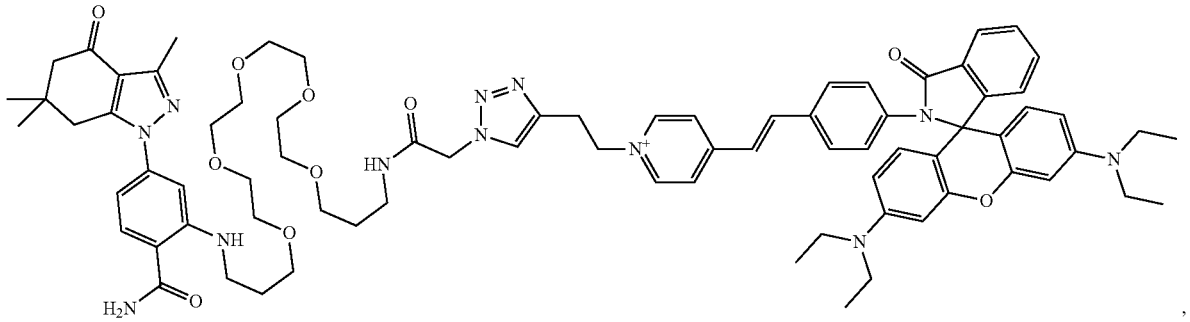

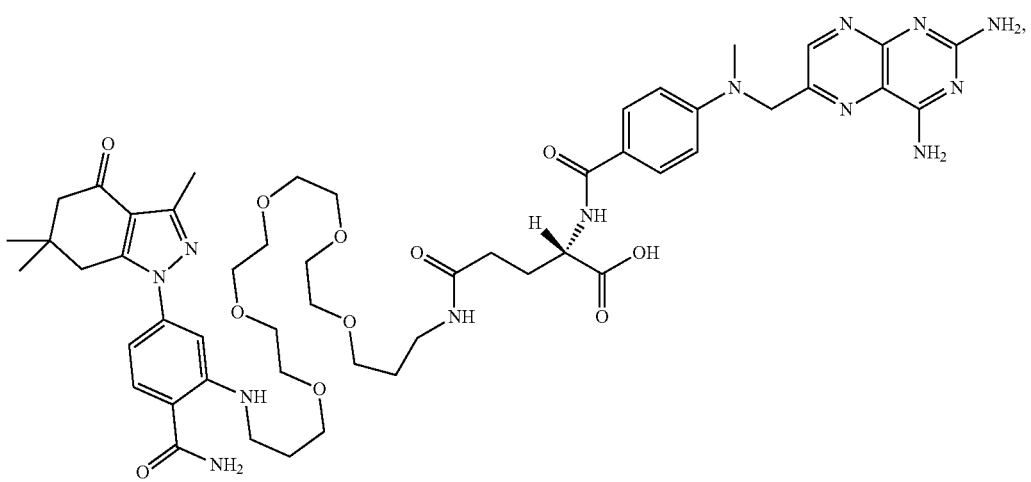

-continued
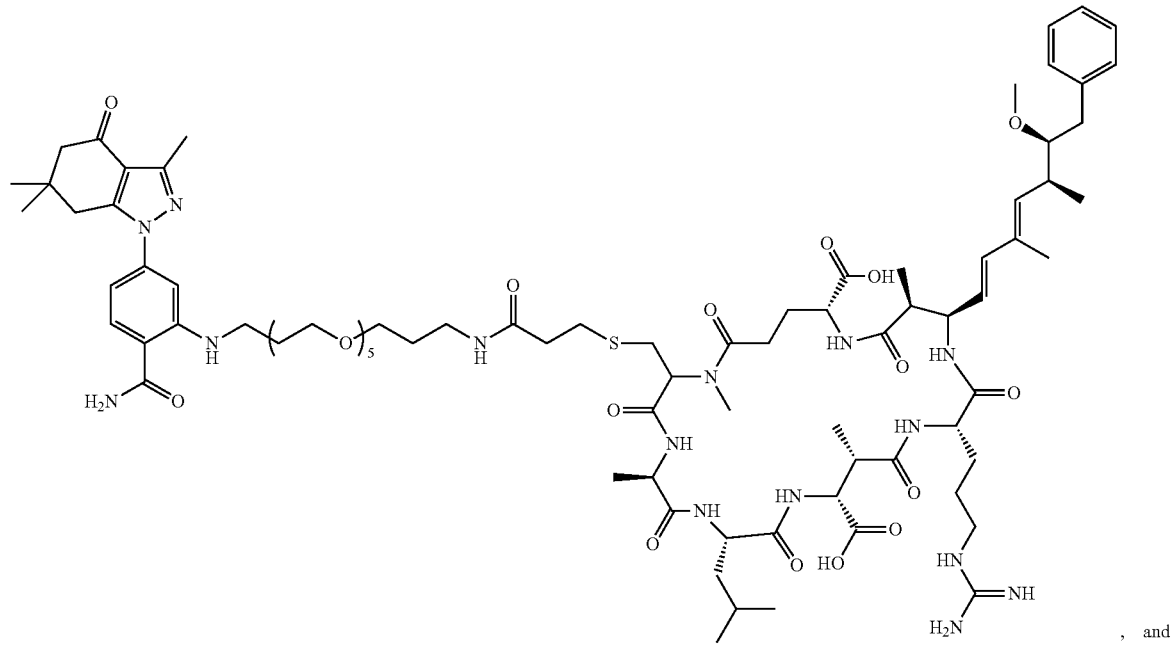
, and
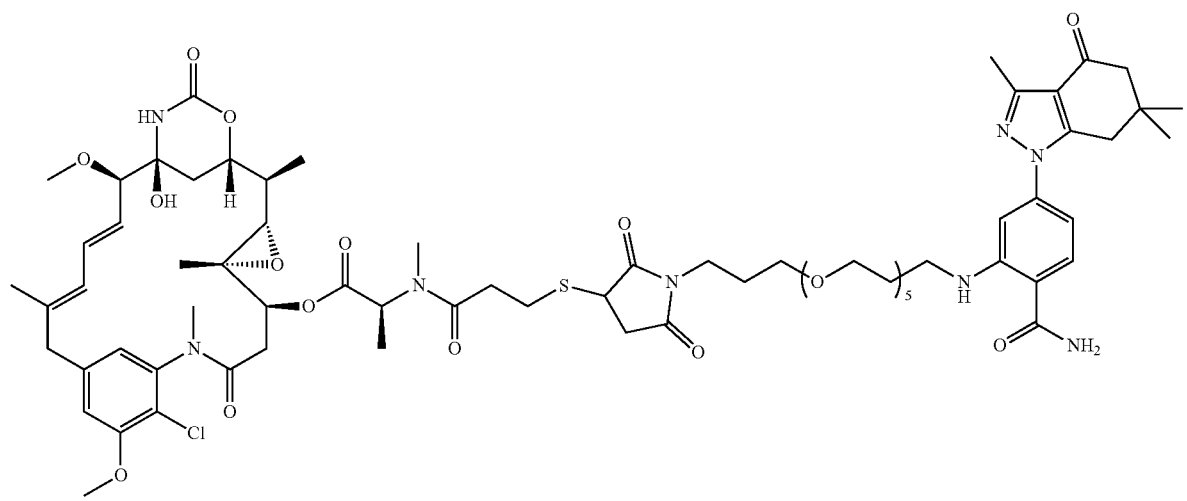
,
or a stereoisomer or salt thereof.

18. A pharmaceutical composition comprising a compound according to claim 17, or a stereoisomer or salt thereof, and a pharmaceutically acceptable carrier.

19. A kit comprising a compound according to claim 17, or a stereoisomer or salt thereof.

20. The compound according to claim 8 selected from

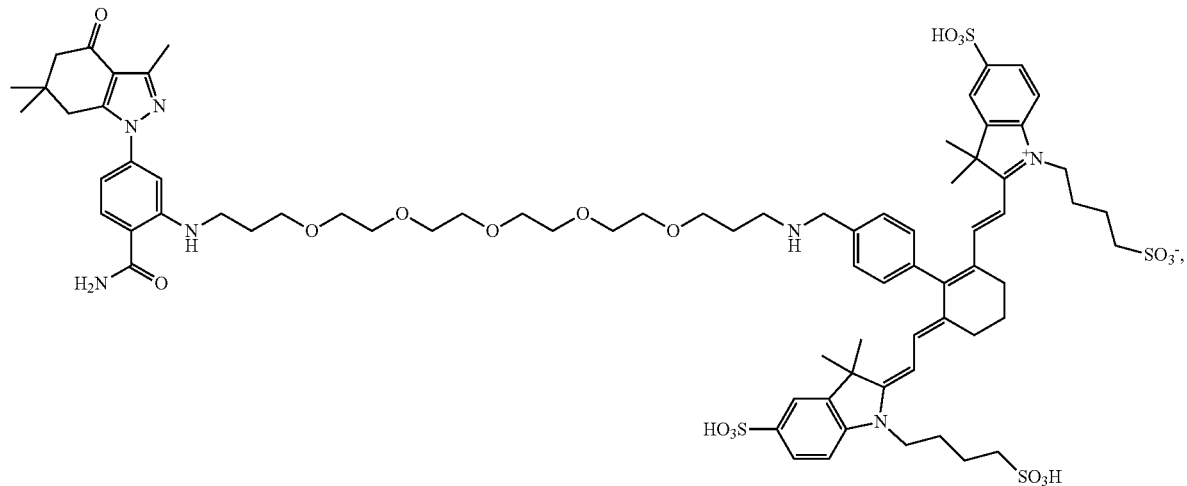

or a stereoisomer or salt thereof.

21. A compound according to claim 1, or a stereoisomer or salt thereof, the compound having the formula

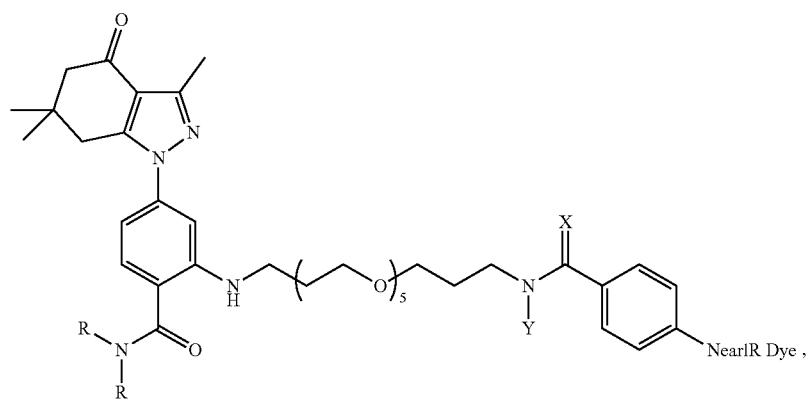

123
| R | X | Y | Dye |
|---|---|---|---|
| H | $H_2$ | H | 12 |
| H | O | H | 12 |
| H | $H_2$ | H | 13 |
| H | $H_2$ | H | 14 |
| H | O | H | 14 |
| H | $H_2$ | H | 15 |
| H | $H_2$ | H | 16 |
| H | $H_2$ | H | 17 |
| H | O | H | 17 |
| H | $H_2$ | H | 18 |
| H | $H_2$ | —$CH_2C_6H_4$—I | 12 |
| H | $H_2$ | —$CH_2C_6H_4$—I | 15 |
| H | $H_2$ | —$CH_2C_6H_4$—$Sn(CH_3)_3$ | 12 |
and the NearIR Dyes having formulas
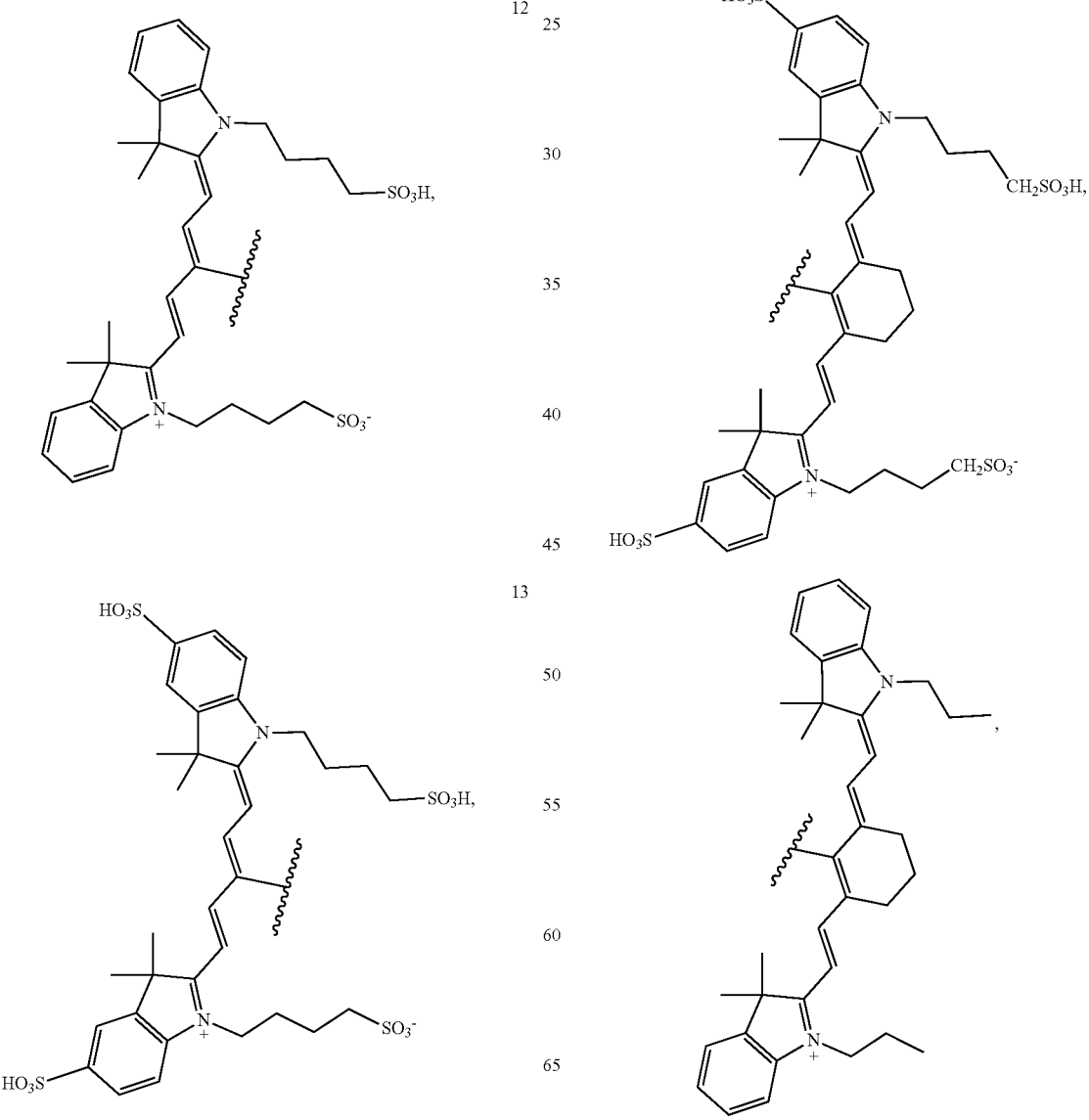
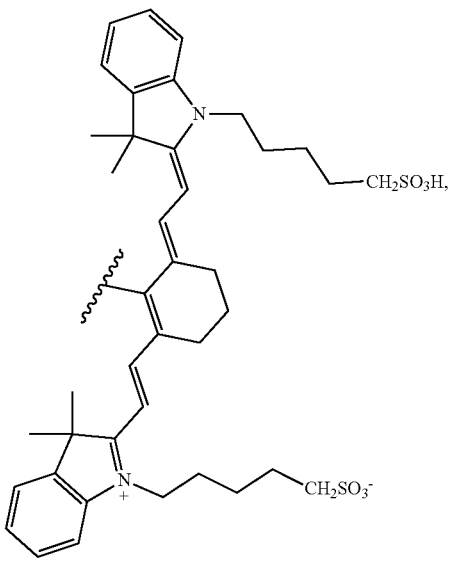

125
-continued
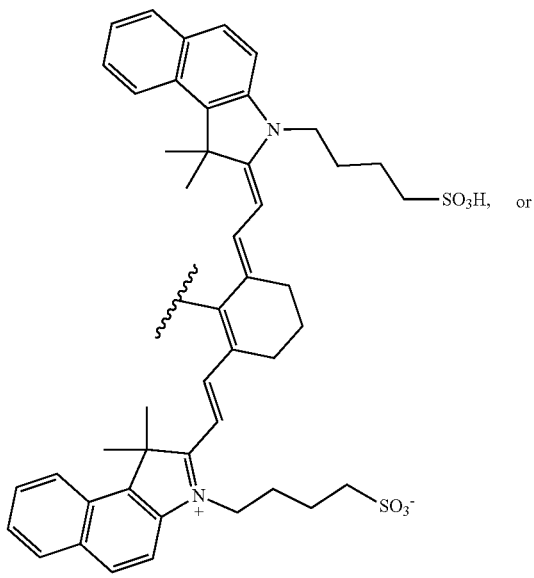
17
, or
126
-continued
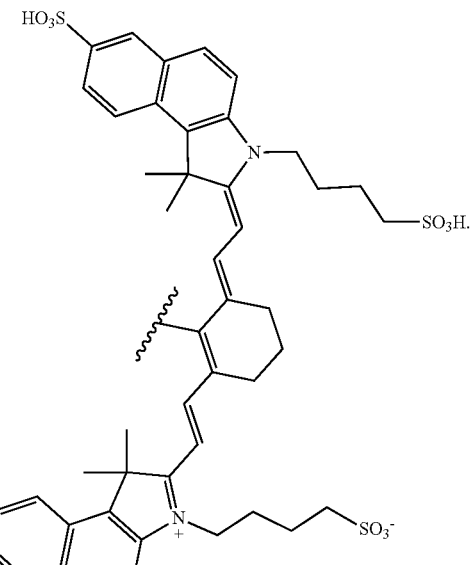
18
.
* * * * *